(12) United States Patent
Albone et al.

(10) Patent No.: US 8,299,230 B2
(45) Date of Patent: Oct. 30, 2012

(54) NUCLEIC ACID MOLECULES ENCODING ANTIBODIES THAT BIND CELL-ASSOCIATED CA 125/O772P

(75) Inventors: Earl F. Albone, Plymouth Meeting, PA (US); Daniel A. Soltis, Cleveland Heights, OH (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 13/354,952

(22) Filed: Jan. 20, 2012

(65) Prior Publication Data

US 2012/0149892 A1    Jun. 14, 2012

Related U.S. Application Data

(62) Division of application No. 12/183,719, filed on Jul. 31, 2008, now Pat. No. 8,124,086, which is a division of application No. 10/687,035, filed on Oct. 15, 2003, now Pat. No. 7,429,382.

(60) Provisional application No. 60/485,986, filed on Jul. 10, 2003, provisional application No. 60/418,828, filed on Oct. 16, 2002.

(51) Int. Cl.
*C07H 21/04* (2006.01)

(52) U.S. Cl. .................................. 536/23.53

(58) Field of Classification Search .................. None
See application file for complete search history.

(56) References Cited

U.S. PATENT DOCUMENTS

| | | | |
|---|---|---|---|
| 4,921,790 | A | 5/1990 | O'Brien |
| 5,059,680 | A | 10/1991 | Davis et al. |
| 5,366,866 | A | 11/1994 | Xu et al. |
| 5,486,456 | A | 1/1996 | Xu et al. |
| 5,650,291 | A | 7/1997 | Lee |
| 5,693,762 | A | 12/1997 | Queen et al. |
| 5,858,361 | A | 1/1999 | Wagner et al. |
| 5,871,941 | A | 2/1999 | Auersperg |
| 5,976,818 | A | 11/1999 | O'Brien |
| 6,136,310 | A | 10/2000 | Hanna et al. |
| 6,241,985 | B1 | 6/2001 | Madiyalakan et al. |
| 6,376,654 | B1 | 4/2002 | Gelber |
| 6,468,546 | B1 | 10/2002 | Mitcham et al. |
| 6,488,931 | B1 | 12/2002 | Mitcham et al. |
| 6,528,253 | B1 | 3/2003 | Mitcham et al. |
| 6,670,463 | B1 | 12/2003 | Mitcham et al. |
| 6,699,664 | B1 | 3/2004 | Mitcham et al. |
| 7,429,382 | B2 | 9/2008 | Albone et al. |
| 8,124,086 | B2 | 2/2012 | Albone et al. |
| 2002/0009451 | A1 | 1/2002 | O'Brien |
| 2002/0022591 | A1 | 2/2002 | Algate et al. |
| 2002/0037287 | A1 | 3/2002 | Gelber |
| 2002/0081609 | A1 | 6/2002 | Dillon et al. |
| 2002/0119158 | A1 | 8/2002 | Algate et al. |
| 2003/0008299 | A1 | 1/2003 | Algate |
| 2003/0082655 | A1 | 5/2003 | O'Brien |
| 2003/0091580 | A1 | 5/2003 | Mitcham et al. |
| 2003/0104442 | A1 | 6/2003 | Lloyd et al. |
| 2003/0124140 | A1 | 7/2003 | Bangur et al. |
| 2003/0165504 | A1 | 9/2003 | Retter et al. |
| 2004/0127401 | A1 | 7/2004 | O'Brien |

FOREIGN PATENT DOCUMENTS

| | | |
|---|---|---|
| EP | 0 332 651 B2 | 12/1996 |
| EP | 1256354 | 11/2002 |
| WO | WO89/01629 | 2/1989 |
| WO | WO94/27637 | 8/1994 |
| WO | WO96/31539 | 10/1996 |
| WO | WO00/36107 | 6/2000 |
| WO | WO0036107 | 6/2000 |
| WO | WO01/40269 | 6/2001 |
| WO | WO01/60860 | 8/2001 |
| WO | WO0157207 | 8/2001 |
| WO | WO01/70804 | 9/2001 |
| WO | WO01/70979 | 9/2001 |
| WO | WO01/75177 | 10/2001 |
| WO | WO01/85203 | 11/2001 |
| WO | WO02/00677 | 1/2002 |
| WO | WO0206317 | 1/2002 |
| WO | WO0207783 | 1/2002 |
| WO | WO02/071928 | 9/2002 |
| WO | WO02/074961 | 9/2002 |
| WO | WO02/076384 | 10/2002 |
| WO | WO02083866 | 10/2002 |
| WO | WO02/092836 | 11/2002 |
| WO | WO02092836 | 11/2002 |
| WO | WO03076465 | 9/2003 |
| WO | WO03076473 | 9/2003 |

(Continued)

OTHER PUBLICATIONS

Bast et al. (1981) "Reactivity of a Monoclonal Antibody with Human Ovarian Cacrcin" *J. Clin Invest* 68(5): 1331-37.

Boshell et al. (1992) "The Product of the Human MUC1 Gene When Secreted by Mouse Cells Transfected With the Full-Length cDNA Lacks Cytoplasmic Tail" *Biocehm and Biophys Res. Comm* 185(1):1-8.

Frailes et al. (1993) "Purification and Characterization of the CA 125 Tumor-Associated Antigen From Human Ascites" Tumour Biol. 1993:14(1):18-29.

Gadducci et al. (1992), "The Concorniant Determination of Different Tumor Markers in Patients with Epithelial Ovarian Cancer and Benign Ovarian Masses: Relevance for Differential Diagnosis", *Gynecol Oncol.* 44(2):147-54.

(Continued)

*Primary Examiner* — Laura B Goddard
(74) *Attorney, Agent, or Firm* — Sterne, Kessler, Goldstein & Fox P.L.L.C.

(57) ABSTRACT

The present invention provides antibodies, and antigen-binding fragments of antibodies, fusion polypeptides and analogs that preferentially bind cell-associated CA 125/O772P polypeptides relative to shed CA 125/O772P polypeptides. The present invention further provides methods of preventing, managing, treating or ameliorating one or more symptoms associated with a CA 125/O772P-related disorder. In particular, the present invention provides methods of preventing, managing, treating, or ameliorating one or more symptoms associated with a cell proliferative disorder, such as cancer, e.g., ovarian cancer. The present invention still further provides methods for diagnosing a CA 125/O772P-related disorder or predisposition to developing such a disorder, as well as methods for identifying antibodies, and antigen-binding fragments of antibodies, that preferentially bind cell-associated CA 125/O772P polypeptides relative to shed CA 125/O772P polypeptides.

2 Claims, 12 Drawing Sheets

FOREIGN PATENT DOCUMENTS

Figure 3:
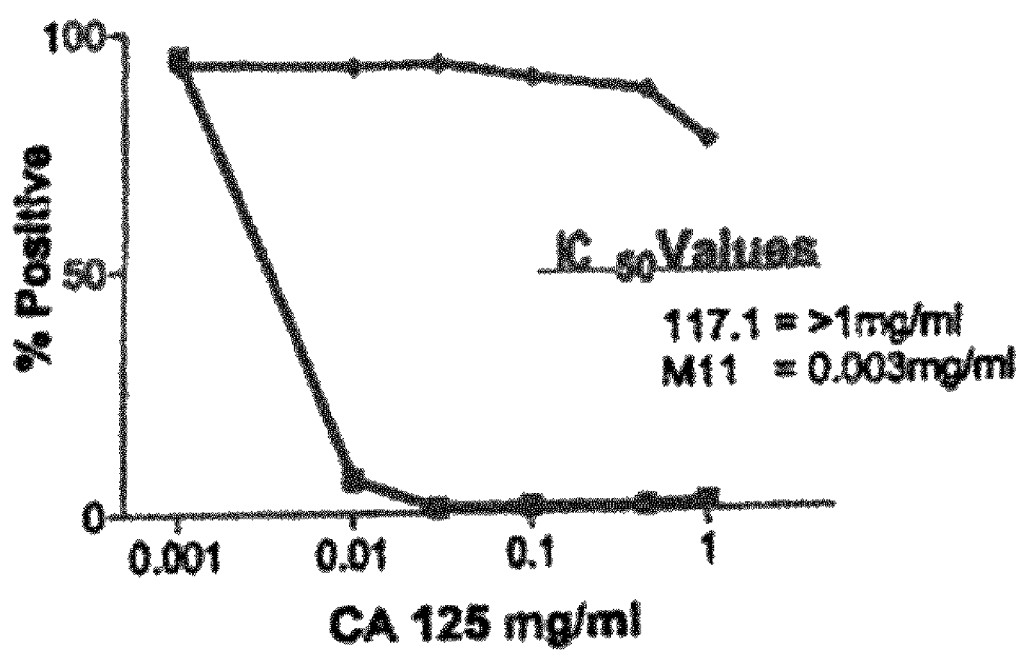

| | | |
|---|---|---|
| WO | WO2004005470 | 1/2004 |
| WO | WO2004045553 | 5/2004 |

OTHER PUBLICATIONS

Hovig et al. (2001) "CA 125: The End of the Beginning" *Tumor Bio.* 22:345-47.

Hu et al. (2003) "Discovery and Validation of New Molecular Targets of Ovarian Cancer" *Current Opinion in Molecular Therapeutics.* 5(6):625-630.

Kabawat et al. (1983) "Immunopathologic Characterization of a Monoclonal Antibody That Recognizes Common Surface Antigens of Human Ovarian Tumors of Serous, Endometrioid, and Clear Cell Types", Am. J. Clin. Pathol. 79:98-104.

Lightenberg et al. (1992) "Cell-Associated Episialin is a Complex Containing Two Proteins Derived From a Common Precursor" *The Journal of Biol. Chem.*, 267(9):6171-77.

Madiyalakan et al. (1997) "Ovarex MAb-B43.13:IFN-Gamma Could Improve the Ovarian Tumor Cell Sensitivity to CA 125-Specific Allogenic Cytotoxic T Cell" *Hybridoma* 16(1): 41-5.

Maeda et al. (2004) "Solution Structure of the SEA Domain From the Murine Homologue of Ovarian Cancer Antigen CA125 (MUC 16)" *The Journal of Biol. Chem.* 279(13): 13174-13182.

Noujaim et al. (2001) "Induction of CA125-Specific B and T Cell Responses in Patients Injected With MAb-B43.13—Evidence for Antibody-Mediated Anti-processing and Presentation of CA125 in Vivo" *Cancer Biother. Radiopharm* 16(3): 187-203.

Nustad et al. (1996) "Specificity and Affinity of 26 Monoclonal Antibodies Against the CA 125 Antigen: First Report From the ISOBM TD-1 Workshop. International Society for Oncodevelopmental Biology and Medicine" *Tumour Biol.* 17(4): 196-219.

Nustad et al. (2002) "Epitopes on CA 125 From Cervical Mucus and Ascites Fluid and Characterization of Six New Antibodies. Third report from the ISOBM TD-1 workshop," *Tumour .Biol.* 23(5): 303-314.

O'Brien et al. (2001) "The CA125 Gene: An Extracellular Superstructure Dominated by Repeat Sequences" *Tumor Bio.* 22:348-366.

O'Brien et al. (2002) "The CA125 Gene: A Newly Discovered Extension of the Glycosylated N-Terminal Domain Doubles the Size of This Extracellular Superstructure" *Tumor Bio.* 23:154-169.

Saga et al. (1990) "Construction of an Immunoradiometric Assay for Ovarian Cancer Antigen CA125 Recognizing Different Antigenic Determinant" *ACTA Obstet Gynecol. Scand.* 69(2):175-81.

Saga et al. (1990) "An Antibody-Tumor Model for the Targeting of CA125-Producing Gynecologic Malignancies" *Jpn J. Cancer Res.* 81(11):1141-48.

Yin et al. (2001) "Molecular Cloning of the CA125 Ovarian Cancer Antigen" *The Journal of Biol. Chem* 276(29):27371-375.

Andersson, et al., 1999 "Biokinetics of the Monoclonal Antibodies MOv 18, OV 185 and OV 197 Labelled with I According to the m-MeATE Method or the Iodogen Method in Nude Mice with Ovarian Cancer Xenografts", *ACTA Oncologica*, 38(3)323-323.

Bouvier, et al., 1988 "Serum Levels of Tumor Markers and Presence of Human Antimouse Antibodies: Implications for Diagnosis and Treatment with Radiolabeled Monoclonal Antibodies", *Cancer Detection and Prevention*, 13: 251-262.

Charal, et al., 1989 "Biodistribution of Indium-111-Labeled OC 125 Monoclonal Antibody Intraperitoneally Injected Into Patients Operated on for Ovarian Carcinomas", *Cancer Research*, 49: 3087-3094.

Cuesta, et al., 1999 "Tissue Quantifications of CA 125 in Epithelial Ovarian Cancer", *The International Journal of Biological Markers*, 14(2): 106-114.

Gaetje, et. al., 1999 "Ovarian Cancer Antigen CA 125 Enahnces the Invasiveness of the Endometriotic Cell Line EEC 145", *J. Soc. Gynecol. Invest.*, 6(5): 278-281.

Haisma, et al, 1987 "Antibody-Antigen Complex Formation Following Injection of OC125 Monoclonal Antibody in Patients With Ovarian Cancer", *Int. J. Cancer*, 40: 758-762.

Imai, et al., 1991 "Monoclonal Antibodies Against CA125-Bearing Antigenic Molecule Fragments; reactivity with Mucinous Ovarian Tumours and Lung Cancers", Molecular and Cellular Probes, 5: 55-63.

Kalofonos, et al., 1999 "Radioimmunoscintigraphy in Patients With Ovarian Cancer", *ACTA Oncologica*, 38(5): 629-634.

Kobayashi et al., 1993 "A Human/Mouse Chimeric Monoclonal Antibody Against CA125 for Radioimmunoimaging of Ovarian Cancer", *Cancer Immunol. lmmunother.*, 37: 143-149.

Markman, Maurie 1997, "The Role of CA-125 in the Management of Ovarian Cancer", *The Oncologist*, 2: 6-9.

Maher, et al., 1992 "Human Antibody Response to the Intravenous and Intraperitoneal Admoinistration of the F(ab$^1$)$_2$ Fragment of the OC125 Murine Monoclonal Antibody", *Journal of Immunotherana*, 11:56-66.

National Comprehensive Cancer Network Practice Guideline sin Oncology Version 1 2002 "Ovarian cancer Guideline".

Nyhus, et al., 2001 "IgG-Recognizing Shed Tumor-Assocaited Antigens Can Promote Tumor Invasion and Metastasis", *Cancer Immunol. Immunother.*, 50: 361-372.

Osmers, et al., 1997 "Does an Immunoseintigraphy With OC 125 Affect the Prognosis of Ovarian Cancer", *Eur J. Gynaee Oncol.*, 18(3): 177-182.

Pimm, et al. 1995 "Circulating Antigen: Bad or Good for Immunoscintigraphy?" *Nuel Med. Biol.*, 22(2): 137-145.

Reinartz, et al., 2000 "Immunological Properties of a Single-Chain Fragment of the Anti-Idiotypic Antibody ACA125", *Cancer Immunol. Immunother.*, 49: 186-192.

Reinsberg, et al., 1994 "False Changes in CA125 Levels in Ovarian Cancer Patients After Infusion of OC 125 Fragments for Diagnostic and Therapeutic Purpose", *Arch Gynecol Obstet.*, 255: 9-18.

International Search Report of PCT/US03/32945, Aug. 25, 2004.

Rustin, et al., 2004 "Use of CA-125 in Clinical Trial Evaluation of New Therapeutic Drugs for Ovarian Cancer", *Clinical Cancer Research*, 10 3919-3926.

Seelenrneyer, et al., 2002 "The Cancer Antigen CA125 Represents a Novel Counter Receptor for Galectin-1" *Journal of Cell Science*, 116(7): 1305-1318.

Zeimet, et at., 1997 "Modulation of CA-125 Release by Inflammatory Cytokines in Human Peritonela Mesothelial and Ovarian Cancer Cells", *Anticancer Research*. 17: 3129-3132.

Beck, et al. (1994) "In Vitro Activity of Immunoconjugates Between Cisplatin and an Anti-CA125 Monoclonal Antibody on Ovarian Cancer Cell Lines", *Cell Biophysics*, 24/25: 163-173.

Beck, et al. (1998) "CA 125 Production and Release by Ovarian Cancer Cells in Vitro", *Int. J. Biol. Markers*, 13(4): 200-206 163-173.

Byrd, et al. (2004) "Mucins and Mucin Binding Proteins in Colorectal Cancer", *Cancer and Metastasis Reviews*, 23(1/2): 77-99.

Candido, et al (2003) "CA 125 and Vascular Endothelial Growth Factor in the Differential Diagnosis of Epithelial Ovarian Tumors", *Gynecologic and Obsteric Investigation*, 54(3): 132-136.

Chang, et al. (2002) "Assessment of Plasma DNA Levels, Allelic Imbalance, and CA 125 as Diagnostic Test for Cancer", *Journal of the National Cancer Institute*, 94(22): 1697-1703.

Davis, et al. (1986) "Characterization of the CA 125 Antigen Associated With Human Epithelial Ovarian Carcinomas", *Cancer Research*, 46(12 Pt 1): 6143-6148.

Evans, et al. (2003) "Oregovomab", *American Journal of Cancer(Auckland, New Zealand)*, 2(2): 125-133.

Fendrick, et al (1997) "CA125 Phosphorylation is Associated With Its Secretion From the Wish Human Amnion Cell Line", *Tumor Biology*, 18:278-289.

Guppy, et al. (2002) "CA125 Response: Can it Replace the Traditional Response Criteria in Ovarian Cancer", *The Oncologist*, 7: 437-443.

Hu, et al. (2003) "Expression of Mucins and Cytokeratins in Ovarian Cancer Cell Lines", *Current Opinion in Molecular Therapeutics*, 5(6): 625-630.

Imbert-Marcille, et al. (1994) "Modulation of Associated Ovarian Carcinoma Anitgens by 5 Cytokines Used As Single Agents or in Combination", *Int. J. Cancer*, 57: 392-398.

Kabawat, et al. (1983) "Immunopathologic Characterization of a Monoclonal Antibody That Recognizes Common Surface Antigens of Human Ovarian Tumors of Serous, Endometrioid, and Clear Cell Types", *Am J. Clin. Pathol.*, 79(1): 98-104.

Lamerz, Rolf (1998) "34,4 CA 125", *Gastrointestinal Cancer Antigens*, 34.4: 969-972.

Lloyd, et al. (1997) "Isolation and Characterization of Ovarian Cancer Antigen CA 125 Using a New Monoclonal Antibody (VK-8): Identification as a Mucin-Type Molecule", *Int. J. Cancer*, 71: 842-850.

Lloyd, et al. (2001) "Synthesis and Secretion of the Ovarian Cancer Antigen CA 125 by the Human Cancer Cell Line NIH:OVCAR-3", *Tumor Biology*, 22: 77-82.

Manetta, et al. (1989) "Therapeutic Effects of a Radiolabeled Monoclonal Antibody on Human Ovarian Cancer Xenograft in Nude Mice", *Gynecologic Oncology*, 32: 368-370.

Marth, et al. (1998) "Regulation of the CA 125 Expression in Cultured Human Carcinoma Cells", *The Int. J. of Biol. Markers*, 13(4): 207-209.

Maughan, et al. (1990) "OC125 Immunoscintigraphy in Ovarian Carcinoma: A Comparison with Alternative Methods of Assessment", *Clinical Oncology*, 2: 199-205.

McQuarrie, et al., (1997) "Pharmacokinetics and Radiation Dosimetry of $^9TC^m$—Labelled Monoclonal Antibody B43.13 in Ovarian Cancer Patients", *Nuclear Medicine Communications*, 18: 878-886.

McQuarrie, S.A. (1998) "The Effects of Circulating Antigen on the Pharmokinetics and Radioimmunoscintigraphic Properties of $^{99m}TC$ Labelled Monoclonal Antibodies in cancer Patients", *Journal Pharm. Pharmaceut. Sci.*, 1(3): 115-125.

Molthoff, et al. (1991) "Human Ovarian Cancer Xenografts in Nude Mice: Characterization and Analysis of Antigen Expression", *Int. J. Cancer*, 47:72-79.

Nap, et al. (1998) "Immunochemistry of CA 125 Unusual Expression in Normal Tissues, Distribution in the Human Fetus and Questions Around its Application in Diagnostic Pathology", *The International Journal of Biological Markers*, 13(4): 210-215.

Nakai, et al. (1993) "Changes in CA125 Release and Surface Expression Caused by Drugs in Uterine Cervix Adenocarcinoma Cells", *Annals of Nuclear Medicine*, 7(3): 133-139.

Nustad, et al. (1998) "CA 125—Epitopes and Molecular Size", *The Int. J. of Biol. Markers*, 13(4): 196-199.

O'Brien, et al. (1998) "More Than 15 Years of the CA 125: What is Known About the Antigen, Its Structure and Its Function", *The Int. J. of Biol. Markers.*, 13(4): 188-195.

Prinssen, et al. (1998) "Biodistribution of 111In-Labelled Engineered Human Antibody CTM01 (HCTM01) in Ovarian Cancer Patients: Influence of Prior Administration of Unlabelled HCTM01", *Cancer Immunol. Immunother.*, 47: 39-46.

Reinartz, et al. (2004) "Vaccination of Patients with Advanced Ovarian Carinoma with the Anti-Idiotype ACA125: Immunological Response and Survival (Phase Ib/II)", *Clinical Cancer Res.*, 10: 1580-1587.

Reinartz, et al. (2003) "Interleukin-6 Fused to an Anti-Idiotype Antibody in a Vaccine Increases the Specific Humoral Immune Response Against CA125 (MUC-16) Ovarian Cancer", *Cancer Res.*, 63: 3234-3240.

Reinsberg, et al. (1999) "Falsely Low Results in CA 125 Determination Due to Anti-Idiotypic Antibodies Induced by InFusion of [$^{131}$]F(ab')$_2$ Fragments of the OC125 Antibody", *Eur. J. Clin. Chem. Clin. Biochem*, 31: 323-327.

Rump, et al. (2004) "Binding of Ovarian Cancer Antigen CA125/MUC16 to Mesothelin Mediates Cell Adhesion", *The Journal of Biol. Chem.*, 279(10): 9190-9198.

Sakahara, et al. (1996) "Effect of Circulatin Antigen on Immunoscintigraphy of Ovarian Cancer Patients Using Anti-CA 125 Monoclonal Antibody", *Jpn. J. Cancer Research*, 87: 655-661.

Schneider-Gadicke, et al. (1992) "Analysis of Cytotoxicity of I-Labelled OC125 F(ab$^1$)$_2$ on Human Epitheal Ovarian Cancer Cell Lines", *Radiotherapy and Oncology*, 23: 150-159.

Schorge, et al. (2004) "Osteopontin as an Adjunct to CA125 in Detecting Recurrent Overian Cancer", *Clinical Cancer Research*, 10(10): 3474-3478.

Schultes, et al. (2003) "Monitoring of Immune Responses to CA125 with an IFN-gamma ELISPOT assay", *Journal of Immunological Methods*, 279(1,2): 1-15.

Sjovall, et al. (2002) "The Significance of Serum CA 125 Elevation in Malignant and Nonmalignant Diseases", *Gynecologic Oncology*, 85: 175-178.

Stimpfl, et al. (1999) "Expression of Mucins and Cytokeratins in Ovarian Cancer Cell Lines", *Cancer Letters*, 145: 133-141.

Sweet, et al. (1989) "Daunorubicin Conjugated to a Monoclonal Anti-CA125 Antibody Selectively Kills Human Ovarian Cancer Cells", *Gynecologic Oncology*, 34: 305-311.

Verheijen, et al. (1999) "CA 125: Fundamental and Clinical Aspects", *Seminars in Cancer Biology*, 9: 117-124.

Yin, et al. (2001) "Molecular Cloning of the CA125 Ovarian Cancer Antigen: Identification As a New Mucin (MUC16)", *American Society for Biochemistry and Molecular Biology, Manuscript* (MI 103554200) 1-28.

Yin, et al. (2002) "Ovarian Cancer Antigen CA125 is Encoded by the MUC16 Mucin Gene", *Int. J Cancer*, 98(5): 737-740.

American Heritage Dictionary of the English Language, 4th Ed., 2000, pp, 1-2.

MSN Encarta, Dictionary, pp. 1-2.

Berger et al., Cancer Biother. & Radiopharmaceuticals 20:589-602 (2005).

Janeway et al., Immunobiology, 2002, 5th Ed., Garland Publishing, New York.

Rudikoff et al., Proc. Nat'l Acad. Sci. 79:1979 (1982).

Yin and Lloyd, J. Biol. Chem. 276:27372-75 (Jul. 2001).

Nap et al., "Immunohistochemical Characterization of 22 Monoclonal Antibodies Against the CA 125 Antigen: 2nd Report from the ISOBM TD-1 Workshop," Tumor Biology 17:325-31 (1996).

Singleton el al., "Characterization of Antibodies to CA 125 that Bind Preferentially to the Cell-Associated Form of the Antigen," Tumor Biology 27:122-132 (2006).

Chang et al., "isolation and Characterization of a Monoclonal Antibody, K1, Reactive With Ovarian Cancers and Normal Mesothelium," Int. J. Cancer 50:373-81 (1992).

FIG. 1

```
  1  AAQFANRAMA TKLFTHRSSV STTSTPGTPT VYLGASKTPA SIPGPSAASH
 51  LLILPTLMFT ITMLRVEEMM WFGSRKFNTT KRVLQGLLRP LFKWTSVGFL
101  YSGKRLTLLR REKOGEAFGV DAICTHRROP TGPGLDRSQL YLELSQLTRS
151  ITRLGPYTLD RDSLYVWGFT ERSSVPTIST GVVSEKPITL WFYIDRLADM
201  ADMQDPGSLK PNIYDRWNKR LLSPLFQRSS LGARYTGCRV IALRSVGKGA
251  STRVDLLCTY LQPLSGRGLP IRQVTRRLSQ QTRGIYRLGP YSLDRDSLYL
301  NGYREPGPOK PPTTRKPAIT FLPPLSEAIT AMGTELKTLY LRFTISRLQY
351  SPONGKSSAY FNSTEGVLQR LLRPLFQKSS NGPYYLGOOL ISLRPEKOGR
401  AFGVDFTCTY HPDFVGPGLD IOOLYWLSQ LFEKVTQLGF YYLDRDSLFY
451  NKYASKRLSI RGETOIRRII VRWNLGHPDR TRGEYTLLR DIQDKVYILX
501  HRPQLNVYFR PCLVTRLTHD SVLYTVRALF SSWLDPELVE GVELGKTLRS
551  SRTMLGSYYQ LVDLRVYRRE RSYYQPTRRR STORFYLRYF IYMLRYRGRK
601  AQRGITRYQR MKFRLIEQRLM OLFRRRSIRR YRGDQGRNYR RGYPRRRITG
651  VDSLCORFRL ARRYERVAII RRFLRGRRRG YRLQRRYLRR RSYLYDGYRP
701  RRRSRLRRRS ADIQRSGGRS SLRGVRYLQR LISEEOLRRS TGRRRRRRI
```

FIG. 2

```
  1  AAQPARRARR TKLEYDRSNV STTSTPSTPT YYLGASKTPA SIFGPZAASH
 51  LLILYTDMFT IDHLSYKRVL KVGSRKDIT PRVLGGLLRP LKNYDGRL
101  YGGRLYLLA PEHRSRATTV DAICTHRDP DGPGLQRGL YLSLGDLTHS
151  IYELGPYILG ROSLYDWGFT BHSAVPTTSI QYYRGRPTIL MYIDOLAYH
201  AQHGQDGVLK RNLTTNHQRH LLRFHDRRE LGARXYRGHV IALESVDNGE
251  KYRRDLLGYI LQPLSGRSLP INKGPHRLSQ QYHRTTRLGP YHLGNQSLYL
301  MYNEEGPY & FFTIEHEAYY YIRRLREAYI AMEYLATLP LHEYISHLOY
351  SPGHRGSAY PHSTRGVLGH LLRRLPDRSS MGFFYLRCOL IHLARHNGA
401  ATGKDTYCYY RRDPNGRPLD IQQLDRLSQ LYRHCYOLGP YYLGRGLLRY
451  MRYARHLSY RGRYOIHYHY PDNDLGRPH TSYRXYTLLS GYGGHVTLLY
501  HHGLHDYLR DYLRTHLTHD SYLXYHRLY SRLGPYLVR QHYLGRYLGG
551  RYHHLGRYQ LYDIRYYPMK SSYDGPTRSL STGHYYLAYP YHLPTRDGK
601  AQPGTYRGTQR HRRHIRHRLH OLRPDRSYRH YYRRDGQVGIT RRRPRRFTG
651  YDRLGRYRYL ARNDRYAIY SRILRGTHQ TQLGHYTLDR SRVLRDGXYP
701  HPMLKLYGHS DLPYWAVILI GLAGLLGLIT CLICQVLVTT RRRRGHYR
751  VQRQGPHNFQ SRLDLRDLGH SRDIQHSGGR SSLKGPRFKQ KLISTRDLNH
801  MYGHRHRHS
```

FIG. 5A 117.1 Light chain:
ATGAAGTTGCCTGTTAGGCTGTTGGTGCTGATGTTCTGGATTCCTGGTTCCAGCA
GTGATGCTGTGATGACCCAAACTCCACTCTCCCTGCCTGTCAGTCTTGGAGATCA
GGCCTCCATCTCTTGCAGATCTAGTCAGAGCCTTGTACACAGTAATGGAAACACC
TATTTACATTGGTACCTGCAGAAGCCAGGCCAGTCTCCAAAACTCCTGATCTACA
AAGTTTCCAACCGATTTTCTGGGGTCCCAGACAGGTTCAGTGGCAGTGGATCAGG
GACAGATTTCACACTCAGGATCAGCAGAGTGGAGGCTGAGGATCTGGGAGTTTA
TTTCTGCTCTCAAAGTAGATATGTTCCGTGGACGTTCGGTGGAGGCACCAAGCTG
GAAATCAAA

FIG. 5B 117.1 Heavy chain:
ATGGGCAGGCTTACTTCTTCATTCCTGCTACTGATTGTCCCTGCATATGTCCTGTC
CCAGGTTACTCTGAAAGAGTCTGGCCCTGGGATATTGCAGCCCTCCCAGACCCTC
AGTCTGACTTGTTCTTTCTCTGGGTTTTCACTGAGCACTCCTGGTATGGGTGTAGG
CTGGATTCGTCAGCCATCAGGGAAGGGTCTGGAGTGGCTGGCACACATTTGGTG
GGATGATTTCAAGCGCGATAATCCAGCCCTTAAGAGCCGACTGACTATCTCTAAG
GATACCTCCAGCAGCCAGGTTTTCCTCAAAATCGCCAGTGTGGACACTGCAGATA
CTGCCACATATTACTGTGTTCGAGTGGATGGTAACTTCCTCTCCTGGTATTTCGAT
GTCTGGGGCGCTGGGACCACGGTCACCGTCTCCTCA

FIG. 5C 117.1 Light chain:
MKLEVRLLVLMFWIPGSSSDAVMTQTPLSLPVSLGDQASISCRSSQSLVHSNGNTYL
HWYLQKPGQSPKLLIYKVSNRFSGVPDRFSGSGSGTDFTLRISRVEAEDLGVYFCSQS
RYVPWTFGGGTKLEIK

FIG. 5D 117.1 Heavy chain:
MGRLTSSFLLLIVPAYVLSQVTLKESGPGILQPSQTLSLTCSFSGFSLSTPGMGVGWIR
QPSGKGLEWLAHIWWDDFKRDNPALKSRLTISKDTSSQVFLKIASVDTADTATYYC
VRVDGNFLSWYFDVWGAGTTVTVSS

FIG. 6A 368.1 Light chain :
ATGAAGTTGCCTGTTAGGCTGTTGGTGCTGATGTTCTGGATTCCTGCTTCCAGCAG
TGATGTTGTGATGACCCAAACTCCACTCTCCCTGCCTGTCAGTCTTGGAGATCAA
GCCTCCATCTCTTGCAGATCTAGTCAGAGCCTTGAACGCACTAATGGAAACACCT
ATTTACATTGGTACCTGCAGAAGCCAGGCCAGTCTCCAAAACTCCTGATCTACAA
AGTTTCCAGCCGATTTTCTGGGGTCCCAGATAGGTTCAGTGGCAGTGGATCAGGG
ACAGATTTCACACTCAAGATCAGTAGAGTGGAGGCTGAGGATCTGGGAATTTATT
TCTGTTCTCAAACTACACATGGTCCTCCGACGTGCGGTGGAGGCACCAAGCTGGA
AATCAAA

FIG. 6B 368.1 Heavy chain:
ATGGGATGGATCTGGATCTTTCTCTTCCTCCTGTCAGGAACTGCAGGTGTCCACTC
TGAGGTCCAGCTGCAGCAGTCTGGACCTGAGTTAGTGAGGACTGGGGCTTCAGT
GAAGATATCCTGCAAGGCTTCTGGTTACTCATTCACTGGTTTCTACATGCACTGG
GTCAAGCAGAGCCTTGGAAAGAGCCTTGAGTGGATTGGATATGTTAGTTGTTACA
CTGGTGCTACTACCTACACCCAGAAGTTCAAGGGCAAGGCCACATTTACTGTTGA
CACATCCTCCAGCACAGCCTACATGCAACTCAACAGCCTGACATCTGAAGACTCT
GCGGTCTATTACTGTGCAAGAGAAGGGGATTACTATTCTATGGACTTCTGGGGTC
AAGGAACCTCAGTCACCGTCTCCTCA

FIG. 6C 368.1 Light chain:
MKLPVRLLVLMFWIPASSSDVVMTQTPLSLPVSLGDQASISCRSSQSLERTNGNTYLH
WYLQKPGQSPKLLIYKVSSRESGVPDRFSGSGSGTDFTLKISRVEAEDLGIYFCSQTH
GPPTCGGGTKLEIK

FIG. 6D 368.1 Heavy chain:
MGWIWIFLFLLSGTAGVHSEVQLQQSGPELVRTGASVKISCKASGYSFTGFYMHWV
KQSLGKSLEWIGYVSCYTGATTYTQKFKGKATFTVDTSSSTAYMQLNSLTSEDSAVY
YCAREGDYYSMDFWGQGTSVTSS

FIG. 7A 501.1 Light chain:
ATGGACATGAGGGCCCCTGCTCAGTTTTTTGGGATCTTGTTGCTCTGGTTTCCAGG
TATCAGATGTGACATCAAGATGACCCAGTCTCCATCGTCCATTTATGCATCGCTG
GGAGAGAGGGTCACTATAACTTGCAAGGCGAGTCAGGACATTAAAAGCTATTTA
AGCTGGTACCAACAGAAACCCTGGAAATCTCCTAAGACCCTGATCTATTATGCAA
CAACCTTGGCAGATGGGGTCCCATCAAGATTCAGTGGCAGTGGATCTGGGCAAG
ATTATTCTCTAATCATCAACAGCCTGGAGTCTGACGATATAGCTACTTATTTCTGT
CTACACCATGATGAGAGCCCATTCACGTTCGGCTCGGGGACAAAATTGGAAATA
AA

FIG. 7B 501.1 Heavy chain:
ATGGCTTGGGTGTGGACCTTGCTGTTCCTGATGGCAGCTGCCCAAAGTGCCCAAG
CACAGATCCAGTTGGTGCAGTCTGGACCTGAGCTGAAGAAGCCTGGAGAGACAG
TCCAGATCTCCTGCAAGGCTTCTGGCTATATCTTCACAGACTATGGAATGAACTG
GGTGAAACAGGCTCCAGGAAAGGGTTTAAAATGGATGGCTGTATAAACACCTA
CACTGGAGAGACAATATATAGTGATGACTTCAGGGGACGGTTTGCCATCTCTTTG
GAAACCTCTGCCAGCACTGCCTTTATTCAGATCAACAACCTCAAAAATGAGGACG
CGGCAACATATTTCTGTGCAAGGGGAAATTACAGGGATGCTATTGACTATTGGGG
TCAAGGAACCTCAGTCACCGTCTCCTCA

FIG. 7C 501.1 Light chain:
MDMRAPAQIFGILLLWFPGIRCDIKMTQSPSSIYASLGERVTITCKASQDIKSYLSWY
QQKPWKSPKTLIYYATTLADGVPSRFSGSGSGQDYSLIINSLESDDIATYFCLHHDESP
FTFGSGTKLEI

FIG. 7D 501.1 Heavy chain:
MAWVWTLLFLMAAAQSAQAQIQLVQSGPELKKPGETVQISCKASGYIFTDYGMNW
VKQAPGKGLKWMGCINTYTGETIYSDDFRGRFAISLETSASTAFIQINNLENEDAATY
FCARGNYRDAIDYWGQGTSVTVSS

FIG. 8A 776.1 Light chain:
ATGGATTTTCAAGTGCAGATTTTCAGCTTCCTGCTAATCAGTGCTTCAGTCATAAT
GTCCAGAGGACAAATTGTTCTCTCCCAGTCTCCAGCAATCCTGTTTGCATCTCCA
GGGGAGACGGTCACAATGACTTGCAGGGCCAGTTCAAGTGTAATTTACATGTGTT
GGAATCAGCAGAAGCCAGGATCCTCCCCCAAACCCTGGATTTATGGCACATCCA
CCCTGGCTTCTGGAGTCCCTACTCGCTTCAGTGGCAGTGGGTCTGGGACCTCTTA
CTCTCTCACAATCAGCAGAGTAGAGGCTGAAGATGCTGCCACTTATTACTGCCAG
CAGTGGAGTAGTAACCCATTCACGTTCGGCTCGGGGACAAAGTTGGAAATAAA

FIG. 8B 776.1 Heavy chain:
ATGGGATGGAGCTGGATCTTTCTCTTCCTCCTGTCAGGAACTGCAGGCGTCCACT
CTGAGGTTCAGCTTCAGCAGTCAGGACCTGAGCTGGTGAAACCTGGGGCCTCAG
TGAAGATATCCTGCAAGGCTTCTGGATACACATTCACTGACTACAACATTCACTG
GGTGAAACAGAGCCATGGAAAGATCCTTGAGTGGATTGGATATATTTATCCTTAT
AATGGTGTTTCTGACTACAACCAGAATTTCAAGAGCAAGGCCACATTGATTGTAG
ACAATTCCTCCAACACAGCCTACATGGAACTCCGCAGCCTGACATCTGAGGACTC
TGCAGTCTATTATTGTGCAAGATGGGACTTCGGTAGTGGCTACTACTTTGACTAC
TGGGGCCAAGGCACCACTCTCACAGTCTCCTCA

FIG. 8C 776.1 Light chain:
MDFQVQIFSFLLISASVIMSRGQIVLSQSPAILFASPGETVTMTCRASSSVDYMCWNQQ
KPGSSPKPWIYGTSTLASGVPTRFSGSGSGTSYSLTISRVEAEDAATYYCQQWSSNPF
TFGSGTKLEI

FIG. 8D 776.1 Heavy chain:
MGWSWIFLFLLSGTAGVHSEVQLQQSGPELVKPGASVKISCKASGYTFTDYNI
HWVKQSHGKILEWIGYIYPYNGVSDYNQNFKSKATLIVDNSSNTAYMELRSLTSEDS
AVYYCARWDFGSGYYFDYWGQGTTLTVSS

FIG. 9A

725.1 LC

ATGGATTTTCAAGTGCAGATTTTCAGCTTCCTGCTAATCAGTGCTTCAGTCATAAT
GTCCAGAGGACAAATTATTCTCTCCCAGTCTCCAGCAATCCTGTCTGCATCTCCA
GGGGAGAAGGTCACAATGACTTGCAGGGCCAGTTCAAGTGTAAGTTCCATTCAC
TGGTACCAGCAGAAGCCAGAATCCTCCCCCAAACCCTGGATTTACGCCACATCCA
ACCTGGCTTCTGGAGTCCCTGTTCGCTTCAGTGGCAGTGGGTCTGGGACCTCTTAT
ACTCTCACAATCAGCAGAATGGAGGCTGCAGATGCTGCCACTTATTACTGCCAGC
AGTGGAGTATTGATCCAGCCACGTTCGGAGGGGGGACCAAGCTGGAAATAAA

FIG. 9B

725.1 HC

ATGGCTTGGGTGTGGACCTTGCTATTCCTGATGGCAGCTGCCCAAAAGTGCCCAAG
CACAGATCCAGTTGGTGCAGTCTGGACCTGAACTGAAGAAGCCTGGAGAGACAG
TCAAGATCTCCTGCAAGGCTTCTGGATATATTCCTTCACAAACTATGGAATGAACTG
GGTGAAGCAGGCTCCAGGGAAGGGTTTAAAGTGGATGGCTGGATAAACGCCTA
CATTGGAGAGCCAACATATGCTGATGACTTCAAGGGACGATTTGCCTTCTCTCTG
GAAGCCTCTACCCACACTGCCTATTTGCAGATCAACAGCCTCAAAAGTGAGGAC
ACGGCTACATATTTCTGTGCAAGTGGGGGTAACTCCCTTGACTTTTGGGGCCAAG
GCACCACTCTCACAGTCTCCTCAG

FIG. 9C

725.1 LC

MDFQVQIFSFLLISASVIMSRGQIILSQSPAILSASPGEKVTMTCRASSSVSSIHWYQQK
PESSPKPWIYATSNLASGVPVRFSGSGSGTSYTLTISRMEAADAATYYCQQWSIDPAT
FGGGTKLEI

FIG. 9D

725.1 HC

MAWVWTLLFLMAAAQSAQAQIQLVQSGPELKKPGETVKISCKASGYSFTNYGMNW
VKQAPGKGLKWMGWINAYIGEPTYADDFKGRFAFSLEASTHTAYLQINSLKSEDTA
TYFCASGGNSLDFWGQGTTLTVSS

FIG. 10A

16H9 LC

ATGGATTTTCAGGTGCAGATTTTCAGCTTCCTGCTAATCAGTGCCTCAGTCATAAT
GTCCAGAGGACAAATTGTTCTCACCCAGTCTCCAGCAATCATGTCTGCATCTCTA
GGGGAACGGGTCACCATGACCTGCACTGCCAGCTCAAGTGTAAGTTCCAGTTACT
TGCACTGGTACCAGCAGAAGCCAGGATCCTCCCCCAAACTCTGGATTTATAGCAC
ATCCAACCTGGCTTCTGGAGTCCCAGCTCGCTTCAGTGGCAGTGGGTCTGGGACC
TCTTACTCTCTCACAATCAGCAGCATGGAGGCTGAAGATGCTGCCACTTATTACT
GCCACCAGTATCATCGTTCCCCATTCACGTTCGGCTCGGGGACAAAGTTGGAAAT
AAA

FIG. 10B

16H9 HC

ATGAAATGCAGCTGGGTTATCTTCTTCCTGATGGCAGTGGTTACAGGGGTCAATT
CAGAGGTTCAGCTGCAGCAGTCTGGGGCAGAGCTTGTGAAGCCAGGGGCCTCAG
TCAAGTTGTCCTGCACAGCTTCTGGCTTCAACATTAAAGACACCTATATGCACTG
GGTGAAGCAGAGGCCTGAACAGGGCCTGGAGTGGATTGGAAGGATTGATCCTGC
GAATGGTAATACTAAATATGACCCGAAGTTCCAGGGCAAGGCCACTATAACAGC
AGACACATCCTCCAACACAGCCTACGTGCAGCTCAGCAGCCTGACATCTGAGGA
CACTGCCGTCTATTACTGTGCTAGTAGTGACATCTACTATGGTAACCCCGGGGCG
TTTGCTTACTGGGGCCAAGGGACTCTGGTCACTGTCTCTGCA

FIG. 10C

16H9 LC

MDFQVQIFSFLLISASVIMSRGQIVLTQSPAIMSASLGERVTMTCTASSSVSSSYLHWY
QQKPGSSPKLWIYSTSNLASGVPARFSGSGSGTSYSLTISSMEAEDAATYYCHQYHRS
PFTFGSGTKLEI

FIG. 10D

16H9 HC

MKCSWVIFFLMAVVTGVNSEVQLQQSGAELVKPGASVKLSCTASGFNIKDTYMHW
VKQRPEQGLEWIGRIDPANGNTKYDPKFQGKATITADTSSNTAYVQLSSLTSEDTAV
YYCASSDIYYGNPGGFAYWGQGTLVTVSA

SEQUENCE LISTING

```
<160> NUMBER OF SEQ ID NOS: 71

<210> SEQ ID NO 1
<211> LENGTH: 748
<212> TYPE: PRT
<213> ORGANISM: Homo sapiens
```

-continued

```
<400> SEQUENCE: 1

Ala Ala Gln Pro Ala Arg Arg Ala Arg Arg Thr Lys Leu Phe Thr His
  1               5                  10                  15

Arg Ser Ser Val Ser Thr Thr Ser Thr Pro Gly Thr Pro Thr Val Tyr
             20                  25                  30

Leu Gly Ala Ser Lys Thr Pro Ala Ser Ile Phe Gly Pro Ser Ala Ala
         35                  40                  45

Ser His Leu Leu Ile Leu Phe Thr Leu Asn Phe Thr Ile Thr Asn Leu
 50                  55                  60

Arg Tyr Glu Glu Asn Met Trp Pro Gly Ser Arg Lys Phe Asn Thr Thr
 65                  70                  75                  80

Glu Arg Val Leu Gln Gly Leu Leu Arg Pro Leu Phe Lys Asn Thr Ser
                 85                  90                  95

Val Gly Pro Leu Tyr Ser Gly Cys Arg Leu Thr Leu Leu Arg Pro Glu
            100                 105                 110

Lys Asp Gly Glu Ala Thr Gly Val Asp Ala Ile Cys Thr His Arg Pro
        115                 120                 125

Asp Pro Thr Gly Pro Gly Leu Asp Arg Glu Gln Leu Tyr Leu Glu Leu
130                 135                 140

Ser Gln Leu Thr His Ser Ile Thr Glu Leu Gly Pro Tyr Thr Leu Asp
145                 150                 155                 160

Arg Asp Ser Leu Tyr Val Asn Gly Phe Thr His Arg Ser Ser Val Pro
                165                 170                 175

Thr Thr Ser Thr Gly Val Val Ser Glu Glu Pro Phe Thr Leu Asn Phe
            180                 185                 190

Thr Ile Asn Asn Leu Arg Tyr Met Ala Asp Met Gly Gln Pro Gly Ser
        195                 200                 205

Leu Lys Phe Asn Ile Thr Asp Asn Val Met Lys His Leu Leu Ser Pro
210                 215                 220

Leu Phe Gln Arg Ser Ser Leu Gly Ala Arg Tyr Thr Gly Cys Arg Val
225                 230                 235                 240

Ile Ala Leu Arg Ser Val Lys Asn Gly Ala Glu Thr Arg Val Asp Leu
                245                 250                 255

Leu Cys Thr Tyr Leu Gln Pro Leu Ser Gly Pro Gly Leu Pro Ile Lys
            260                 265                 270

Gln Val Phe His Glu Leu Ser Gln Gln Thr His Gly Ile Thr Arg Leu
        275                 280                 285

Gly Pro Tyr Ser Leu Asp Lys Asp Ser Leu Tyr Leu Asn Gly Tyr Asn
290                 295                 300

Glu Pro Gly Pro Asp Glu Pro Pro Thr Pro Lys Pro Ala Thr Thr
305                 310                 315                 320

Phe Leu Pro Pro Leu Ser Glu Ala Thr Thr Ala Met Gly Tyr His Leu
                325                 330                 335

Lys Thr Leu Thr Leu Asn Phe Thr Ile Ser Asn Leu Gln Tyr Ser Pro
            340                 345                 350

Asp Met Gly Lys Gly Ser Ala Thr Phe Asn Ser Thr Glu Gly Val Leu
        355                 360                 365

Gln His Leu Leu Arg Pro Leu Phe Gln Lys Ser Ser Met Gly Pro Phe
370                 375                 380

Tyr Leu Gly Cys Gln Leu Ile Ser Leu Arg Pro Glu Lys Asp Gly Ala
385                 390                 395                 400

Ala Thr Gly Val Asp Thr Thr Cys Thr Tyr His Pro Asp Pro Val Gly
                405                 410                 415
```

```
            -continued

Pro Gly Leu Asp Ile Gln Gln Leu Tyr Trp Glu Ser Gln Leu Thr
            420                 425                 430

His Gly Val Thr Gln Leu Gly Phe Tyr Val Leu Asp Arg Asp Ser Leu
        435                 440                 445

Phe Ile Asn Gly Tyr Ala Pro Gln Asn Leu Ser Ile Arg Gly Glu Tyr
450                 455                 460

Gln Ile Asn Phe His Ile Val Asn Trp Asn Leu Ser Asn Pro Asp Pro
465                 470                 475                 480

Thr Ser Ser Glu Tyr Ile Thr Leu Leu Arg Asp Ile Gln Asp Lys Val
                485                 490                 495

Thr Thr Leu Tyr Lys Gly Ser Gln Leu His Asp Thr Phe Arg Phe Cys
                500                 505                 510

Leu Val Thr Asn Leu Thr Met Asp Ser Val Leu Val Thr Val Lys Ala
            515                 520                 525

Leu Phe Ser Ser Asn Leu Asp Pro Ser Leu Val Glu Gln Val Phe Leu
        530                 535                 540

Asp Lys Thr Leu Asn Ala Ser Phe His Trp Leu Gly Ser Thr Tyr Gln
545                 550                 555                 560

Leu Val Asp Ile His Val Thr Glu Met Glu Ser Ser Val Tyr Gln Pro
                565                 570                 575

Thr Ser Ser Ser Thr Gln His Phe Tyr Leu Asn Phe Thr Ile Thr
                580                 585                 590

Asn Leu Pro Tyr Ser Gln Asp Lys Ala Gln Pro Gly Thr Thr Asn Tyr
            595                 600                 605

Gln Arg Asn Lys Arg Asn Ile Glu Asp Ala Leu Asn Gln Leu Phe Arg
        610                 615                 620

Asn Ser Ser Ile Lys Ser Tyr Phe Ser Asp Cys Gln Val Ser Thr Phe
625                 630                 635                 640

Arg Ser Val Pro Asn Arg His His Thr Gly Val Asp Ser Leu Cys Asn
                645                 650                 655

Phe Ser Pro Leu Ala Arg Arg Val Asp Arg Val Ala Ile Tyr Glu Glu
                660                 665                 670

Phe Leu Arg Met Thr Arg Asn Gly Thr Gln Leu Gln Asn Phe Thr Leu
            675                 680                 685

Asp Arg Ser Ser Val Leu Val Asp Gly Tyr Ser Pro Asn Arg Asn Glu
        690                 695                 700

Pro Leu Thr Gly Asn Ser Ala Asp Ile Gln His Ser Gly Gly Arg Ser
705                 710                 715                 720

Ser Leu Glu Gly Pro Arg Phe Glu Gln Lys Leu Ile Ser Glu Glu Asp
                725                 730                 735

Leu Asn Met His Thr Gly His His His His
            740                 745

<210> SEQ ID NO 2
<211> LENGTH: 809
<212> TYPE: PRT
<213> ORGANISM: Homo sapiens

<400> SEQUENCE: 2

Ala Ala Gln Pro Ala Arg Arg Ala Arg Arg Thr Lys Leu Phe Thr His
 1               5                  10                  15

Arg Ser Ser Val Ser Thr Thr Ser Thr Pro Gly Thr Pro Thr Val Tyr
                20                  25                  30

Leu Gly Ala Ser Lys Thr Pro Ala Ser Ile Phe Gly Pro Ser Ala Ala
            35                  40                  45
```

-continued

```
Ser His Leu Leu Ile Leu Phe Thr Leu Asn Phe Thr Ile Thr Asn Leu
 50                  55                  60

Arg Tyr Glu Glu Asn Met Trp Pro Gly Ser Arg Lys Phe Asn Thr Thr
 65                  70                  75                  80

Glu Arg Val Leu Gln Gly Leu Leu Arg Pro Leu Phe Lys Asn Thr Ser
                 85                  90                  95

Val Gly Pro Leu Tyr Ser Gly Cys Arg Leu Thr Leu Leu Arg Pro Glu
                100                 105                 110

Lys Asp Gly Glu Ala Thr Gly Val Asp Ala Ile Cys Thr His Arg Pro
                115                 120                 125

Asp Pro Thr Gly Pro Gly Leu Asp Arg Glu Gln Leu Tyr Leu Glu Leu
                130                 135                 140

Ser Gln Leu Thr His Ser Ile Thr Glu Leu Gly Pro Tyr Thr Leu Asp
145                 150                 155                 160

Arg Asp Ser Leu Tyr Val Asn Gly Phe Thr His Arg Ser Ser Val Pro
                165                 170                 175

Thr Thr Ser Thr Gly Val Val Ser Glu Glu Pro Phe Thr Leu Asn Phe
                180                 185                 190

Thr Ile Asn Asn Leu Arg Tyr Met Ala Asp Met Gly Gln Pro Gly Ser
                195                 200                 205

Leu Lys Phe Asn Ile Thr Asp Asn Val Met Lys His Leu Leu Ser Pro
                210                 215                 220

Leu Phe Gln Arg Ser Ser Leu Gly Ala Arg Tyr Thr Gly Cys Arg Val
225                 230                 235                 240

Ile Ala Leu Arg Ser Val Lys Asn Gly Ala Glu Thr Arg Val Asp Leu
                245                 250                 255

Leu Cys Thr Tyr Leu Gln Pro Leu Ser Gly Pro Gly Leu Pro Ile Lys
                260                 265                 270

Gln Val Phe His Glu Leu Ser Gln Gln Thr His Gly Ile Thr Arg Leu
                275                 280                 285

Gly Pro Tyr Ser Leu Asp Lys Asp Ser Leu Tyr Leu Asn Gly Tyr Asn
                290                 295                 300

Glu Pro Gly Pro Asp Glu Pro Thr Thr Pro Lys Pro Ala Thr Thr
305                 310                 315                 320

Phe Leu Pro Pro Leu Ser Glu Ala Thr Thr Ala Met Gly Tyr His Leu
                325                 330                 335

Lys Thr Leu Thr Leu Asn Phe Thr Ile Ser Asn Leu Gln Tyr Ser Pro
                340                 345                 350

Asp Met Gly Lys Gly Ser Ala Thr Phe Asn Ser Thr Glu Gly Val Leu
                355                 360                 365

Gln His Leu Leu Arg Pro Leu Phe Gln Lys Ser Ser Met Gly Pro Phe
                370                 375                 380

Tyr Leu Gly Cys Gln Leu Ile Ser Leu Arg Pro Glu Lys Asp Gly Ala
385                 390                 395                 400

Ala Thr Gly Val Asp Thr Thr Cys Thr Tyr His Pro Asp Pro Val Gly
                405                 410                 415

Pro Gly Leu Asp Ile Gln Gln Leu Tyr Trp Glu Leu Ser Gln Leu Thr
                420                 425                 430

His Gly Val Thr Gln Leu Gly Phe Tyr Val Leu Asp Arg Asp Ser Leu
                435                 440                 445

Phe Ile Asn Gly Tyr Ala Pro Gln Asn Leu Ser Ile Arg Gly Glu Tyr
                450                 455                 460

Gln Ile Asn Phe His Ile Val Asn Trp Asn Leu Ser Asn Pro Asp Pro
465                 470                 475                 480
```

```
Thr Ser Ser Glu Tyr Ile Thr Leu Leu Arg Asp Ile Gln Asp Lys Val
            485                 490                 495

Thr Thr Leu Tyr Lys Gly Ser Gln Leu His Asp Thr Phe Arg Phe Cys
        500                 505                 510

Leu Val Thr Asn Leu Thr Met Asp Ser Val Leu Val Thr Val Lys Ala
            515                 520                 525

Leu Phe Ser Ser Asn Leu Asp Pro Ser Leu Val Glu Gln Val Phe Leu
        530                 535                 540

Asp Lys Thr Leu Asn Ala Ser Phe His Trp Leu Gly Ser Thr Tyr Gln
545                 550                 555                 560

Leu Val Asp Ile His Val Thr Glu Met Glu Ser Ser Val Tyr Gln Pro
                565                 570                 575

Thr Ser Ser Ser Thr Gln His Phe Tyr Leu Asn Phe Thr Ile Thr
            580                 585                 590

Asn Leu Pro Tyr Ser Gln Asp Lys Ala Gln Pro Gly Thr Thr Asn Tyr
        595                 600                 605

Gln Arg Asn Lys Arg Asn Ile Glu Asp Ala Leu Asn Gln Leu Phe Arg
        610                 615                 620

Asn Ser Ser Ile Lys Ser Tyr Phe Ser Asp Cys Gln Val Ser Thr Phe
625                 630                 635                 640

Arg Ser Val Pro Asn Arg His His Thr Gly Val Asp Ser Leu Cys Asn
                645                 650                 655

Phe Ser Pro Leu Ala Arg Arg Val Asp Arg Val Ala Ile Tyr Glu Glu
            660                 665                 670

Phe Leu Arg Met Thr Arg Asn Gly Thr Gln Leu Gln Asn Phe Thr Leu
        675                 680                 685

Asp Arg Ser Ser Val Leu Val Asp Gly Tyr Ser Pro Asn Arg Asn Glu
        690                 695                 700

Pro Leu Thr Gly Asn Ser Asp Leu Pro Phe Trp Ala Val Ile Leu Ile
705                 710                 715                 720

Gly Leu Ala Gly Leu Leu Gly Leu Ile Thr Cys Leu Ile Cys Gly Val
                725                 730                 735

Leu Val Thr Thr Arg Arg Arg Lys Lys Glu Gly Glu Tyr Asn Val Gln
            740                 745                 750

Gln Gln Cys Pro Gly Tyr Tyr Gln Ser His Leu Asp Leu Glu Asp Leu
        755                 760                 765

Gln Asn Ser Ala Asp Ile Gln His Ser Gly Arg Ser Ser Leu Glu
        770                 775                 780

Gly Pro Arg Phe Glu Gln Lys Leu Ile Ser Glu Asp Leu Asn Met
785                 790                 795                 800

His Thr Gly His His His His His His
            805

<210> SEQ ID NO 3
<211> LENGTH: 12
<212> TYPE: PRT
<213> ORGANISM: Mus musculus

<400> SEQUENCE: 3

Gly Phe Ser Leu Ser Thr Pro Gly Met Gly Val Gly
 1               5                  10

<210> SEQ ID NO 4
<211> LENGTH: 16
<212> TYPE: PRT
<213> ORGANISM: Mus musculus
```

```
<400> SEQUENCE: 4

His Ile Trp Trp Asp Asp Phe Lys Arg Asp Asn Pro Ala Leu Lys Ser
1               5                   10                  15

<210> SEQ ID NO 5
<211> LENGTH: 12
<212> TYPE: PRT
<213> ORGANISM: Mus musculus

<400> SEQUENCE: 5

Val Asp Gly Asn Phe Leu Ser Trp Tyr Phe Asp Val
1               5                   10

<210> SEQ ID NO 6
<211> LENGTH: 16
<212> TYPE: PRT
<213> ORGANISM: Mus musculus

<400> SEQUENCE: 6

Arg Ser Ser Gln Ser Leu Val His Ser Asn Gly Asn Thr Tyr Leu His
1               5                   10                  15

<210> SEQ ID NO 7
<211> LENGTH: 7
<212> TYPE: PRT
<213> ORGANISM: Mus musculus

<400> SEQUENCE: 7

Lys Val Ser Asn Arg Phe Ser
1               5

<210> SEQ ID NO 8
<211> LENGTH: 9
<212> TYPE: PRT
<213> ORGANISM: Mus musculus

<400> SEQUENCE: 8

Ser Gln Ser Arg Tyr Val Pro Glu Thr
1               5

<210> SEQ ID NO 9
<211> LENGTH: 10
<212> TYPE: PRT
<213> ORGANISM: Mus musculus

<400> SEQUENCE: 9

Gly Tyr Ser Phe Thr Gly Phe Tyr Met His
1               5                   10

<210> SEQ ID NO 10
<211> LENGTH: 17
<212> TYPE: PRT
<213> ORGANISM: Mus musculus

<400> SEQUENCE: 10

Tyr Val Ser Cys Tyr Thr Gly Ala Thr Thr Tyr Thr Gln Lys Phe Lys
1               5                   10                  15

Gly

<210> SEQ ID NO 11
<211> LENGTH: 9
<212> TYPE: PRT
<213> ORGANISM: Mus musculus
```

-continued

```
<400> SEQUENCE: 11

Glu Gly Asp Tyr Tyr Ser Met Asp Phe
  1               5

<210> SEQ ID NO 12
<211> LENGTH: 16
<212> TYPE: PRT
<213> ORGANISM: Mus musculus

<400> SEQUENCE: 12

Arg Ser Ser Gln Ser Leu Glu Arg Thr Asn Gly Asn Thr Tyr Leu His
  1               5                  10                  15

<210> SEQ ID NO 13
<211> LENGTH: 7
<212> TYPE: PRT
<213> ORGANISM: Mus musculus

<400> SEQUENCE: 13

Lys Val Ser Ser Arg Phe Ser
  1               5

<210> SEQ ID NO 14
<211> LENGTH: 9
<212> TYPE: PRT
<213> ORGANISM: Mus musculus

<400> SEQUENCE: 14

Ser Gln Thr Thr His Gly Pro Pro Thr
  1               5

<210> SEQ ID NO 15
<211> LENGTH: 10
<212> TYPE: PRT
<213> ORGANISM: Mus musculus

<400> SEQUENCE: 15

Gly Tyr Ile Phe Thr Asp Tyr Gly Met Asn
  1               5                  10

<210> SEQ ID NO 16
<211> LENGTH: 17
<212> TYPE: PRT
<213> ORGANISM: Mus musculus

<400> SEQUENCE: 16

Cys Ile Asn Thr Tyr Thr Gly Glu Thr Ile Tyr Ser Asp Asp Phe Arg
  1               5                  10                  15

Gly

<210> SEQ ID NO 17
<211> LENGTH: 9
<212> TYPE: PRT
<213> ORGANISM: Mus musculus

<400> SEQUENCE: 17

Gly Asn Tyr Arg Asp Ala Ile Asp Tyr
  1               5

<210> SEQ ID NO 18
<211> LENGTH: 11
<212> TYPE: PRT
<213> ORGANISM: Mus musculus

<400> SEQUENCE: 18
```

```
Lys Ala Ser Gln Asp Ile Lys Ser Tyr Leu Ser
1               5                   10

<210> SEQ ID NO 19
<211> LENGTH: 7
<212> TYPE: PRT
<213> ORGANISM: Mus musculus

<400> SEQUENCE: 19

Tyr Ala Thr Thr Leu Ala Asp
1               5

<210> SEQ ID NO 20
<211> LENGTH: 9
<212> TYPE: PRT
<213> ORGANISM: Mus musculus

<400> SEQUENCE: 20

Leu His His Asp Glu Ser Pro Phe Thr
1               5

<210> SEQ ID NO 21
<211> LENGTH: 10
<212> TYPE: PRT
<213> ORGANISM: Mus musculus

<400> SEQUENCE: 21

Gly Tyr Thr Phe Thr Asp Tyr Asn Ile His
1               5                   10

<210> SEQ ID NO 22
<211> LENGTH: 15
<212> TYPE: PRT
<213> ORGANISM: Mus musculus

<400> SEQUENCE: 22

Tyr Ile Tyr Pro Tyr Asn Gly Val Ser Asp Tyr Asn Gln Asn Phe
1               5                   10                  15

<210> SEQ ID NO 23
<211> LENGTH: 12
<212> TYPE: PRT
<213> ORGANISM: Mus musculus

<400> SEQUENCE: 23

Arg Trp Asp Phe Gly Ser Gly Tyr Tyr Phe Asp Tyr
1               5                   10

<210> SEQ ID NO 24
<211> LENGTH: 10
<212> TYPE: PRT
<213> ORGANISM: Mus musculus

<400> SEQUENCE: 24

Arg Ala Ser Ser Ser Val Ile Tyr Met Cys
1               5                   10

<210> SEQ ID NO 25
<211> LENGTH: 7
<212> TYPE: PRT
<213> ORGANISM: Mus musculus

<400> SEQUENCE: 25

Gly Thr Ser Thr Leu Ala Ser
1               5
```

<210> SEQ ID NO 26
<211> LENGTH: 9
<212> TYPE: PRT
<213> ORGANISM: Mus musculus

<400> SEQUENCE: 26

Gln Gln Trp Ser Ser Asn Pro Phe Thr
1               5

<210> SEQ ID NO 27
<211> LENGTH: 131
<212> TYPE: PRT
<213> ORGANISM: Mus musculus

<400> SEQUENCE: 27

Met Lys Leu Pro Val Arg Leu Leu Val Leu Met Phe Trp Ile Pro Gly
1               5                   10                  15

Ser Ser Ser Asp Ala Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Arg Ile Ser Arg Val Glu Ala Glu Asp Leu Gly Val Tyr Phe Cys
            100                 105                 110

Ser Gln Ser Arg Tyr Val Pro Trp Thr Phe Gly Gly Gly Thr Lys Leu
        115                 120                 125

Glu Ile Lys
    130

<210> SEQ ID NO 28
<211> LENGTH: 141
<212> TYPE: PRT
<213> ORGANISM: Mus musculus

<400> SEQUENCE: 28

Met Gly Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Pro Gly Met Gly Val Gly Trp Ile Arg Gln Pro Ser Gly Lys
    50                  55                  60

Gly Leu Glu Trp Leu Ala His Ile Trp Trp Asp Asp Phe Lys Arg Asp
65                  70                  75                  80

Asn Pro Ala Leu Lys Ser Arg Leu Thr Ile Ser Lys Asp Thr Ser Ser
                85                  90                  95

Ser Gln Val Phe Leu Lys Ile Ala Ser Val Asp Thr Ala Asp Thr Ala
            100                 105                 110

Thr Tyr Tyr Cys Val Arg Val Asp Gly Asn Phe Leu Ser Trp Tyr Phe
        115                 120                 125

Asp Val Trp Gly Ala Gly Thr Thr Val Thr Val Ser Ser

<210> SEQ ID NO 29
<211> LENGTH: 131
<212> TYPE: PRT
<213> ORGANISM: Mus musculus

<400> SEQUENCE: 29

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Glu Arg Thr Asn Gly Asn Thr Tyr Leu His Trp Tyr Leu Gln Lys Pro
    50                  55                  60

Gly Gln Ser Pro Lys Leu Leu Ile Tyr Lys Val Ser Ser Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Phe Cys
            100                 105                 110

Ser Gln Thr Thr His Gly Pro Pro Thr Cys Gly Gly Gly Thr Lys Leu
        115                 120                 125

Glu Ile Lys
    130

<210> SEQ ID NO 30
<211> LENGTH: 137
<212> TYPE: PRT
<213> ORGANISM: Mus musculus

<400> SEQUENCE: 30

Met Gly Trp Ile Trp Ile Phe Leu Phe Leu Leu Ser Gly Thr Ala Gly
1               5                   10                  15

Val His Ser Glu Val Gln Leu Gln Gln Ser Gly Pro Glu Leu Val Arg
            20                  25                  30

Thr Gly Ala Ser Val Lys Ile Ser Cys Lys Ala Ser Gly Tyr Ser Phe
        35                  40                  45

Thr Gly Phe Tyr Met His Trp Val Lys Gln Ser Leu Gly Lys Ser Leu
    50                  55                  60

Glu Trp Ile Gly Tyr Val Ser Cys Tyr Thr Gly Ala Thr Thr Tyr Thr
65                  70                  75                  80

Gln Lys Phe Lys Gly Lys Ala Thr Phe Thr Val Asp Thr Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Glu Gly Asp Tyr Tyr Ser Met Asp Phe Trp Gly
        115                 120                 125

Gln Gly Thr Ser Val Thr Val Ser Ser
    130                 135

<210> SEQ ID NO 31
<211> LENGTH: 128
<212> TYPE: PRT
<213> ORGANISM: Mus musculus

<400> SEQUENCE: 31

Met Asp Met Arg Ala Pro Ala Gln Phe Phe Gly Ile Leu Leu Leu Trp
1               5                   10                  15

Phe Pro Gly Ile Arg Cys Asp Ile Lys Met Thr Gln Ser Pro Ser Ser
                20                  25                  30

Ile Tyr Ala Ser Leu Gly Glu Arg Val Thr Ile Thr Cys Lys Ala Ser
                35                  40                  45

Gln Asp Ile Lys Ser Tyr Leu Ser Trp Tyr Gln Gln Lys Pro Trp Lys
        50                  55                  60

Ser Pro Lys Thr Leu Ile Tyr Tyr Ala Thr Thr Leu Ala Asp Gly Val
65              70                  75                  80

Pro Ser Arg Phe Ser Gly Ser Gly Ser Gly Gln Asp Tyr Ser Leu Ile
                85                  90                  95

Ile Asn Ser Leu Glu Ser Asp Asp Ile Ala Thr Tyr Phe Cys Leu His
                100                 105                 110

His Asp Glu Ser Pro Phe Thr Phe Gly Ser Gly Thr Lys Leu Glu Ile
            115                 120                 125

<210> SEQ ID NO 32
<211> LENGTH: 137
<212> TYPE: PRT
<213> ORGANISM: Mus musculus

<400> SEQUENCE: 32

Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
                20                  25                  30

Pro Gly Glu Thr Val Gln Ile Ser Cys Lys Ala Ser Gly Tyr Ile Phe
                35                  40                  45

Thr Asp Tyr Gly Met Asn Trp Val Lys Gln Ala Pro Gly Lys Gly Leu
        50                  55                  60

Lys Trp Met Gly Cys Ile Asn Thr Tyr Thr Gly Glu Thr Ile Tyr Ser
65              70                  75                  80

Asp Asp Phe Arg Gly Arg Phe Ala Ile Ser Leu Glu Thr Ser Ala Ser
                85                  90                  95

Thr Ala Phe Ile Gln Ile Asn Asn Leu Lys Asn Glu Asp Ala Ala Thr
                100                 105                 110

Tyr Phe Cys Ala Arg Gly Asn Tyr Arg Asp Ala Ile Asp Tyr Trp Gly
            115                 120                 125

Gln Gly Thr Ser Val Thr Val Ser Ser
        130                 135

<210> SEQ ID NO 33
<211> LENGTH: 127
<212> TYPE: PRT
<213> ORGANISM: Mus musculus

<400> SEQUENCE: 33

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
                20                  25                  30

Leu Phe Ala Ser Pro Gly Glu Lys Val Thr Met Thr Cys Arg Ala Ser
                35                  40                  45

Ser Ser Val Ile Tyr Met Cys Trp Asn Gln Gln Lys Pro Gly Ser Ser
        50                  55                  60

Pro Lys Pro Trp Ile Tyr Gly Thr Ser Thr Leu Ala Ser Gly Val Pro

```
                65                  70                  75                  80
Thr Arg Phe Ser Gly Ser Gly Ser Gly Thr Tyr Ser Leu Thr Ile
                        85                  90                  95

Ser Arg Val Glu Ala Glu Asp Ala Ala Thr Tyr Tyr Cys Gln Gln Trp
                    100                 105                 110

Ser Ser Asn Pro Phe Thr Phe Gly Ser Gly Thr Lys Leu Glu Ile
            115                 120                 125

<210> SEQ ID NO 34
<211> LENGTH: 139
<212> TYPE: PRT
<213> ORGANISM: Mus musculus

<400> SEQUENCE: 34

Met Gly Trp Ser Trp Ile Phe Leu Phe Leu Leu Ser Gly Thr Ala Gly
  1               5                  10                  15

Val His Ser Glu Val Gln Leu Gln Gln Ser Gly Pro Glu Leu Val Lys
                 20                  25                  30

Pro Gly Ala Ser Val Lys Ile Ser Cys Lys Ala Ser Gly Tyr Thr Phe
             35                  40                  45

Thr Asp Tyr Asn Ile His Trp Val Lys Gln Ser His Gly Lys Ile Leu
         50                  55                  60

Glu Trp Ile Gly Tyr Ile Tyr Pro Tyr Asn Gly Val Ser Asp Tyr Asn
 65                  70                  75                  80

Gln Asn Phe Lys Ser Lys Ala Thr Leu Ile Val Asp Asn Ser Ser Asn
                 85                  90                  95

Thr Ala Tyr Met Glu Leu Arg Ser Leu Thr Ser Glu Asp Ser Ala Val
                100                 105                 110

Tyr Tyr Cys Ala Arg Trp Asp Phe Gly Ser Gly Tyr Tyr Phe Asp Tyr
            115                 120                 125

Trp Gly Gln Gly Thr Thr Leu Thr Val Ser Ser
    130                 135

<210> SEQ ID NO 35
<211> LENGTH: 393
<212> TYPE: DNA
<213> ORGANISM: Mus musculus

<400> SEQUENCE: 35
atgaagttgc ctgttaggct gttggtgctg atgttctgga ttcctggttc cagcagtgat      60
gctgtgatga cccaaactcc actctccctg cctgtcagtc ttggagatca ggcctccatc     120
tcttgcagat ctagtcagag ccttgtacac agtaatggaa acacctattt acattggtac     180
ctgcagaagc caggccagtc tccaaaactc ctgatctaca agttccaa ccgatttct        240
ggggtcccag acaggttcag tggcagtgga tcagggacag atttcacact caggatcagc     300
agagtggagg ctgaggatct gggagtttat ttctgctctc aaagtagata tgttccgtgg     360
acgttcggtg gaggcaccaa gctggaaatc aaa                                  393

<210> SEQ ID NO 36
<211> LENGTH: 423
<212> TYPE: DNA
<213> ORGANISM: Mus musculus

<400> SEQUENCE: 36
atgggcaggc ttacttcttc attcctgcta ctgattgtcc ctgcatatgt cctgtcccag      60
gttactctga aagagtctgg ccctgggata ttgcagccct ccagaccct cagtctgact     120
```

```
tgttctttct ctgggttttc actgagcact cctggtatgg gtgtaggctg gattcgtcag      180
ccatcaggga agggtctgga gtggctggca cacatttggt gggatgattt caagcgcgat      240
aatccagccc ttaagagccg actgactatc tctaaggata cctccagcag ccaggttttc      300
ctcaaaatcg ccagtgtgga cactgcagat actgccacat attactgtgt tcgagtggat      360
ggtaacttcc tctcctggta tttcgatgtc tggggcgctg ggaccacggt caccgtctcc      420
tca                                                                     423

<210> SEQ ID NO 37
<211> LENGTH: 393
<212> TYPE: DNA
<213> ORGANISM: Mus musculus

<400> SEQUENCE: 37
atgaagttgc ctgttaggct gttggtgctg atgttctgga ttcctgcttc cagcagtgat       60
gttgtgatga cccaaactcc actctccctg cctgtcagtc ttggagatca agcctccatc      120
tcttgcagat ctagtcagag ccttgaacgc actaatggaa cacctatttt acattggtac      180
ctgcagaagc caggccagtc tccaaaactc ctgatctaca agtttccagc cgatttttct      240
ggggtcccag ataggttcag tggcagtgga tcagggacag atttcacact caagatcagt      300
agagtggagg ctgaggatct gggaatttat ttctgttctc aaactacaca tggtcctccg      360
acgtgcggtg gaggcaccaa gctggaaatc aaa                                    393

<210> SEQ ID NO 38
<211> LENGTH: 411
<212> TYPE: DNA
<213> ORGANISM: Mus musculus

<400> SEQUENCE: 38
atgggatgga tctggatctt tctcttcctc ctgtcaggaa ctgcaggtgt ccactctgag       60
gtccagctgc agcagtctgg acctgagtta gtgaggactg ggcttcagt gaagatatcc      120 tgcaaggctt ctggttactc attcactggt ttctacatgc actgggtcaa gcagagcctt      180
ggaaagagcc ttgagtggat tggatatgtt agttgttaca ctggtgctac tacctacacc      240
cagaagttca gggcaaggc cacatttact gttgacacat cctccagcac agcctacatg      300
caactcaaca gcctgacatc tgaagactct gcggtctatt actgtgcaag agaaggggat      360
tactattcta tggacttctg gggtcaagga acctcagtca ccgtctcctc a               411

<210> SEQ ID NO 39
<211> LENGTH: 386
<212> TYPE: DNA
<213> ORGANISM: Mus musculus

<400> SEQUENCE: 39
atggacatga gggcccctgc tcagtttttt gggatcttgt tgctctggtt tccaggtatc       60
agatgtgaca tcaagatgac ccagtctcca tcgtccattt atgcatcgct gggagagagg      120
gtcactataa cttgcaaggc gagtcaggac attaaaagct atttaagctg gtaccaacag      180
aaaccctgga atctcctaa gaccctgatc tattatgcaa caaccttggc agatggggtc      240
ccatcaagat tcagtggcag tggatctggg caagattatt ctctaatcat caacagcctg      300
gagtctgacg atatagctac ttatttctgt ctacaccatg atgagagccc attcacgttc      360
ggctcgggga caaaattgga aataaa                                            386

<210> SEQ ID NO 40
```

```
<211> LENGTH: 411
<212> TYPE: DNA
<213> ORGANISM: Mus musculus

<400> SEQUENCE: 40
atggcttggg tgtggacctt gctgttcctg atggcagctg cccaaagtgc ccaagcacag      60
atccagttgg tgcagtctgg acctgagctg aagaagcctg agagacagt ccagatctcc     120 tgcaaggctt ctggctatat cttcacagac tatggaatga actgggtgaa acaggctcca    180
ggaaagggtt taaatggat gggctgtata acacctaca ctggagagac aatatatagt      240
gatgacttca ggggacggtt tgccatctct ttggaaacct ctgccagcac tgcctttatt    300
cagatcaaca acctcaaaaa tgaggacgcg gcaacatatt tctgtgcaag gggaaattac    360
agggatgcta ttgactattg gggtcaagga acctcagtca ccgtctcctc a             411

<210> SEQ ID NO 41
<211> LENGTH: 383
<212> TYPE: DNA
<213> ORGANISM: Mus musculus

<400> SEQUENCE: 41
atggattttc aagtgcagat tttcagcttc ctgctaatca gtgcttcagt cataatgtcc      60
agaggacaaa ttgttctctc ccagtctcca gcaatcctgt ttgcatctcc aggggagacg    120
gtcacaatga cttgcagggc cagttcaagt gtaatttaca tgtgttggaa tcagcagaag    180
ccaggatcct cccccaaacc ctggatttat ggcacatcca ccctggcttc tggagtccct    240
actcgcttca gtggcagtgg gtctgggacc tcttactctc tcacaatcag cagagtagag    300
gctgaagatg ctgccactta ttactgccag cagtggagta gtaacccatt cacgttcggc    360
tcggggacaa agttggaaat aaa                                            383

<210> SEQ ID NO 42
<211> LENGTH: 417
<212> TYPE: DNA
<213> ORGANISM: Mus musculus

<400> SEQUENCE: 42
atgggatgga gctggatctt tctcttcctc ctgtcaggaa ctgcaggcgt ccactctgag     60
gtccagcttc agcagtcagg acctgagctg gtgaaacctg gggcctcagt gaagatatcc    120
tgcaaggctt ctggatacac attcactgac tacaacattc actgggtgaa acagagccat    180
ggaaagatcc ttgagtggat tggatatatt tatccttata tggtgtttc tgactacaac     240 cagaatttca gagcaaggc cacattgatt gtagacaatt cctccaacac agcctacatg     300
gaactccgca gcctgacatc tgaggactct gcagtctatt attgtgcaag atgggacttc    360
ggtagtggct actactttga ctactgggc caaggcacca ctctcacagt ctcctca        417

<210> SEQ ID NO 43
<211> LENGTH: 45
<212> TYPE: RNA
<213> ORGANISM: Mus musculus

<400> SEQUENCE: 43
rcgacuggag cacgaggaca cugacaugga cugaaggagu agaaa                     45

<210> SEQ ID NO 44
<211> LENGTH: 54
<212> TYPE: DNA
<213> ORGANISM: Mus musculus
```

```
<400> SEQUENCE: 44
gctgtcaacg atacgctacg taacggcatg acagtgtttt tttttttttt tttt        54

<210> SEQ ID NO 45
<211> LENGTH: 30
<212> TYPE: DNA
<213> ORGANISM: Mus musculus

<400> SEQUENCE: 45
ayctccacac acaggrrcca gtggatagac                                    30

<210> SEQ ID NO 46
<211> LENGTH: 21
<212> TYPE: DNA
<213> ORGANISM: Mus musculus

<400> SEQUENCE: 46
ggatacagtt ggtgcagcat c                                             21

<210> SEQ ID NO 47
<211> LENGTH: 23
<212> TYPE: DNA
<213> ORGANISM: Mus musculus

<400> SEQUENCE: 47
cgactggagc acgaggacac tga                                           23

<210> SEQ ID NO 48
<211> LENGTH: 20
<212> TYPE: DNA
<213> ORGANISM: Mus musculus

<400> SEQUENCE: 48
attaaccctc actaaaggga                                               20

<210> SEQ ID NO 49
<211> LENGTH: 20
<212> TYPE: DNA
<213> ORGANISM: Mus musculus

<400> SEQUENCE: 49
taatacgact cactataggg                                               20

<210> SEQ ID NO 50
<211> LENGTH: 20
<212> TYPE: DNA
<213> ORGANISM: Mus musculus

<400> SEQUENCE: 50
attaaccctc actaaaggga                                               20

<210> SEQ ID NO 51
<211> LENGTH: 20
<212> TYPE: DNA
<213> ORGANISM: Mus musculus

<400> SEQUENCE: 51
taatacgact cactataggg                                               20

<210> SEQ ID NO 52
<211> LENGTH: 383
<212> TYPE: DNA
<213> ORGANISM: Mus musculus
```

-continued

<400> SEQUENCE: 52

```
atggattttc aagtgcagat tttcagcttc ctgctaatca gtgcttcagt cataatgtcc      60
agaggacaaa ttattctctc ccagtctcca gcaatcctgt ctgcatctcc aggggagaag     120
gtcacaatga cttgcagggc cagttcaagt gtaagttcca ttcactggta ccagcagaag     180
ccagaatcct cccccaaacc ctggatttac gccacatcca acctggcttc tggagtccct     240
gttcgcttca gtggcagtgg gtctgggacc tcttatactc tcacaatcag cagaatggag     300
gctgcagatg ctgccactta ttactgccag cagtggagta ttgatccagc acgttcgga     360
gggggaccca agctggaaat aaa                                             383
```

<210> SEQ ID NO 53
<211> LENGTH: 135
<212> TYPE: PRT
<213> ORGANISM: Mus musculus

<400> SEQUENCE: 53

```
Met Ala Trp Val Trp Thr Leu Leu Phe Leu Met Ala Ala Ala Gln Ser
 1               5                  10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ser Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Ala Tyr Ile Gly Glu Pro Thr Tyr Ala
65                  70                  75                  80

Asp Asp Phe Lys Gly Arg Phe Ala Phe Ser Leu Glu Ala Ser Thr His
                85                  90                  95

Thr Ala Tyr Leu Gln Ile Asn Ser Leu Lys Ser Glu Asp Thr Ala Thr
            100                 105                 110

Tyr Phe Cys Ala Ser Gly Gly Asn Ser Leu Asp Phe Trp Gly Gln Gly
        115                 120                 125

Thr Thr Leu Thr Val Ser Ser
    130                 135
```

<210> SEQ ID NO 54
<211> LENGTH: 127
<212> TYPE: PRT
<213> ORGANISM: Mus musculus

<400> SEQUENCE: 54

```
Met Asp Phe Gln Val Gln Ile Phe Ser Phe Leu Leu Ile Ser Ala Ser
 1               5                  10                  15

Val Ile Met Ser Arg Gly Gln Ile Ile Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Ser Ile His Trp Tyr Gln Gln Lys Pro Glu Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Thr Leu Thr Ile
                85                  90                  95

Ser Arg Met Glu Ala Ala Asp Ala Ala Thr Tyr Tyr Cys Gln Gln Trp
            100                 105                 110
```

Ser Ile Asp Pro Ala Thr Phe Gly Gly Gly Thr Lys Leu Glu Ile
            115                 120                 125

<210> SEQ ID NO 55
<211> LENGTH: 141
<212> TYPE: PRT
<213> ORGANISM: Mus musculus

<400> SEQUENCE: 55

Met Lys Cys Ser Trp Val Ile Phe Phe Leu Met Ala Val Val Thr Gly
  1               5                  10                  15

Val Asn Ser Glu Val Gln Leu Gln Gln Ser Gly Ala Glu Leu Val Lys
             20                  25                  30

Pro Gly Ala Ser Val Lys Leu Ser Cys Thr Ala Ser Gly Phe Asn Ile
         35                  40                  45

Lys Asp Thr Tyr Met His Trp Val Lys Gln Arg Pro Glu Gln Gly Leu
     50                  55                  60

Glu Trp Ile Gly Arg Ile Asp Pro Ala Asn Gly Asn Thr Lys Tyr Asp
 65                  70                  75                  80

Pro Lys Phe Gln Gly Lys Ala Thr Ile Thr Ala Asp Thr Ser Ser Asn
                 85                  90                  95

Thr Ala Tyr Val Gln Leu Ser Ser Leu Thr Ser Glu Asp Thr Ala Val
            100                 105                 110

Tyr Tyr Cys Ala Ser Ser Asp Ile Tyr Tyr Gly Asn Pro Gly Gly Phe
        115                 120                 125

Ala Tyr Trp Gly Gln Gly Thr Leu Val Thr Val Ser Ala
    130                 135                 140

<210> SEQ ID NO 56
<211> LENGTH: 129
<212> TYPE: PRT
<213> ORGANISM: Mus musculus

<400> SEQUENCE: 56

Met Asp Phe Gln Val Gln Ile Phe Ser Phe Leu Leu Ile Ser Ala Ser
  1               5                  10                  15

Val Ile Met Ser Arg Gly Gln Ile Val Leu Thr Gln Ser Pro Ala Ile
             20                  25                  30

Met Ser Ala Ser Leu Gly Glu Arg Val Thr Met Thr Cys Thr Ala Ser
         35                  40                  45

Ser Ser Val Ser Ser Tyr Leu His Trp Tyr Gln Gln Lys Pro Gly
     50                  55                  60

Ser Ser Pro Lys Leu Trp Ile Tyr Ser Thr Ser Asn Leu Ala Ser Gly
 65                  70                  75                  80

Val Pro Ala Arg Phe Ser Gly Ser Gly Ser Gly Thr Ser Tyr Ser Leu
                 85                  90                  95

Thr Ile Ser Ser Met Glu Ala Glu Asp Ala Ala Thr Tyr Tyr Cys His
            100                 105                 110

Gln Tyr His Arg Ser Pro Phe Thr Phe Gly Ser Gly Thr Lys Leu Glu
        115                 120                 125

Ile

<210> SEQ ID NO 57
<211> LENGTH: 406
<212> TYPE: DNA
<213> ORGANISM: Mus musculus

<400> SEQUENCE: 57

```
atggcttggg tgtggacctt gctattcctg atggcagctg cccaaagtgc ccaagcacag      60
atccagttgg tgcagtctgg acctgaactg aagaagcctg agagacagt caagatctcc      120 tgcaaggctt ctggatattc cttcacaaac tatggaatga actgggtgaa gcaggctcca    180
gggaagggtt taaagtggat gggctggata acgcctaca ttggagagcc aacatatgct      240
gatgacttca agggacgatt tgccttctct ctggaagcct ctacccacac tgcctatttg      300
cagatcaaca gcctcaaaag tgaggacacg gctacatatt tctgtgcaag tgggggtaac    360
tcccttgact tttggggcca aggcaccact ctcacagtct cctcag                    406

<210> SEQ ID NO 58
<211> LENGTH: 423
<212> TYPE: DNA
<213> ORGANISM: Mus musculus

<400> SEQUENCE: 58
atgaaatgca gctgggttat cttcttcctg atggcagtgg ttacagggt caattcagag      60 gttcagctgc agcagtctgg ggcagagctt gtgaagccag gggcctcagt caagttgtcc    120
tgcacagctt ctggcttcaa cattaaagac acctatatgc actgggtgaa gcagaggcct    180
gaacagggcc tggagtggat tggaaggatt gatcctgcga atggtaatac taaatatgac    240
ccgaagttcc agggcaaggc cactataaca gcagacacat cctccaacac agcctacgtg    300
cagctcagca gcctgacatc tgaggacact gccgtctatt actgtgctag tagtgacatc    360
tactatggta accccggggg gtttgcttac tggggccaag gactctggt cactgtctct      420 gca                                                                   423

<210> SEQ ID NO 59
<211> LENGTH: 389
<212> TYPE: DNA
<213> ORGANISM: Mus musculus

<400> SEQUENCE: 59
atggattttc aggtgcagat tttcagcttc ctgctaatca gtgcctcagt cataatgtcc      60
agaggacaaa ttgttctcac ccagtctcca gcaatcatgt ctgcatctct aggggaacgg    120
gtcaccatga cctgcactgc cagctcaagt gtaagttcca gttacttgca ctggtaccag    180
cagaagccag gatcctcccc caaactctgg atttatagca catccaacct ggcttctgga    240
gtcccagctc gcttcagtgg cagtgggtct gggacctctt actctctcac aatcagcagc    300
atggaggctg aagatgctgc cacttattac tgccaccagt atcatcgttc cccattcacg    360
ttcggctcgg ggacaaagtt ggaaataaa                                       389

<210> SEQ ID NO 60
<211> LENGTH: 10
<212> TYPE: PRT
<213> ORGANISM: Mus musculus

<400> SEQUENCE: 60

Gly Tyr Ser Phe Thr Asn Tyr Gly Met Asn
 1               5                  10

<210> SEQ ID NO 61
<211> LENGTH: 17
<212> TYPE: PRT
<213> ORGANISM: Mus musculus

<400> SEQUENCE: 61

Trp Ile Asn Ala Tyr Ile Gly Glu Pro Thr Tyr Ala Asp Asp Phe Lys
```

```
                 1               5              10              15

Gly

<210> SEQ ID NO 62
<211> LENGTH: 7
<212> TYPE: PRT
<213> ORGANISM: Mus musculus

<400> SEQUENCE: 62

Gly Gly Asn Ser Leu Asp Phe
 1               5

<210> SEQ ID NO 63
<211> LENGTH: 10
<212> TYPE: PRT
<213> ORGANISM: Mus musculus

<400> SEQUENCE: 63

Arg Ala Ser Ser Ser Val Ser Ser Ile His
 1               5                  10

<210> SEQ ID NO 64
<211> LENGTH: 7
<212> TYPE: PRT
<213> ORGANISM: Mus musculus

<400> SEQUENCE: 64

Ala Thr Ser Asn Leu Ala Ser
 1               5

<210> SEQ ID NO 65
<211> LENGTH: 9
<212> TYPE: PRT
<213> ORGANISM: Mus musculus

<400> SEQUENCE: 65

Gln Gln Trp Ser Ile Asp Pro Ala Thr
 1               5

<210> SEQ ID NO 66
<211> LENGTH: 10
<212> TYPE: PRT
<213> ORGANISM: Mus musculus

<400> SEQUENCE: 66

Gly Phe Asn Ile Lys Asp Thr Tyr Met His
 1               5                  10

<210> SEQ ID NO 67
<211> LENGTH: 17
<212> TYPE: PRT
<213> ORGANISM: Mus musculus

<400> SEQUENCE: 67

Arg Ile Asp Pro Ala Asn Gly Asn Thr Lys Tyr Asp Pro Lys Phe Gln
 1               5                  10                  15

Gly

<210> SEQ ID NO 68
<211> LENGTH: 13
<212> TYPE: PRT
<213> ORGANISM: Mus musculus

<400> SEQUENCE: 68
```

```
Ser Asp Ile Tyr Tyr Gly Asn Pro Gly Gly Phe Ala Tyr
1               5                  10

<210> SEQ ID NO 69
<211> LENGTH: 12
<212> TYPE: PRT
<213> ORGANISM: Mus musculus

<400> SEQUENCE: 69

Thr Ala Ser Ser Ser Val Ser Ser Ser Tyr Leu His
1               5                  10

<210> SEQ ID NO 70
<211> LENGTH: 7
<212> TYPE: PRT
<213> ORGANISM: Mus musculus

<400> SEQUENCE: 70

Ser Thr Ser Asn Leu Ala Ser
1               5

<210> SEQ ID NO 71
<211> LENGTH: 9
<212> TYPE: PRT
<213> ORGANISM: Mus musculus

<400> SEQUENCE: 71

His Gln Tyr His Arg Ser Pro Phe Thr
1               5
```

NUCLEIC ACID MOLECULES ENCODING ANTIBODIES THAT BIND CELL-ASSOCIATED CA 125/O772P

CROSS-REFERENCE TO RELATED APPLICATIONS

The present application is a divisional of U.S. application Ser. No. 12/183,719, filed Jul. 31, 2008, which is a divisional of U.S. application Ser. No. 10/687,035, filed Oct. 15, 2003, now U.S. Pat. No. 7,729,382, which claims the benefit of U.S. Provisional Application No. 60/485,986, filed Jul. 10, 2003 and U.S. Provisional Application No. 60/418,828, filed Oct. 16, 2002; each of which is herein incorporated by reference in its entirety.

1. FIELD OF THE INVENTION

The present invention provides antibodies, and antigen-binding fragments of antibodies, that preferentially bind cell-associated CA 125/O772P polypeptides relative to shed CA 125/O772P polypeptides, methods for identifying such antibodies and antigen-binding fragments, and methods for making such antibodies and antigen-binding antibody fragments. The present invention further provides methods of preventing, managing, treating or ameliorating one or more symptoms associated with a CA 125/O772P-related disorder. In particular, the present invention provides methods of preventing, managing, treating, or ameliorating one or more symptoms associated with a cell proliferative disorder. For example, the present invention provides methods of preventing, managing, treating or ameliorating one or more symptoms associated with cancer. In a preferred embodiment, the present invention provides methods of preventing, managing, treating or ameliorating one or more symptoms of ovarian cancer. The present invention also provides compositions and articles of manufacture for use in preventing, managing, treating or ameliorating one or more symptoms associated with a CA 125/O772P-related disorder, for example cancer, e.g., ovarian cancer. The present invention still further provides methods for diagnosing a CA 125/O772P-related disorder or predisposition to developing such a disorder.

2. BACKGROUND OF THE INVENTION

The high molecular weight polypeptide referred to as CA 125 can be detected in approximately 80% of all patients with ovarian carcinomas (see Kabawat et al., Am. J. Clin. Pathol. 79:98-104 (1983); and Gadducci et al., Gynecol. Oncol. 44:147-154 (1992)). CA 125 is present on the surface of tumor cells, and elevated secreted, or "shed," forms of CA 125 are present in approximately 80-90% of ovarian cancer patients.

Antibodies directed against CA 125 have been produced and utilized for the determination of CA 125 concentrations and for purification of CA 125 from cell culture medium. See, e.g., Bast et al., J. Clin. Invest. 68(5):1331-1337 (1981); Krantz et al., J. Cell. Biochem. (Suppl.) 12 (E):139 (1988); U.S. Pat. Nos. 4,921,790, 5,059,680, and 5,976,818; and JP11014626.

In addition to antibodies for monitoring the presence of CA 125, U.S. Pat. Nos. 5,858,361 and 6,241,985 describe anti-idiotypic anti-CA 125 antibodies as therapeutic agents.

Despite the above, CA 125-related disorders such as ovarian cancer remain a major problem and, as such, a great need exists for methods and compositions for the treatment of such disorders.

Citation or identification of any reference in this or any other section of this application shall not be construed as an admission that such reference is available as prior art to the present invention.

3. SUMMARY OF THE INVENTION

The present invention is based, in part, on the recognition that the events that produce shed CA 125/O772P also leave a portion of the extracellular region of the CA 125/O772P amino acid sequence in cell-associated form, i.e., also yield cell-associated CA 125/O772P. The present invention is further based, in part, on the recognition that antibodies, and antigen-binding antibody fragments, that preferentially bind cell-associated CA 125/O772P relative to shed CA 125/O772P can be generated, and that such antibodies, or antigen-binding antibody fragments, can, for example, be utilized to prevent, manage, treat or ameliorate a CA 125/O772P-related disorder or one or more symptoms of a CA 125/O772P-related disorder such as a cell proliferative disorder, for example, cancer, e.g., ovarian cancer.

In a first aspect, the present invention provides an isolated antibody, or an antigen-binding antibody fragment, that preferentially binds cell-associated CA 125/O772P polypeptide relative to shed CA 125/O772P polypeptide. Also provided is an isolated antibody or antigen-binding antibody fragment that binds to the peptide of FIG. 1. Such antibodies and antigen-binding antibody fragments of the invention are useful for a variety of therapeutic, prophylactic, diagnostic, and purification purposes as described herein.

In another embodiment, an antibody or antigen-binding antibody fragment of the invention is one that binds the peptide of SEQ ID NO:1 or SEQ ID NO:2 and preferentially binds cell-associated CA 125/O772P. In one particular such embodiment, the antibody or antigen-binding antibody fragment of the invention binds the non-repeat region depicted in SEQ ID NO:1 or SEQ ID NO:2. In another such embodiment, the antibody or antigen-binding antibody fragment of the invention binds a repeat region depicted in SEQ ID NO:1 or SEQ ID NO:2.

In a first embodiment, the antibody or antigen-binding antibody fragment of the invention exhibits, in an ELISA Competition Assay, less than about 25%, less than about 20%, less than about 15%, less than about 10%, or less than about 5% inhibition of binding to the peptide of FIG. 1 (SEQ ID NO: 1) in the presence of a 25-fold (weight/weight) excess of shed CA 125/O772P over the peptide of FIG. 1 (SEQ ID NO: 1). In a second embodiment, the antibody or antigen-binding antibody fragment of the invention exhibits, in a Flow Cytometry Competition Assay, an $IC_{50}$, as measured by percent-positive cells, of at least about 0.05 mg/ml, at least about 0.25 mg/ml, at least about 0.5 mg/ml, at least about 0.75 mg/ml, or at least about 1.0 mg/ml shed CA 125/O772P. In a third embodiment, the antibody or antigen-binding antibody fragment of the invention binds the peptide of FIG. 1, but does not detectably bind shed CA 125/O772P polypeptide.

An antibody, or antigen-binding antibody fragment, that satisfies any one of these three embodiments constitutes an antibody or antigen-binding antibody fragment that "preferentially binds" cell-associated CA 125/O772P polypeptide relative to shed CA 125/O772P polypeptide.

Among the antibodies and antigen-binding antibody fragments of the invention are antibodies or antigen-binding antibody fragments that bind the peptide of FIG. 1 (SEQ ID NO: 1) with a of less than about 100 nM, less than about 10 nM, less than about 1 nM, less than about 100 pM, or less than about 10 pM as measured by the BIAcore Affinity Assay, which is described in Section 6.4, hereinbelow.

Among the preferred embodiments of the antibodies or antigen-binding antibody fragments of the invention are antibodies or antigen-binding antibody fragments that mediate lysis of CA 125/O772P-positive tumor cells in an antibody-dependent cellular cytotoxicity (ADCC) assay. Such antibodies or antigen-binding antibody fragments include, for example, ones that mediate at least about 10% lysis of CA 125/O772P-positive tumor cells in an ADCC assay at a 50:1 effector:target ratio at a concentration of 5 µg antibody or antigen-binding fragment per ml; mediate at least about 20% lysis of CA 125/O772P-positive tumor cells in an ADCC assay at a 50:1 effector:target ratio at a concentration of 5 µg antibody or antigen-binding fragment per ml; mediate at least about 10% lysis of CA 125/O772P-positive tumor cells in art ADCC assay at a 50:1 effector:target ratio at a concentration of 5.0 µg antibody or antigen-binding fragment per ml; mediate at least about 10% lysis of CA 125/O772P-positive tumor cells in an ADCC assay at a 25:1 effector:target ratio at a concentration of 5 µg antibody or antigen-binding antibody fragment per ml; mediate at least about 10% lysis of CA 125/O772P-positive tumor cells in an ADCC assay at a 12.5:1 effector:target ratio at a concentration of 5 µg antibody or antigen-binding antibody fragment per ml; mediate at least about 10% lysis of CA 125/O772P-positive tumor cells in an ADCC assay at a 12.5:1 effector:target ratio at a concentration of 0.5 µg antibody or antigen-binding antibody fragment per ml; or that mediate at least about 10% lysis of CA 125/O772P-positive tumor cells in an ADCC assay at a 12.5:1 effector:target ratio at a concentration of 50 ng antibody or antigen-binding antibody fragment per ml.

Preferred embodiments of the invention also include antibodies or antigen-binding antibody fragments that mediate lysis of CA 125/O772P-positive tumor cells in a complement-dependent cytotoxicity (CDC) assay. Such antibodies or antigen-binding antibody fragments include, for example, ones that mediate lysis in a range of about 15% lysis at 5 µg/ml to about 95% lysis at about 0.1 µg/ml antibody or antigen-binding antibody fragment concentration.

Preferred embodiments of the antibodies or antigen-binding antibody fragments of the invention also include antibodies and antigen-binding antibody fragments that inhibit CA 125/O772P-positive tumor growth.

In one particular embodiment, an antibody of the invention is a monoclonal antibody produced by hybridoma 4E7 (ATCC® Accession No. PTA-5109), or by hybridoma 7A11 (ATCC® Accession No. PTA-5110), or by hybridoma 7C6 (ATCC® Accession No. PTA-5111), or by hybridoma 7F10 (ATCC® Accession No. PTA-5112), or by hybridoma 7G10 (ATCC® Accession No. PTA-5245), or by hybridoma 7H1 (ATCC® Accession No. PTA-5114), or by hybridoma 8A1 (ATCC® Accession No. PTA-5115), or by hybridoma 8B5 (ATCC® Accession No. PTA-5116), or by hybridoma 8C3 (ATCC® Accession No. PTA-5246), or by hybridoma 8E3 (ATCC® Accession No. PTA-5118), or by hybridoma 8G9 (ATCC® Accession No. PTA-5119), or by hybridoma 15C9 (ATCC® Accession No. PTA-5106), or by hybridoma 16C7 (ATCC® Accession No. PTA-5107), or by hybridoma 16H9 (ATCC® Accession No. PTA-5108), or by hybridoma 117.1 (ATCC® Accession No. PTA-4567), or by hybridoma 325.1 (ATCC® Accession No. PTA-5120), or by hybridoma 368.1 (ATCC® Accession No. PTA-4568), or by hybridoma 446.1 (ATCC® Accession No. PTA-5549), or by hybridoma 501.1 (ATCC® Accession No. PTA-4569), or by hybridoma 621.1 (ATCC® Accession No. PTA-5121), or by hybridoma 633.1 (ATCC® Accession No. PTA-5122), or by hybridoma 654.1 (ATCC® Accession No. PTA-5247), or by hybridoma 725.1 (ATCC® Accession No. PTA-5124), or by hybridoma 776.1 (ATCC® Accession No. PTA-4570).

In another particular embodiment, an antibody or antigen-binding antibody fragment of the invention is an antibody or antigen-binding antibody fragment that competes with the monoclonal antibody produced by hybridoma 4E7 (ATCC® Accession No. PTA-5109), or by hybridoma 7A11 (ATCC® Accession No. PTA-5110), or by hybridoma 7C6 (ATCC® Accession No. PTA-5111), or by hybridoma 7F10 (ATCC® Accession No. PTA-5112), or by hybridoma 7G10 (ATCC® Accession No. PTA-5245), or by hybridoma 7H1 (ATCC® Accession No. PTA-5114), or by hybridoma 8A1 (ATCC® Accession No. PTA-5115), or by hybridoma 8B5 (ATCC® Accession No. PTA-5116), or by hybridoma 8C3 (ATCC® Accession No. PTA-5246), or by hybridoma 8E3 (ATCC® Accession No. PTA-5118), or by hybridoma 8G9 (ATCC® Accession No. PTA-5119), or by hybridoma 15C9 (ATCC® Accession No. PTA-5106), or by hybridoma 16C7 (ATCC® Accession No. PTA-5107), or by hybridoma 16H9 (ATCC® Accession No. PTA-5108), or by hybridoma 117.1 (ATCC® Accession No. PTA-4567), or by hybridoma 325.1 (ATCC® Accession No. PTA-5120), or by hybridoma 368.1 (ATCC® Accession No. PTA-4568), or by hybridoma 446.1 (ATCC® Accession No. PTA-5549), or by hybridoma 501.1 (ATCC® Accession No. PTA-4569), or by hybridoma 621.1 (ATCC® Accession No. PTA-5121), or by hybridoma 633.1 (ATCC® Accession No. PTA-5122), or by hybridoma 654.1 (ATCC® Accession No. PTA-5247), or by hybridoma 725.1 (ATCC® Accession No. PTA-5124), or by hybridoma 776.1 (ATCC® Accession No. PTA-4570) for binding to cell-associated CA 125/O772P. Antibodies or antigen-binding antibody fragments of the invention are considered to compete for binding if they compete for binding in an ELISA Cross-Competition Assay and/or a FACS Cross-Competition Assay. An antibody or antigen-binding antibody fragment is considered to compete for binding in an ELISA Cross-Competition Assay or a FACS Cross-Competition Assay if the $IC_{50}$ for the competitor antibody or antigen-binding fragment is a concentration no more than about 100-fold above the concentration of the antibody or antigen-binding antibody fragment. In a preferred embodiment, the $IC_{50}$ of the competitor antibody or antigen-binding antibody fragment is a concentration no more than about 10-fold above the concentration of the antibody or antigen-binding fragment. In a more preferred embodiment, the $IC_{50}$ of the competitor antibody or antigen-binding antibody fragment is a concentration no more than about equimolar with the concentration of the antibody or antigen-binding antibody fragment.

In another particular embodiment, an antibody or antigen-binding fragment of the invention is one that comprises a 117.1 light chain polypeptide variable region ("117.1L") comprising the amino acid sequence depicted in SEQ ID NO:27 (117.1L). In yet another particular embodiment, an antibody or antigen-binding fragment of the invention is one that comprises a 117.1 heavy chain polypeptide variable region ("117.1H") comprising the amino acid sequence depicted in SEQ ID NO:28 (117.1H). In still another particular embodiment, an antibody or antigen-binding fragment of the invention is one that comprises a light chain polypeptide variable region comprising the amino acid sequence depicted in SEQ ID NO:27 (117.1L) and a heavy chain polypeptide variable region comprising the amino acid sequence depicted in SEQ ID NO:28 (117.1H).

In another particular embodiment, an antibody or antigen-binding fragment of the invention is one that comprises a 368.1 light chain polypeptide variable region ("368.1L")

comprising the amino acid sequence depicted in SEQ ID NO:29 (368.1L). In yet another particular embodiment, an antibody or antigen-binding fragment of the invention is one that comprises a 368.1 heavy chain variable region ("368.1H") comprising the amino acid sequence depicted in SEQ ID NO:30 (368.1H). In still another particular embodiment, an antibody or antigen-binding fragment of the invention is one that comprises a light chain polypeptide variable region comprising the amino acid sequence depicted in SEQ ID NO:29 (368.1L) and a heavy chain polypeptide variable region comprising the amino acid sequence depicted in SEQ ID NO:30 (368.1H).

In another particular embodiment, an antibody or antigen-binding fragment of the invention is one that comprises a 501.1 light chain polypeptide variable region ("501.1L") comprising the amino acid sequence depicted in SEQ ID NO:31 (501.1L). In yet another particular embodiment, an antibody or antigen-binding fragment of the invention is one that comprises a 501.1 heavy chain variable region ("501.1H") comprising the amino acid sequence depicted in SEQ ID NO:32 (501.1H). In still another particular embodiment, an antibody or antigen-binding fragment of the invention is one that comprises a light chain polypeptide variable region comprising the amino acid sequence depicted in SEQ ID NO:31 (501.1L) and a heavy chain polypeptide variable region comprising the amino acid sequence depicted in SEQ ID NO:32 (501.1H).

In another particular embodiment, an antibody or antigen-binding fragment of the invention is one that comprises a 776.1 light chain polypeptide variable region ("776.1L") comprising the amino acid sequence depicted in SEQ ID NO:33 (776.1L). In yet another particular embodiment, an antibody or antigen-binding fragment of the invention is one that comprises a 776.1 heavy chain variable region ("776.1H") comprising the amino acid sequence depicted in SEQ ID NO:34 (776.1H). In still another particular embodiment, an antibody or antigen-binding fragment of the invention is one that comprises a light chain polypeptide variable region comprising the amino acid sequence depicted in SEQ ID NO:33 (776.1L) and a heavy chain polypeptide variable region comprising the amino acid sequence depicted in SEQ ID NO:34 (776.1H).

In another particular embodiment, an antibody or antigen-binding fragment of the invention is one that comprises a 725.1 light chain polypeptide variable region ("725.1L") comprising the amino acid sequence depicted in SEQ ID NO:54. In yet another particular embodiment, an antibody or antigen-binding fragment of the invention is one that comprises a 725.1 heavy chain variable region ("725.1H") comprising the amino acid sequence depicted in SEQ ID NO:53. In still another particular embodiment, an antibody or antigen-binding fragment of the invention is one that comprises a light chain polypeptide variable region comprising the amino acid sequence depicted in SEQ ID NO:54 and a heavy chain polypeptide variable region comprising the amino acid sequence depicted in SEQ ID NO:53.

In another particular embodiment, an antibody or antigen-binding fragment of the invention is one that comprises a 16H9 light chain polypeptide variable region ("16H9L") comprising the amino acid sequence depicted in SEQ ID NO:56. In yet another particular embodiment, an antibody or antigen-binding fragment of the invention is one that comprises a 16H9 heavy chain variable region ("16H9") comprising the amino acid sequence depicted in SEQ ID NO:55. In still another particular embodiment, an antibody or antigen-binding fragment of the invention is one that comprises a light chain polypeptide variable region comprising the amino acid sequence depicted in SEQ ID NO:56 and a heavy chain polypeptide variable region comprising the amino acid sequence depicted in SEQ ID NO:55.

In another particular embodiment, the antibody or antigen-binding antibody fragment of the invention is one that comprises a light chain polypeptide variable region comprising the amino acid sequence depicted in SEQ ID NO:27 (117.1L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:29 (368.1L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H)

In another particular embodiment, the antibody or antigen-binding antibody fragment of the invention is one that comprises a light chain polypeptide variable region comprising the amino acid sequence depicted in SEQ ID NO:31 (501.1L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H)

In another particular embodiment, the antibody or antigen-binding antibody fragment of the invention is one that comprises a light chain polypeptide variable region comprising the amino acid sequence depicted in SEQ ID NO:33 (776.1L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:54 (725.1L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:33 (16H9L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H).

The antibodies of the invention can include, but are not limited to, polyclonal antibodies, monoclonal antibodies, chimeric antibodies, humanized antibodies, human antibodies, bi-specific antibodies, tri-specific antibodies, multi-specific antibodies, diabodies, tribodies, single-chain antibodies or anti-idiotypic antibodies. In a preferred embodiment, an antibody of the invention is a monoclonal antibody that preferentially bind cell-associated CA 125/O772P polypeptide relative to shed CA 125/O772P polypeptide.

The antigen-binding antibody fragments of the invention can include, but are not limited to, Fab fragments, F(ab')$_2$ fragments, disulfide-linked F$_v$s, single-chain F$_v$s, variable light chain polypeptide (VL)-containing fragments, variable heavy chain polypeptide (VH)-containing fragments, or complementarity-determining region (CDR)-containing fragments, and fragments of any of the antibodies of the invention listed above.

Further, the antibodies and antigen-binding antibody fragments of the invention can be of any immunoglobulin class. For example, the antibodies of the invention can be IgG, IgM, IgE, IgD, IgA or IgY class antibodies. The antibodies of the invention can also be of any isotype. For example, an antibody of the invention can be of an $IgG_1$, $IgG_2$, $IgG_3$, $IgG_4$, $IgA_1$ or $IgA_2$ heavy chain isotype.

Still further, the antibodies of the invention, can, for example, comprise a variable light chain region, for example, a κ or λ light chain variable region, a variable heavy chain region, or a CDR thereof, inserted within a framework region. For example, an antibody of the invention can comprise a Cγ1 constant region or a Cγ4 constant region.

In another aspect, the present invention provides hybridoma cells that produce a monoclonal antibody of the invention. In one embodiment, a hybridoma of the present invention is hybridoma 4E7 (ATCC® Accession No. PTA-5109), hybridoma 7A11 (ATCC® Accession No. PTA-5110), hybridoma 7C6 (ATCC® Accession No. PTA-5111), hybridoma 7F10 (ATCC® Accession No. PTA-5112), hybridoma 7G10 (ATCC® Accession No. PTA-5245), hybridoma 7H1 (ATCC® Accession No. PTA-5114), hybridoma 8A1 (ATCC® Accession No. PTA-5115), hybridoma 8B5 (ATCC® Accession No. PTA-5116), hybridoma 8C3 (ATCC® Accession No. PTA-5246), hybridoma 8E3 (ATCC® Accession No. PTA-5118), hybridoma 8G9 (ATCC® Accession No. PTA-5119), hybridoma 15C9 (ATCC® Accession No. PTA-5106), hybridoma 16C7 (ATCC® Accession No. PTA-5107), hybridoma 16H9 (ATCC® Accession No. PTA-5108), hybridoma 117.1 (ATCC® Accession No. PTA-4567), hybridoma 325.1 (ATCC® Accession No. PTA-5120), hybridoma 368.1 (ATCC® Accession No. PTA-4568), hybridoma 446.1 (ATCC® Accession No. PTA-5549), hybridoma 501.1 (ATCC® Accession No. PTA-4569), hybridoma 621.1 (ATCC® Accession No. PTA-5121), hybridoma 633.1 (ATCC® Accession No. PTA-5122), hybridoma 654.1 (ATCC® Accession No. PTA-5247), hybridoma 725.1 (ATCC® Accession No. PTA-5124), or hybridoma 776.1 (ATCC® Accession No. PTA-4570).

In another embodiment, a hybridoma of the present invention is a hybridoma that produces monoclonal antibodies that compete with the monoclonal antibody produced by hybridoma 4E7 (ATCC® Accession No. PTA-5109), hybridoma 7A11 (ATCC® Accession No. PTA-5110), hybridoma 7C6 (ATCC® Accession No. PTA-5111), hybridoma 7F10 (ATCC® Accession No. PTA-5112), hybridoma 7G10 (ATCC® Accession No. PTA-5245), hybridoma 7H1 (ATCC® Accession No. PTA-5114), hybridoma 8A1 (ATCC® Accession No. PTA-5115), hybridoma 8B5 (ATCC® Accession No. PTA-5116), hybridoma 8C3 (ATCC® Accession No. PTA-5246), hybridoma 8E3 (ATCC®Accession No. PTA-5118), hybridoma 8G9 (ATCC® Accession No. PTA-5119), hybridoma 15C9 (ATCC® Accession No. PTA-5106), hybridoma 16C7 (ATCC® Accession No. PTA-5107), hybridoma 16H9 (ATCC® Accession No. PTA-5108), hybridoma 117.1 (ATCC® Accession No. PTA-4567), hybridoma 325.1 (ATCC® Accession No. PTA-5120), hybridoma 368.1 (ATCC® Accession No. PTA-4568), hybridoma 446.1 (ATCC® Accession No. PTA-5549), hybridoma 501.1 (ATCC® Accession No. PTA-4569), hybridoma 621.1 (ATCC® Accession No. PTA-5121), hybridoma 633.1 (ATCC® Accession No. PTA-5122), hybridoma 654.1 (ATCC® Accession No. PTA-5247), hybridoma 725.1 (ATCC® Accession No. PTA-5124), or hybridoma 776.1 (ATCC® Accession No. PTA-4570). for binding to cell-associated CA 125/O772P. Antibodies are considered to compete for binding if they compete for binding in an ELISA Cross-Competition Assay and/or a FACS Cross-Competition Assay. An antibody or antigen-binding antibody fragment is considered to compete for binding in an ELISA Cross-Competition Assay or a FACS Cross-Competition Assay if the $IC_{50}$ for the competitor antibody or antigen-binding fragment is a concentration no more than about 100-fold above the concentration of the antibody or antigen-binding antibody fragment. In a preferred embodiment, the $IC_{50}$ of the competitor antibody or antigen-binding antibody fragment is a concentration no more than about 10-fold above the concentration of the antibody or antigen-binding fragment. In a more preferred embodiment, the $IC_{50}$ of the competitor antibody or antigen-binding antibody fragment is no more than about equimolar with the concentration of the antibody or antigen-binding antibody fragment.

In yet another aspect, the present invention provides an isolated nucleic acid molecule that comprises a nucleotide sequence that encodes an antibody or antigen-binding antibody fragment of the invention.

In another aspect, the present invention provides a fusion polypeptide comprising an antibody or an antigen-binding antibody fragment of the invention, i.e., one that preferentially binds cell-associated CA 125/O772P polypeptide relative to shed CA 125/O772P polypeptide, operably linked to a heterologous agent. In one embodiment of a fusion polypeptide of the invention, the antibody, or antigen-binding antibody fragment, and the heterologous agent are operably linked via a covalent linkage, such as a peptide bond or disulfide bond. In another embodiment of a fusion polypeptide of the invention, the antibody, or antigen-binding antibody fragment, and the heterologous agent are operably linked via non-covalent linkage. In another embodiment of a fusion polypeptide of the invention, the heterologous agent comprises an amino acid sequence or a radioisotope. In various non-limiting embodiments, the heterologous agent of the fusion polypeptide of the invention comprises a cytotoxic agent or a detectable, e.g., imaging, agent.

Also included as part of the invention are analogs of the antibodies, antigen-binding antibody fragments and fusion polypeptides of the invention that preferentially bind cell-associated CA 125/O772P relative to shed CA 125/O772P. In one embodiment, such an analog exhibits increased affinity for cell-associated CA 125/O772P relative to that of a corresponding pre-modified antibody, antigen-binding antibody fragments and fusion polypeptide. In another embodiment, such an analog exhibits an increased serum half-life compared to a corresponding pre-modified antibody, antigen-binding antibody fragments and fusion polypeptide. For example, among the analogs of the invention are analogs of the monoclonal antibody produced hybridoma 4E7 (ATCC® Accession No. PTA-5109), or by hybridoma 7A11 (ATCC® Accession No. PTA-5110), or by hybridoma 7C6 (ATCC® Accession No. PTA-5111), or by hybridoma 7F10 (ATCC® Accession No. PTA-5112), or by hybridoma 7G10 (ATCC® Accession No. PTA-5245), or by hybridoma 7H1 (ATCC® Accession No. PTA-5114), or by hybridoma 8A1 (ATCC® Accession No. PTA-5115), or by hybridoma 8B5 (ATCC® Accession No. PTA-5116), or by hybridoma 8C3 (ATCC® Accession No. PTA-5246), or by hybridoma 8E3 (ATCC® Accession No. PTA-5118), or by hybridoma 8G9 (ATCC® Accession No. PTA-5119), or by hybridoma 15C9 (ATCC® Accession No. PTA-5106), or by hybridoma 16C7 (ATCC®

Accession No. PTA-5107), or by hybridoma 16H9 (ATCC® Accession No. PTA-5108), or by hybridoma 117.1 (ATCC® Accession No. PTA-4567), or by hybridoma 325.1 (ATCC® Accession No. PTA-5120), or by hybridoma 368.1 (ATCC® Accession No. PTA-4568), or by hybridoma 446.1 (ATCC® Accession No. PTA-5549), or by hybridoma 501.1 (ATCC® Accession No. PTA-4569), or by hybridoma 621.1 (ATCC® Accession No. PTA-5121), or by hybridoma 633.1 (ATCC® Accession No. PTA-5122), or by hybridoma 654.1 (ATCC® Accession No. PTA-5247), or by hybridoma 725.1 (ATCC® Accession No. PTA-5124), or by hybridoma 776.1 (ATCC® Accession No. PTA-4570).

In another aspect, the present invention provides a pharmaceutical composition comprising an antibody, an antigen-binding antibody fragment, fusion polypeptide, or analog of the invention, that is, one that preferentially binds cell-associated CA 125/O772P polypeptide relative to shed CA 125/O772P polypeptide, and a pharmaceutically acceptable carrier. In still another aspect, the present invention provides a method of preparing a pharmaceutical composition comprising admixing an antibody or antigen-binding antibody fragment of the invention with a pharmaceutically acceptable carrier.

In still another aspect, the present invention provides an article of manufacture comprising packaging material and a pharmaceutical composition of the invention contained within the packaging material, said pharmaceutical composition in a form suitable for administration to a subject, preferably a human. In one embodiment, the article of manufacture further comprises printed instructions and/or a label regarding the use or administration of the pharmaceutical composition. The instructions and/or label can, for example, suggest a dosing regimen for the prevention or treatment of one or more symptoms of a CA 125/O772P-related disorder, such as a cell proliferative disorder, for example cancer, e.g., ovarian, uterine, breast, or lung cancer.

In another aspect, the present invention provides methods for preventing, treating, managing or ameliorating a symptom of a CA 125/O772P-related disorder, comprising: administering to a subject in need of such prevention, treatment, management, or amelioration, an antibody or antigen-binding fragment of an antibody in an amount sufficient to prevent, treat, manage, or ameliorate a symptom of the cell proliferative disorder, wherein said antibody or antigen-binding antibody fragment preferentially binds cell-associated CA 125/O772P relative to shed CA 125/O772P.

In one embodiment, such methods of the invention relate to prevention, treatment, management, or amelioration of a symptom of a cell proliferative disorder. In another embodiment, such methods of the invention relate to prevention, treatment, management, or amelioration of a symptom of a cancer. In yet another embodiment, such methods of the invention relate to prevention, treatment, management, or amelioration of a symptom of cervical cancer, uterine cancer, breast cancer or lung cancer. In a preferred embodiment of such methods of the invention, such methods relate to prevention, treatment, management, or amelioration of a symptom of ovarian cancer.

In one embodiment of such methods of the invention, the antibody or antigen-binding fragment administered is a monoclonal antibody or antigen-binding monoclonal antibody fragment. In another embodiment of the methods of the invention, the antibody or antigen-binding antibody fragment is administered at a dosage concentration of from about 5 µg/kg to about 10 mg/kg, preferably from about 20 µg/kg to about 5 mg/kg, and more preferably from about 100 µg/kg to about 5 mg/kg.

In yet another embodiment of such methods of the invention, the methods are practiced as part of a combination cancer therapy. Such combination cancer therapy can include, for example, administration of a chemotherapeutic agent, e.g., paclitaxel or cisplatin. Such combination cancer therapy can alternatively include, but is not limited to, radiation therapy.

In still another aspect, the present invention provides a method to assist in identifying an antibody or antigen-binding antibody fragment that preferentially binds cell-associated CA 125/O772P relative to shed CA 125/O772P. In one embodiment, a method to assist in identifying an antibody or antigen-binding antibody fragment that preferentially binds cell-associated CA 125/O772P comprises contacting an antibody or antigen-binding antibody fragment with a peptide comprising cell-associated CA 125/O772P (e.g., a cell-associated CA125/O772P polypeptide or even the full length CA125/O772P polypeptide) in the presence of shed CA 125/O772P (preferably an excess amount (weight/weight) of shed) under conditions that allow binding of the antibody or antigen-binding antibody fragment to either said peptide comprising cell-associated CA 125/O772P or shed CA 125/O772P. After incubating, the shed CA 125/O772P (with or without antibody or antigen-binding antibody fragment bound) and unbound antibody or antigen-binding antibody fragment are removed, and the amount of antibody or antigen-binding antibody fragment bound to the peptide comprising cell-associated CA 125/O772P is measured. If the antibody or antigen-binding antibody fragment from such method satisfies any one of the three embodiments set forth above for "preferentially binds," then said antibody, or antigen-binding antibody fragment, is one that preferentially binds cell-associated CA 125/O772P polypeptide relate to shed CA 125/O772P polypeptide. In a preferred embodiment, the ratio of shed CA 125/O772P to cell-associated CA 125/O772P in the reaction mixture is about 25:1 (wt/wt). As part of this method, cell-associated CA 125/O772P can be immobilized on a solid surface. For example, the method can be performed in an ELISA format.

In still another embodiment, the invention provides a method to assist in identifying an antibody, or antigen-binding antibody fragment, that preferentially binds cell-associated CA 125/O772P relative to shed CA 125/O772P comprises contacting the antibody, or antigen-binding fragment, with a peptide comprising cell-associated CA 125/O772P and shed CA 125/O772P (preferably an excess amount (weight/weight) of shed), e.g., about a 25-fold excess amount (wt/wt), under conditions that allow binding of the peptide comprising cell-associated CA 125/O772P to the antibody or antigen-binding antibody fragment, removing unbound peptide comprising cell-associated CA 125/O772P, measuring the amount of peptide comprising cell-associated CA 125/O772P bound by the antibody, or antigen-binding fragment, and comparing the amount measured to the amount of peptide comprising cell-associated CA 125/O772P the antibody or antigen-binding antibody fragment can bind in the absence of such amount of shed CA 125/O772P (i.e., a lesser amount). If the antibody or antigen-binding antibody fragment from such method satisfies any one of the three embodiments set forth above for "preferentially binds," then said antibody or antigen-binding antibody fragment is one that preferentially binds cell-associated CA 125/O772P polypeptide relative to shed CA 125/O772P polypeptide. As part of this method the antibody, or antigen-binding antibody fragment can be immobilized on a solid surface, for example, the method can be performed in an ELISA format.

In yet another embodiment, the invention provides a method to assist in identifying an antibody, or antigen-binding antibody fragment, that preferentially binds cell-associated CA 125/O772P comprises contacting the antibody, or antigen-binding fragment, with a cell that expresses CA 125/O772P and with an amount, e.g., at least about 0.05 mg/ml, of shed CA 125/O772P (preferably an excess of amount (wt/wt) of shed) under conditions that allow binding of the CA 125/O772P to the antibody or antigen-binding antibody fragment, removing unbound cells, measuring the amount of cells expressing CA 125/O772P bound by the antibody, or antigen-binding fragment, and comparing the amount measured to the amount of cells expressing CA 125/O772P that binds the antibody or antigen-binding antibody fragment in the absence of such amount of (i.e., a lesser amount) shed CA 125/O772P. If the antibody or antigen-binding antibody fragment from such method satisfies any one of the three embodiments set forth above for "preferentially binds," then said antibody or antigen-binding antibody fragment is one that preferentially binds cell-associated CA 125/O772P polypeptide relative to shed CA 125/O772P polypeptide. Such a method can, for example, be performed wherein the measuring is performed by flow cytometry techniques, including, e.g., fluorescence activated cell sorting (FACS).

In another aspect, the present invention also provides methods for diagnosing a CA 125/O772P-related disorder or predisposition to a CA 125/O772P-related disorder.

3.1. Terminology

As used herein, the term "analog" in the context of an antibody or antigen-binding antibody fragment or fusion polypeptide of the invention refers to an antibody, antigen-binding antibody fragment or fusion polypeptide that is modified relative to a corresponding antibody, antigen-binding antibody fragment or fusion polypeptide of the invention (referred to in, this context as a "pre-modified" antibody, antigen-binding antibody fragment or fusion polypeptide of the invention) prior to the modification present in the analog, but which still preferentially binds cell-associated CA 125/O772P relative to shed CA 125/O772P.

"Affinity" ($K_d$) of an antibody or antigen-binding antibody fragment of the invention is determined by the affinity assay described in Section 6.4, below.

The term "antibody of the invention," as used herein, refers to an antibody that preferentially binds cell-associated CA 125/O772P polypeptide relative to shed CA 125/O772P polypeptide. Likewise, the term "antigen-binding antibody fragment of the invention," as used herein, refers to an antigen-binding antibody fragment that preferentially binds cell-associated CA 125/O772P polypeptide relative to shed CA 125/O772P polypeptide. An antibody or antigen-binding antibody fragment is considered an antibody or antigen binding fragment of the invention even if it binds a CA 125/O772P polypeptide, i.e., a pre-shed CA 125/O772P polypeptide, as long as such antibody or antigen-binding antibody fragment nonetheless preferentially binds cell-associated CA 125/O772P relative to shed CA 125/O772P. Due to the fact, as discussed below, that cell-associated CA 125/O772P, prior to CA 125/O772P shedding, is present as part of pre-shed CA 125/O772P, it is noted that antibodies that preferentially bind cell-associated CA 125/O772P can also bind pre-shed CA 125/O772P. Thus, independently of whether or not an antibody or antigen-binding antibody fragment binds CA 125/O772P, it is considered an antibody or antigen-binding antibody fragment of the invention so long as it satisfies the criteria set forth herein for "preferentially binds CA 125/O772P polypeptide relative to shed CA 125/O772P." It is further noted that, unless otherwise indicated, the terms "antibody" and "immunoglobulin" are utilized interchangeably.

The term "Antibody-Dependent Cellular Cytotoxicity assay" (ADCC assay) as used herein, refers to the ADCC assay described in Section 6.5, below. As such, an antibody or antigen-binding antibody fragment that mediates lysis of CA 125/O772P-positive tumor cells in an ADCC assay is one that is considered positive when tested in the ADCC assay described in Section 6.5, below.

The term "about," as used herein, unless otherwise indicated, refers to a value that is no more than 10% above or below the value being modified by the term. In the event a nucleic acid or amino acid sequence length is the value being modified, the resulting modified value will be an integer that is no more than 10% above or below the original length. Further, instances wherein 10% of the length being modified by this term results in a value that must be less than 1, then it is understood that, as used herein, that the modified length is 1 nucleotide or amino acid residue more or less than the original value.

As used herein, the term "binds to" in the context of antibody-antigen binding, e.g., in the context of an antibody or antigen-binding antibody fragment that preferentially binds cell-associated CA 125/O772P, refers to antibodies or antigen-binding antibody fragments that specifically bind to a particular antigen (e.g., cell-associated CA 125/O772P) and do not specifically bind to other antigens. Preferably, an antibody or antigen-binding antibody fragment is one that binds CA 125/O772P with a specificity of at least 5 OD/microgram of antibody as determined by an ELISA Specificity Assay, or is considered positive in a Flow Cytometry Specificity Assay. A peptide or polypeptide that binds to an antigen may bind to other peptides or polypeptides with lower affinity as determined by, e.g., immunoassays, BIAcore, Scatchard analysis or other assays known in the art. Antibodies or fragments that specifically bind to an antigen may be cross-reactive with related antigens. Preferably, antibodies or fragments that bind to an antigen do not cross-react with other antigens. See, e.g., *Fundamental Immunology Second Edition*, Paul, ed., Raven Press (1989) at pages 332-336 for a discussion regarding antibody specificity. Preferably, an antibody or antigen-binding antibody fragment of the invention is one that binds the peptide of FIG. 1 with a $K_d$ of less than about 100 nM, and more preferably binds the peptide of FIG. 1 with a $K_d$ of less than about 5 nM, all as measured by the BIAcore Affinity Assay, which is described in Section 6.4. It is noted that an antibody that preferentially binds cell-associated CA 125/O772P may yet also represent an antibody that specifically binds CA 125/O772P, including shed CA 125/O772P, relative to other, non-CA 125/O772P antigens. Finally, it is noted that the terms "specifically" and "immunospecifically," as used herein, unless otherwise noted, are used interchangeably.

ELISA Specificity Assay: This assay, as used herein, refers to the ELISA assay described in Section 6.2, below. An antibody (or antigen-binding antibody fragment) is considered positive in this assay (i.e., is specific for CA 125/O772P) if it exhibits an absorbance of at least 5 to greater than 30 OD/microgram antibody.

Flow Cytometry Specificity Assay: This assay, as used herein, refers to the flow cytometry assay described in Section 6.2, below. Antibodies (or antigen-binding antibody fragments) are considered positive (i.e., are specific for CA 125/O772P) if they exhibit a Flow Cytometry Specificity Assay result within the following positive cell ranges: less than 5% positive NIH/3T3 cells, and at least 60% positive NIH/3T3 cells producing a SEQ ID NO:2 polypeptide; and/or less than 25% positive SK-OV3 cells and at least 80% positive OVCAR-3 cells.

The terms "competes for binding," and "competes with" as used herein the context of two antibody species or antigen-binding antibody fragment species (or combinations thereof) are used interchangeably. A first antibody or antigen-binding antibody fragment is considered to compete with a second antibody or antigen-binding antibody fragment if the first antibody or antigen-binding antibody fragment competes with the second in an ELISA Cross-Competition Assay and/or a FACS Cross-Competition Assay.

ELISA Cross-Competition Assay: This assay, as used herein, refers to the ELISA assay described in Section 7.0, below. An antibody or antigen-binding antibody fragment is considered to compete for binding in this assay if the $IC_{50}$ for the competitor antibody or antigen-binding antibody fragment is a concentration no more than about 100-fold above the concentration of the antibody or antigen-binding antibody fragment.

FACS Cross-Competition Assay: This assay, as used herein, refers to the FACS assay described in Section 7.0, below. An antibody or antigen-binding antibody fragment is considered to compete for binding in this assay if the $IC_{50}$ for the competitor antibody or antigen-biding antibody fragment is a concentration no more than about 100-fold above the concentration of the antibody or antigen-binding antibody fragment.

The term "CA 125/O772P" or "CA 125/O772P polypeptide," as used herein refers to the pre-shed CA 125/O772P, transmembrane polypeptide that, once shed, yields shed CA 125/O772P polypeptide and cell-associated CA 125/O772P polypeptide. The amino acid sequence reported in the literature as the full-length sequence of CA 125/O772P polypeptide has recently been shown to not, in fact, represent the full-length CA 125/O772P sequence. In particular, see, e.g., WO 02/06317 (PCT/US01/22635), and US 2003/0124140, which disclose a polypeptide referred to as "O772P." The amino acid sequence of O772P includes an extension over what was previously thought to be full-length CA 125. Because the polypeptide is referred to in the art as CA 125 or as O772P, it is referred to herein as "CA 125/O772P."

As used herein, the term "CA 125/O772P-related disorder" refers to a disorder that involves or is characterized by the presence of a differential level of cell-associated CA 125/O772P relative to a corresponding normal state and/or an overabundance of shed CA 125/O722P relative to a corresponding normal state. For example, in the case of ovarian cancer, a higher level of cell-associated or shed CA 125/O772P is observed relative to the level observed in a normal (e.g., non-cancerous) state. The differential level of cell-associated and/or shed CA 125/O772P can either be causative or indicative of the disorder.

As used herein, the term "cell-associated CA 125/O772P" refers to a CA 125/O772P extracellular polypeptide species that remains in cell-associated form however transiently, e.g., prior to turn-over, after a portion of the pre-shed CA 125/O772P polypeptide is released as shed CA 125/O772P. For example, a cell-associated CA 125/O772P species is a CA 125/O772P extracellular polypeptide species that remains in cell-associated form on the surface of OVCAR-3 cell line cells (HTB-161; ATCC®) or human ascites cells after a portion of the CA 125/O772P polypeptide is released as shed CA 125/O772P. A CA 125/O772P cell-associated polypeptide species is present within amino acid residues 1 to 708 of SEQ ID NO:1 and within amino acid residues 1 to 711 of SEQ ID NO:2. Moreover, CA 125/O772P may be cleaved at a protease cleavage site located at amino acid residues 659-665 of SEQ ID NO:2. See O'Brien et al., Tumour Biol. 23(3):154-169 (2002). As such, a cell-associated CA 125/O772P polypeptide may include amino acid residues 659-711 of SEQ ID NO:2.

The term "Complement-Dependent Cytotoxicity assay" (CDC Assay) as used herein refers to the CDC assay described in Section 6.5, below. As such, an antibody or antigen-binding antibody fragment that mediates tumor cell lysis in a CDC assay is one that is considered positive when tested in the CDC assay described in Section 6.5, below.

As used herein, the terms "disorder" and "disease" are used interchangeably to refer to a condition in a subject.

As used herein, the term "fragment" in the phrase "antigen-binding antibody fragment" refers to a peptide or polypeptide comprising an amino acid sequence of at least about 5 contiguous amino acid residues, at least about 10 contiguous amino acid residues, at least about 15 contiguous amino acid residues, at least about 20 contiguous amino acid residues, at least about 25 contiguous amino acid residues, at least about 40 contiguous amino acid residues, at least about 50 contiguous amino acid residues, at least about 60 contiguous amino acid residues, at least about 70 contiguous amino acid residues, at least about 80 contiguous amino acid residues, at least about 90 contiguous amino acid residues, at least about 100 contiguous amino acid residues, at least about 110 contiguous amino acid residues, or at least about 120 contiguous amino acid residues, of the amino acid sequence of another polypeptide, e.g., an antibody that preferentially binds cell-associated CA 125/O772P.

The term "host cell" as used herein refers to the particular cell, including a mammalian cell or other eukaryotic cells, or prokaryotic cells, said cells, for example, transformed or transfected with a nucleic acid molecule or infected with viruses, phagemid or bacteriophage and the progeny or potential progeny of such a cell. Progeny of such a cell may not be identical to the parent cell transfected with the nucleic acid molecule due to mutations or environmental influences or additional recombinant manipulations that may occur in succeeding generations or integration of the nucleic acid molecule into the host cell genome.

As used herein, the term "hybridizes under stringent conditions" describes conditions for hybridization and washing under which nucleotide sequences at least 75% identical to each other typically remain hybridized to the complement of each other. Such stringent conditions are known to those skilled in the art and can be found in *Current Protocols in Molecular Biology*, Ausubel et al., eds., John Wiley & Sons (1989-2002) at sections 6.3.1-6.3.6. In one, non-limiting example stringent hybridization conditions are hybridization at 6× sodium chloride/sodium citrate (SSC) at about 45° C., followed by one or more washes in 0.1×SSC, 0.2% SDS at about 68° C. In a preferred, non-limiting example stringent hybridization conditions are hybridization in 6×SSC at about 45° C., followed by one or more washes in 0.2×SSC, 0.1% SDS at 50-65° C. (i.e., one or more washes at 50° C., 55° C., 60° C. or 65° C.). It is understood that in certain embodiments the nucleic acids of the invention do not include nucleic acid molecules that hybridize under these conditions solely to a nucleotide sequence consisting of only A or T nucleotides.

As used herein, the term "isolated" in the context of a peptide, polypeptide, fusion protein, antibody or antigen-binding antibody fragment refers to a peptide, polypeptide, fusion protein, antibody or antigen-binding antibody fragment which is substantially free of cellular material or contaminating proteins from the cell or tissue source from which it is derived or obtained, or substantially free of chemical precursors or other chemicals when chemically synthesized. The language "substantially free of cellular material or contaminating protein" includes preparations of a peptide, polypeptide, fusion protein, antibody or antigen-binding antibody fragment in which the peptide, polypeptide, fusion protein, antibody or antigen-binding antibody fragment is separated from cellular components of the cells from which it is isolated or recombinantly produced. Thus, a peptide, polypeptide, fusion protein, antibody or antigen-binding antibody fragment that is substantially free of cellular material or contaminating protein includes preparations of a peptide, polypeptide, fusion protein, antibody or antigen-binding antibody fragment having less than about 30%, about 20%, about 10%, or about 5% (by dry weight) of other protein. When the peptide, polypeptide, fusion protein, antibody or antigen-binding antibody fragment is recombinantly produced, it is also preferably substantially free of culture medium, i.e., culture medium represents less than about 20%, about 10%, or about 5% of the volume of the protein preparation. When the peptide, polypeptide, fusion protein, antibody or antigen-binding antibody fragment is produced by chemical synthesis, it is preferably substantially free of chemical precursors or other chemicals, i.e., it is separated from chemical precursors or other chemicals which are involved in the synthesis of the peptide, polypeptide, fusion protein, antibody or antigen-binding antibody fragment. Accordingly, such preparations of a peptide, polypeptide, fusion protein, antibody or antigen-binding antibody fragment have less than about 30%, about 20%, about 10%, about 5% (by dry weight) of chemical precursors or compounds other than the peptide, polypeptide, fusion protein, antibody or antigen-binding antibody fragment of interest.

As used herein, the term "isolated" in the context of nucleic acid molecules refers to a nucleic acid molecule which is separated from other nucleic acid molecules which are present in the natural cellular source of the nucleic acid molecule. Alternatively, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the terms "manage," "managing" and "management" refer to the beneficial effects that a subject derives from an agent, e.g., an antibody, antigen-binding antibody fragment, fusion polypeptide or analog of the invention, which does not result in a cure of the disease. In certain embodiments, a subject is administered one or more such agents to "manage" a disorder so as to prevent or slow the progression or worsening of the disorder.

As used herein, the term "monoclonal antibody" refers to an antibody that is derived from a single cellular clone, including any eukaryotic, prokaryotic, or phage clone, and is not dependent upon the method by which it is produced. Therefore, a "monoclonal antibody" can refer to a composition comprising a population of antibodies that each bind to a single epitope wherein said composition lacks antibodies that bind a different epitope than the single epitope to which the population of antibodies bind. It is noted, of course, that in certain instances, a single epitope is present in a polypeptide at multiple positions. In such instances, although the monoclonal antibody may bind to multiple positions, it is, nonetheless, still considered to be binding to a single epitope.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably are double-stranded DNA.

The term "operably linked" as used herein the context of a fusion polypeptide refers to any covalent or non-covalent interaction that connects the antibody or antigen-binding antibody fragment to the heterologous agent. The operable linkage can be direct or indirect. For example, an amino acid sequence can be present between the antibody (or antigen-binding antibody fragment) and the heterologous agent.

As used herein, an antibody, antigen-binding antibody fragment, fusion polypeptide, or analog that "preferentially binds cell-associated CA 125/O772P," "preferentially binds cell-associated CA 125/O772P polypeptide," "preferentially binds cell-associated CA 125/O772P relative to shed CA 125/O772P" or "preferentially binds CA 125/O772P polypeptide relative to shed CA 125/O772P polypeptide" refers to an antibody or antigen-binding antibody fragment that is positive when tested in an ELISA Competition Assay or a Flow Cytometry Competition Assay, as described herein. Preferably, the antibody or antigen-binding antibody fragment is one that is positive in both an ELISA Competition Assay and a Flow Cytometry Competition Assay, as described herein.

ELISA Competition Assay: This assay, as used herein, refers to the ELISA assay described in Section 6.3, below. An antibody (or antigen-binding antibody fragment) is considered positive in this assay (that is, preferentially binds cell-associated CA 125/O772P) if it exhibits less than about 25% inhibition of binding at 25-fold w/w excess of shed CA 125/O772P over the peptide of FIG. 1 (SEQ ID NO: 1).

Flow Cytometry Competition Assay: This assay, as used herein, refers to the flow cytometry assay described in Section 6.3, below. An antibody (or antigen-binding antibody fragment) is considered positive (that is, is considered to preferentially bind cell-associated CA 125/O772P) if it exhibits an $IC_{50}$, as measured by percent-positive cells, of at least 0.05 mg/ml shed CA 125/O772P, that is, if it requires at least 0.05 mg/ml shed CA 125/O772P to reduce the percent-positive cells in the Flow Cytometry Competition Assay by half.

As used herein, the terms "prevent", "preventing" and "prevention" refer to the impedition of the recurrence or onset of a CA 125/O772P-related disorder or one or more symptoms of a CA 125/O772P-related disorder in a subject.

A used herein, a "protocol" includes dosing schedules and dosing regimens. The protocols herein are methods of use and include prophylactic and therapeutic protocols.

As used herein, the term "shed CA 125/O772P polypeptide" refers to a CA 125/O772P extracellular polypeptide sequence that becomes separated and released from CA 125/O772P polypeptides expressed on the surface of cells expressing CA 125/O772P, leaving a cell-associated CA 125/O772P species remaining on the cell surface, however transiently. The term, as used herein, refers to a species of shed CA 125/O772P found in human serum and/or OVCAR-3 (HTB-161; ATCC) cell line culture supernatant. Such shed CA 125/O772P polypeptides can be obtained via the protocol of de los Frailes et al., Tumour Biol. 14(1):18-29 (1993), using human ascites or OVCAR-3 supernatants. Alternatively, shed CA 125/O772P polypeptides can be obtained via commercial sources such as Fitzgerald Industries International (Concord, Mass.), Scripps Laboratories (La Jolla, Calif.), or United States Biochemical Corp (Cleveland, Ohio).

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee, and a human), preferably a human. In one embodiment, the subject is a subject with cancer, for example, ovarian cancer.

As used herein, the terms "treat", "treatment" and "treating" refer to the amelioration of a CA 125/O772P-related disorder that results from the administration of one or more antibodies, antigen-binding antibody fragments, fusion polypeptides or analogs.

The term "pharmaceutically acceptable" as used herein means a composition, e.g., a carrier, excipient, or salt, approved by a regulatory agency of the Federal or a state government or listed in the U.S. Pharmacopoeia or other generally recognized pharmacopoeia for use in animals, and more particularly, in humans.

4. BRIEF DESCRIPTION OF THE DRAWINGS

FIG. 1: Depicts the amino acid sequence of CA 125/O772P 3-repeat (SEQ ID NO:1). Italicized residues from amino acid 14 to amino acid 452 represent repeat regions. Each of the three repeats within the 14-452 repeat region are delineated by vertical lines and arrows as shown. Underlined residues represent the transmembrane-proximal non-repeat region. The sequence that follows the underlined residues is not part of CA 125/O772P and includes a carboxy-Myc-His tag.

FIG: 2: Depicts the amino acid sequence of CA 125/O772P 3-repeat TM (SEQ ID NO:2). Italicized, underlined residues, i.e., from amino acid 14 to amino acid 452, represent repeat regions. Each of the three repeats within the 14-452 repeat region are delineated by vertical lines and arrows as shown. Underlined non-italicized residues, i.e., from amino acid 453 to amino acid 711, represent the transmembrane-proximal non-repeat region. Non-underlined italicized residues, i.e., from amino acid 712 to amino acid 738, represent the transmembrane domain. Residues in bold, from amino acid 739 to amino acid 769, represent a cytoplasmic region. The sequence that follows the bold residues is not part of CA 125/O772P and includes a carboxy-Myc-His tag.

FIG. 3: Shows a representative plot from a FACS competition assay of shed CA 125/O772P concentrations versus percent positive cells for, in this instance, 117.1 antibody and M11 antibody control (squares). As shown, M11 can be competed for binding to OVCAR-3 cells even at low concentrations of shed CA 125/O772P ($IC_{50}$=0.003 mg/ml) while 117.1 cannot be competed, even at high concentrations of shed CA 125/O772P ($IC_{50}$ greater than 1 mg/ml).

Figure 4:
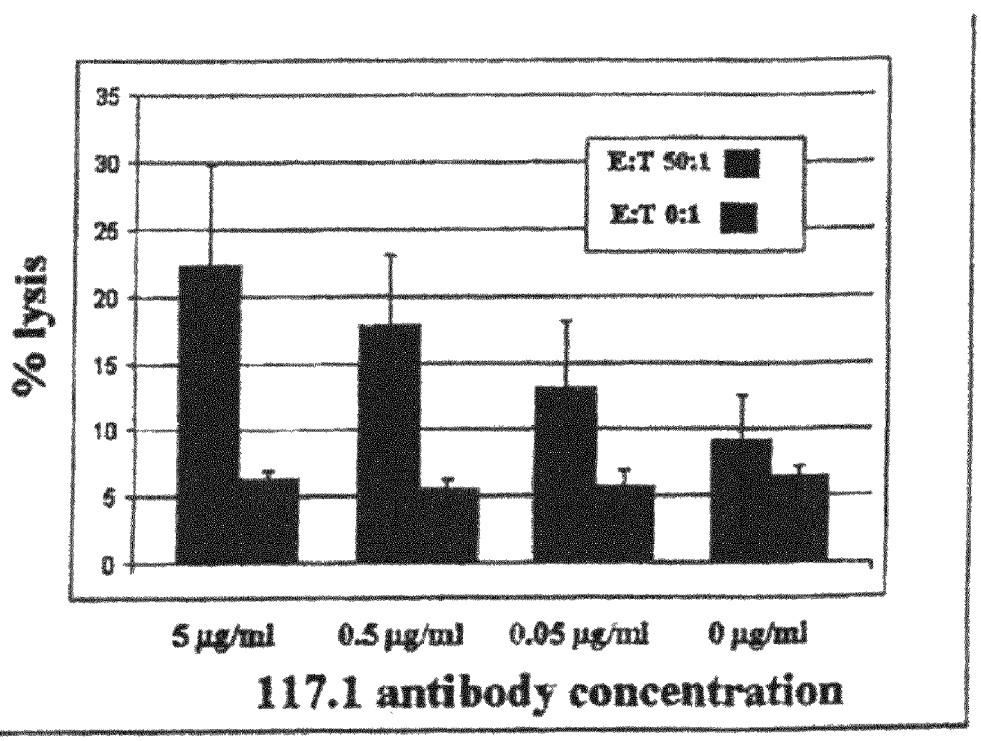

FIG. 4: Shows a representative plot from an ADCC assay of percent lysis versus antibody concentration for 117.1 antibody (average of 4 separate donors). As shown in the figure, antibody 117.1 mediates specific lysis of OVCAR-3 cells in a dose-dependent manner.

FIG. 5A: Depicts the nucleotide sequence (SEQ ID NO:35) that encodes the variable light chain region of monoclonal antibody 117.1. The nucleotide sequence that encodes leader sequence is double underlined, and the nucleotide sequences that encode CDR sequences are single underlined.

FIG. 5B: Depicts the nucleotide sequence (SEQ ID NO:36) that encodes the variable heavy chain region of monoclonal antibody 117.1. The nucleotide sequence that encodes leader sequence is double underlined, and the nucleotide sequences that encode CDR sequences are single underlined.

FIG. 5C: Depicts the amino acid sequence (SEQ ID NO:27) of the variable light chain region of monoclonal antibody 117.1. Leader sequence is double underlined, and CDR sequences are single underlined.

FIG. 5D: Depicts the amino acid sequence (SEQ ID NO:28) of the variable heavy chain region of monoclonal antibody 117.1. Leader sequence is double underlined, and CDR sequences are single underlined.

FIG. 6A: Depicts the nucleotide sequence (SEQ ID NO:37) that encodes the variable light chain region of monoclonal antibody 368.1. The nucleotide sequence that encodes leader sequence is double underlined, and the nucleotide sequences that encode CDR sequences are single underlined.

FIG. 6B: Depicts the nucleotide sequence (SEQ ID NO:38) that encodes the variable heavy chain region of monoclonal antibody 368.1. The nucleotide sequence that encodes leader sequence is double underlined, and the nucleotide sequences that encode CDR sequences are single underlined.

FIG. 6C: Depicts the amino acid sequence (SEQ ID NO:29) of the variable light chain region of monoclonal antibody 368.1. Leader sequence is double underlined, and CDR sequences are single underlined.

FIG. 6D: Depicts the amino acid sequence (SEQ ID NO:30) of the variable heavy chain region of monoclonal antibody 368.1. Leader sequence is double underlined, and CDR sequences are single underlined.

FIG. 7A: Depicts the nucleotide sequence (SEQ ID NO:39) that encodes the variable light chain region of monoclonal antibody 501.1. The nucleotide sequence that encodes leader sequence is double underlined, and the nucleotide sequences that encode CDR sequences are single underlined.

FIG. 7B: Depicts the nucleotide sequence (SEQ ID NO:40) that encodes the variable heavy chain region of monoclonal antibody 501.1. The nucleotide sequence that encodes leader sequences are double underlined, and the nucleotide sequences that encode CDR sequences are single underlined.

FIG. 7C: Depicts the amino acid sequence (SEQ ID NO:31) of the variable light chain region of monoclonal antibody 501.1. Leader sequence is double underlined, and CDR sequences are single underlined.

FIG. 7D: Depicts the amino acid sequence (SEQ ID NO:32) of the variable heavy chain region of monoclonal antibody 501.1. Leader sequences is double underlined, and CDR sequences are single underlined.

FIG. 8A: Depicts the nucleotide sequence (SEQ ID NO:41) that encodes the variable light chain region of monoclonal antibody 776.1. The nucleotide sequence that encodes leader sequence is double underlined, and the nucleotide sequences that encode CDR sequences are single underlined.

FIG. 8B: Depicts the nucleotide sequence (SEQ ID NO:42) that encodes the variable heavy chain region of monoclonal antibody 776.1. The nucleotide sequences that encode leader sequences is double underlined, and the nucleotide sequences that encode CDR sequences are single underlined.

FIG. 8C: Depicts the amino acid sequence (SEQ ID NO:33) of the variable light chain region of monoclonal antibody 776.1. Leader sequence is double underlined, and CDR sequences are single underlined.

FIG. 8D: Depicts the amino acid sequence (SEQ ID NO:34) of the variable heavy chain region of monoclonal antibody 776.1. Leader sequence is double underlined, and CDR sequences are single underlined.

FIG. 9A: Depicts the nucleotide sequence (SEQ ID NO:52) that encodes the variable light chain region of monoclonal antibody 725.1. The nucleotide sequence that encodes leader sequence is double underlined, and the nucleotide sequences that encode CDR sequences are single underlined.

FIG. 9B: Depicts the nucleotide sequence (SEQ ID NO:57) that encodes the variable heavy chain region of monoclonal antibody 725.1. The nucleotide sequences that encode leader sequences is double underlined, and the nucleotide sequences that encode CDR sequences are single underlined.

FIG. 9C: Depicts the amino acid sequence (SEQ ID NO:54) of the variable light chain region of monoclonal antibody 725.1. Leader sequence is double underlined, and CDR sequences are single underlined.

FIG. 9D: Depicts the amino acid sequence (SEQ ID NO:53) of the variable heavy chain region of monoclonal antibody 725.1. Leader sequence is double underlined, and CDR sequences are single underlined.

FIG. 10A: Depicts the nucleotide sequence (SEQ ID NO:59) that encodes the variable light chain region of monoclonal antibody 16H9. The nucleotide sequence that encodes leader sequence is double underlined, and the nucleotide sequences that encode CDR sequences are single underlined.

FIG. 10B: Depicts the nucleotide sequence (SEQ ID NO:58) that encodes the variable heavy chain region of monoclonal antibody 16H9. The nucleotide sequences that encode leader sequences is double underlined, and the nucleotide sequences that encode CDR sequences are single underlined.

FIG. 10C: Depicts the amino acid sequence (SEQ ID NO:56) of the variable light chain region of monoclonal antibody 16H9. Leader sequence is double underlined, and CDR sequences are single underlined.

FIG. 10D: Depicts the amino acid sequence (SEQ ID NO:55) of the variable heavy chain region of monoclonal antibody 16H9. Leader sequence is double underlined, and CDR sequences are single underlined.

Figure 11:
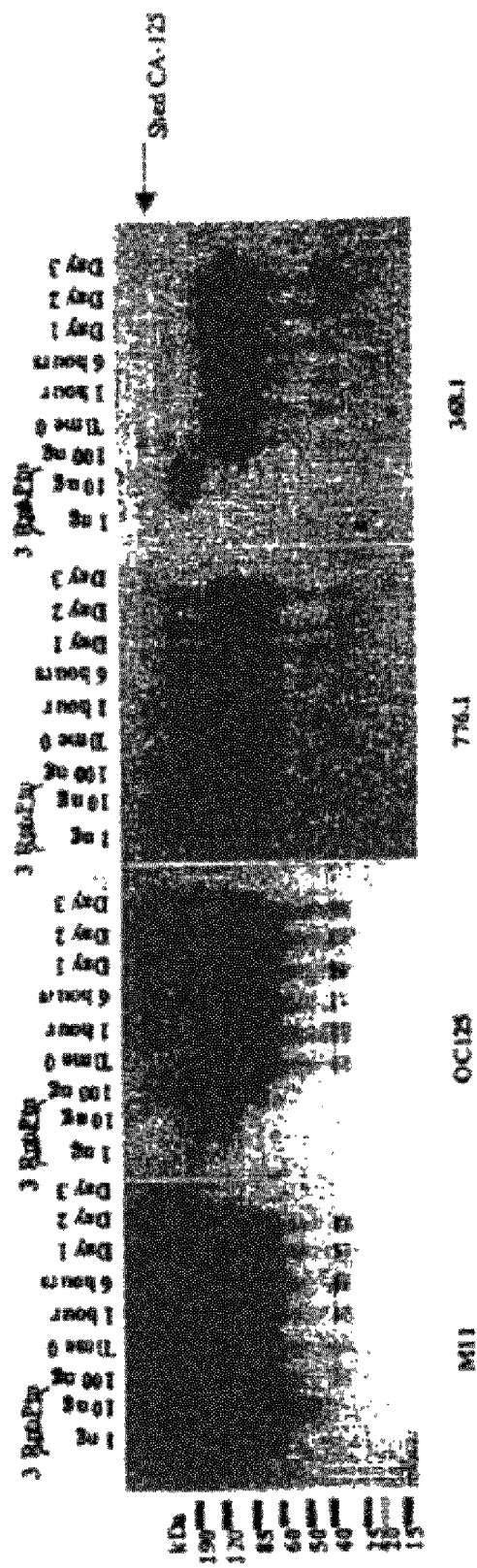

FIG. 11: Depicts the results of a western blot analysis of OVCAR-3 supernatents. Antibody concentration and detection are indicated in the working example presented, below, in Section 6.7. "3 Rpt Ptn" in each blot refers to lanes containing O772P 3-repeat recombinant polypeptide; the remainder of the lanes in each blot contain OVCAR-3 conditioned or control media. The particular antibody tested is indicated at the bottom of each blot (i.e., M11, OC125, 776.1 and 368.1 antibodies). Molecular weight markers are indicated on left of figure.

Figure 12:
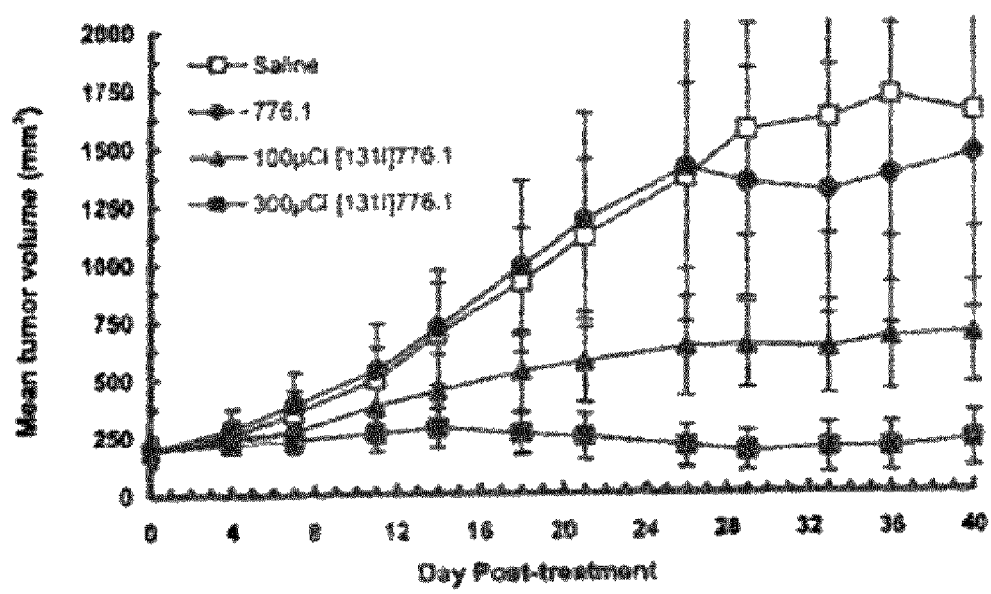

FIG. 12: In vivo evaluation of $^{131}$I-labeled 776.1. NCR nu/nu mice bearing OVCAR-3 tumors were treated with either saline, 100 µCi [$^{131}$I]776.1 IgG1, 300 µCi [$^{131}$I]776.1 IgG1, or 17 µg unlabeled 776.1 IgG1 (same protein dose as in the 300 µCi [$^{131}$I]776.1 IgG1 group). Treatment was a single dose administered intravenously on day 0. The specific activity of [$^{131}$I]776.1 was 15 mCi/mg with an immunoreactivity of 51% post-labeling. Results are shown as mean tumor volume+/−SD for 10 mice total per group. Mean tumor size at the beginning of treatment was 199 mm$^3$ for all groups.

5. DETAILED DESCRIPTION OF THE INVENTION

The present invention is based, in part, on the recognition that the events that produce shed CA 125/O772P also leave a portion of the extracellular region of the CA 125/O772P amino acid sequence in cell-associated form, i.e., also yield cell-associated CA 125/O772P. The invention described in detail herein is based, in part, on the recognition that antibodies, and antigen-binding antibody fragments, fusion polypeptides and analogs that preferentially bind cell-associated CA 125/O772P relative to shed CA 125/O772P can be generated, and that such antibodies, antigen-binding antibody fragments, fusion polypeptides and analogs can, for example, be utilized to prevent, manage, treat, or ameliorate a CA 125/O772P-related disorder or one or more symptoms of a CA 125/O772P-related disorder such as a cell proliferative disorder, for example, cancer, e.g., ovarian cancer.

As discussed throughout, the antibodies and antigen-binding antibody fragments of the invention are those that preferentially bind cell-associated CA 125/O772P. Likewise the fusion polypeptides and analogs of the invention also preferentially bind cell-associated CA 125/O772P. As also noted herein, due to the fact that cell-associated CA 125/O772P, prior to CA 125/O772P shedding, is present as part of pre-shed CA 125/O772P, it is noted that antibodies, antigen-binding antibody fragments, fusion polypeptides, and analogs of the invention can also bind pre-shed CA 125/O772P. Thus, while not wishing to be bound by any particular mechanism or theory thereof, it is noted that the methods described in this section can be effectuated by binding of the administered antibody, antigen-binding antibody fragments, fusion polypeptides, or analogs of the invention to pre-shed CA 125/O772P in addition to, or instead of, their binding to cell-associated CA 125/O772P.

5.1. Antibodies and Antigen-Binding Antibody Fragments of the Invention

In a first aspect, the present invention provides an isolated antibody, or an antigen-binding antibody fragment, that preferentially binds cell-associated CA 125/O772P polypeptide relative to shed CA 125/O772P polypeptide. Such antibodies and antigen-binding antibody fragments of the invention are useful for a variety of therapeutic, prophylactic, diagnostic, and purification purposes as described herein.

In one embodiment, an antibody or antigen-binding antibody fragment of the invention is one that binds SEQ ID NO:1 or SEQ ID NO:2 and which preferentially binds cell-associated CA 125/O772P. In one particular such embodiment, the antibody or antigen-binding antibody fragment of the invention binds the non-repeat region depicted in SEQ ID NO:1 or SEQ ID NO:2. In another such embodiment, the antibody or antigen-binding antibody fragment of the invention binds a repeat region depicted in SEQ ID NO:1 or SEQ ID NO:2.

In a first embodiment, the antibody or antigen-binding antibody fragment of the invention exhibits, in an ELISA Competition Assay, less than about 25%, less than about 20%, less than about 15%, less than about 10%, or less than about 5% inhibition of binding to the peptide of FIG. 1 in the presence of a 25-fold (weight/weight) excess of shed CA 125/O772P over the peptide of FIG. 1. In a second embodiment, the antibody or antigen-binding antibody fragment of the invention exhibits, in a Flow Cytometry Competition Assay, an $IC_{50}$, as measured by percent-positive cells, of at least about 0.05 mg/ml, at least about 0.1 mg/ml, at least about 0.25 mg/ml, at least about 0.5 mg/ml, at least about 0.75 mg/ml, or at least about 110 mg/ml shed CA 125/O772P. In a third embodiment, the antibody or antigen-binding antibody fragment of the invention binds the peptide of FIG. 1, but does not detectably bind shed CA 125/O772P polypeptide. An antibody, antigen-binding antibody fragment, that satisfies any one of these three embodiments constitutes an antibody or antigen-binding antibody fragment that preferentially binds cell-associated CA 125/O772P polypeptide relative to shed CA 125/O772P polypeptide.

Among the antibodies and antigen-binding antibody fragments of the invention are antibodies or antigen-binding antibody fragments that bind the peptide of FIG. 1 (SEQ ID NO: 1) with a $K_d$ of less than about 100 nM, less than about 10 nM, less than about 1 nM, less than about 100 pM, or less than about 10 pM as measured by the BIAcore Affinity Assay, which is described in Section 6.4, hereinbelow.

Among the preferred embodiments of the antibodies or antigen-binding antibody fragments of the invention are antibodies or antigen-binding antibody fragments that mediate lysis of CA 125/O772P-positive tumor cells in an ADCC assay. Such antibodies or antigen-binding antibody fragments include, for example, those that mediate at least about 10%, at least about 20%, at least about 30%, at least about 40% or at least about 50% lysis of CA 125/O772P-positive tumor cells in an ADCC assay at a 50:1 effector:target ratio at a concentration of 5 µg antibody or antigen-binding fragment per ml; mediate at least about 10%, at least about 20%, at least about 30%, at least about 40% or at least about 50% lysis of CA 125/O772P-positive tumor cells in an ADCC assay at a 25:1 effector:target ratio at a concentration of 5 µg antibody or antigen-binding fragment per ml; mediate at least about 10%, at least about 20%, at least about 30%, at least about 40% or at least about 50% lysis of CA 125/O772P-positive tumor cells in an ADCC assay at a 12.5:1 effector:target ratio at a concentration of 5 µg antibody or antigen-binding fragment per ml; mediate at least about 10%, at least about 20%, at least about 30%, at least about 40% or at least about 50% lysis of CA 125/O772P-positive tumor cells in an ADCC assay at a 12.5:1 effector:target ratio at a concentration of 0.5 µg antibody or antigen-binding fragment per ml; or mediate at least about 10%, at least about 20%, at least about 30%, at least about 40%, or at least about 50% lysis of CA 125/O772P-positive tumor cells in an ADCC assay at a 12.5:1 effector:target ratio at a concentration of 50 ng antibody or antigen-binding fragment per ml.

Preferred embodiments of the invention also include antibodies or antigen-binding antibody fragments that mediate lysis of CA 125/O772P-positive tumor cells in a complement-dependent cytotoxicity (CDC) assay. Such antibodies or antigen-binding antibody fragments include, for example, those that mediate lysis in a range of about 15% lysis at 5 µg/ml to about 95% lysis at 0.1 µg/ml.

Preferred embodiments of the antibodies or antigen-binding antibody fragments of the invention also include antibodies and antigen-binding antibody fragments that inhibit CA 125/O772P-positive tumor growth. For example, such antibodies or antigen-binding antibody fragments are those that, preferably, inhibit CA 125/O772P-positive tumor growth in such animal models as the ones described in Treskes et Eur. J. Cancer. 30A(2):183-187 (1994); Ahmad et al., Oncol. Res. 11(6):273-280 (1999); and Kievit et al., Int. J. Radiat. Oncol. Biol. Phys. 38(2):419-428 (1997), and the OVCAR-3 xenograft tumor animal model described in Section 6.8, below.

In one particular embodiment, an antibody of the invention is a monoclonal antibody produced by hybridoma 4E7 (ATCC® Accession No. PTA-5109), or by hybridoma 7A11 (ATCC® Accession No. PTA-5110), or by hybridoma 7C6 (ATCC® Accession No. PTA-5111), or by hybridoma 7F10 (ATCC® Accession No. PTA-5112), or by hybridoma 7G10 (ATCC® Accession No. PTA-5245), or by hybridoma 7H1 (ATCC® Accession No. PTA-5114), or by hybridoma 8A1 (ATCC® Accession No. PTA-5115), or by hybridoma 8B5 (ATCC® Accession No. PTA-5116), or by hybridoma 8C3 (ATCC® Accession No. PTA-5246), or by hybridoma 8E3 (ATCC® Accession No. PTA-5118), or by hybridoma 8G9 (ATCC® Accession No. PTA-5119), or by hybridoma 15C9 (ATCC® Accession No. PTA-5106), or by hybridoma 16C7 (ATCC® Accession No. PTA-5107), or by hybridoma 16H9 (ATCC® Accession No. PTA-5108), or by hybridoma 117.1 (ATCC® Accession No. PTA-4567), or by hybridoma 325.1 (ATCC® Accession No. PTA-5120), or by hybridoma 368.1 (ATCC® Accession No. PTA-4568), or by hybridoma 446.1 (ATCC® Accession No. PTA-5549) Accession No. PTA-4569), or by hybridoma 501.1 (ATCC® Accession No. PTA-4569), or by hybridoma 621.1 (ATCC® Accession No. PTA-5121), or by hybridoma 633.1 (ATCC® Accession No. PTA-5122), or by hybridoma 654.1 (ATCC® Accession No. PTA-5247), or by hybridoma 725.1 (ATCC® Accession No. PTA-5124), or by hybridoma 776.1 (ATCC® Accession No. PTA-4570).

In another particular embodiment, an antibody or antigen-binding antibody fragment of the invention is an antibody or antigen-binding antibody fragment that competes with the monoclonal antibody produced by hybridoma 4E7 (ATCC® Accession No. PTA-5109), or by hybridoma 7A11 (ATCC® Accession No. PTA-5110), or by hybridoma 7C6 (ATCC® Accession No. PTA-5111), or by hybridoma 7F10 (ATCC® Accession No. PTA-5112), or by hybridoma 7G10 (ATCC® Accession No. PTA-5245), or by hybridoma 7H1 (ATCC® Accession No. PTA-5114), or by hybridoma 8A1 (ATCC® Accession No. PTA-5115), or by hybridoma 8B5 (ATCC® Accession No. PTA-5116), or by hybridoma 8C3 (ATCC® Accession No. PTA-5246), or by hybridoma 8E3 (ATCC® Accession No. PTA-5118), or by hybridoma 8G9 (ATCC® Accession No. PTA-5119), or by hybridoma 15C9 (ATCC® Accession No. PTA-5106), or by hybridoma 16C7 (ATCC® Accession No. PTA-5107), or by hybridoma 16H9 (ATCC®Accession No. PTA-5108), or by hybridoma 117.1 (ATCC®Accession No. PTA-4567), or by hybridoma 325.1 (ATCC® Accession No. PTA-5120), or by hybridoma 368.1 (ATCC® Accession No. PTA-4568), or by hybridoma 446.1 (ATCC® Accession No. PTA-5549), or by hybridoma 501.1 (ATCC® Accession No. PTA-4569), or by hybridoma 621.1 (ATCC® Accession No. PTA-5121), or by hybridoma 633.1 (ATCC® Accession No. PTA-5122), or by hybridoma 654.1 (ATCC® Accession No. PTA-5247), or by hybridoma 725.1 (ATCC®Accession No. PTA-5124), or by hybridoma 776.1 (ATCC® Accession No. PTA-4570) for binding to cell-associated CA 125/O772P. Antibodies or antibody-binding antibody fragments of the invention are considered to compete for binding if they compete for binding in an ELISA Cross-Competition Assay and/or a FACS Cross-Competition Assay. An antibody or antigen-binding antibody fragment is considered to compete for binding in an ELISA Cross-Competition Assay or a FACS Cross-Competition Assay if the $IC_{50}$ for the competitor antibody or antigen-binding fragment is a concentration no more than about 100-fold above the concentration of the antibody or antigen-binding antibody fragment. In a preferred embodiment, the $IC_{50}$ of the competitor antibody or antigen-binding antibody fragment is a concentration no more than about 10-fold above the concentration of the antibody or antigen-binding fragment. In a more preferred embodiment, the $IC_{50}$ of the competitor antibody or antigen-binding antibody fragment is no more than about equimolar with the concentration of the antibody or antigen-binding antibody fragment.

In another particular embodiment, an antibody or antigen-binding fragment of the invention is one that comprises a light chain polypeptide variable region comprising the amino acid sequence depicted in SEQ ID NO:27 (117.1L). In yet another particular embodiment, an antibody or antigen-binding fragment of the invention is one that comprises a heavy chain variable region comprising the amino acid sequence depicted in SEQ ID NO:28 (117.1H). In still another particular embodiment, an antibody or antigen-binding fragment of the invention is one that comprises a light chain polypeptide variable region comprising the amino acid sequence depicted in SEQ ID NO:27 (117.1L) and a heavy chain polypeptide variable region comprising the amino acid sequence depicted in SEQ ID NO:28 (117.1H).

In another particular embodiment, an antibody or antigen-binding fragment of the invention is one that comprises a light chain polypeptide variable region comprising the amino acid sequence depicted in SEQ ID NO:29 (368.1L). In yet another particular embodiment, an antibody or antigen-binding fragment of the invention is one that comprises a heavy chain variable region comprising the amino acid sequence depicted in SEQ ID NO:30 (368.1H). In still another particular embodiment, an antibody or antigen-binding fragment of the invention is one that comprises a light chain polypeptide variable region comprising the amino acid sequence depicted in SEQ ID NO:29 (368.1L) and a heavy chain polypeptide variable region comprising the amino acid sequence depicted in SEQ ID NO:30 (368.1H).

In another particular embodiment, an antibody or antigen-binding fragment of the invention is one that comprises a light chain polypeptide variable region comprising the amino acid sequence depicted in SEQ ID NO:31 (501.1L). In yet another particular embodiment, an antibody or antigen-binding fragment of the invention is one that comprises a heavy chain variable region comprising the amino acid sequence depicted in SEQ ID NO:32 (501.1H). In still another particular embodiment, an antibody or antigen-binding fragment of the invention is one that comprises a light chain polypeptide variable region comprising the amino acid sequence depicted in SEQ ID NO:31 (501.1L) and a heavy chain polypeptide variable region comprising the amino acid sequence depicted in SEQ ID NO:32 (501.1H).

In another particular embodiment, an antibody or antigen-binding fragment of the invention is one that comprises a light chain polypeptide variable region comprising the amino acid sequence depicted in SEQ ID NO:33 (776.1L). In yet another particular embodiment, an antibody or antigen-binding fragment of the invention is one that comprises a heavy chain variable region comprising the amino acid sequence depicted in SEQ ID NO:34 (776.1H). In still another particular embodiment, an antibody or antigen-binding fragment of the invention is one that comprises a light chain polypeptide variable region comprising the amino acid sequence depicted in SEQ ID NO:33 (776.1L) and a heavy chain polypeptide variable region comprising the amino acid sequence depicted in SEQ ID NO:34 (776.1H).

In another particular embodiment, an antibody or antigen-binding fragment of the invention is one that comprises a 725.1 light chain polypeptide variable region ("725.1L") comprising the amino acid sequence depicted in SEQ ID NO:54. In yet another particular embodiment, an antibody or antigen-binding fragment of the invention is one that comprises a 725.1 heavy chain variable region ("725.1H") comprising the amino acid sequence depicted in SEQ ID NO:53. In still another particular embodiment, an antibody or antigen-binding fragment of the invention is one that comprises a light chain polypeptide variable region comprising the amino acid sequence depicted in SEQ ID NO:54 and a heavy chain polypeptide variable region comprising the amino acid sequence depicted in SEQ ID NO:53.

In another particular embodiment, an antibody or antigen-binding fragment of the invention is one that comprises a 16H9 light chain polypeptide variable region ("16H9L") comprising the amino acid sequence depicted in SEQ ID NO:56. In yet another particular embodiment, an antibody or antigen-binding fragment of the invention is one that comprises a 16H9 heavy chain variable region ("16H9") comprising the amino acid sequence depicted in SEQ ID NO:55. In still another particular embodiment, an antibody or antigen-binding fragment of the invention is one that comprises a light chain polypeptide variable region comprising the amino acid sequence depicted in SEQ ID NO:56 and a heavy chain polypeptide variable region comprising the amino acid sequence depicted in SEQ ID NO:55.

In another particular embodiment, the antibody or antigen-binding antibody fragment of the invention is one that comprises a light chain polypeptide variable region comprising the amino acid sequence depicted in SEQ ID NO:27 (117.1L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:29 (368.1L) and a heavy chain variable region comprising the amino acid sequence depicted in SEQ ID NO:28 (117.1H), SEQ ID NO:32 (501.1H), SEQ ID NO:34 (776.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:31 (501.1L) and a heavy chain variable region comprising the amino acid sequence depicted in SEQ ID NO:28 (117.1H), SEQ ID NO:30 (368.1H), SEQ ID NO:34 (776.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:33 (776.1L) and a heavy chain variable region comprising the amino acid sequence depicted in SEQ ID NO:28 (117.1H), SEQ ID NO:30 (368.1H), SEQ ID NO:32 (501.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:54 (725.1L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H).

In another particular embodiment, the antibody or antigen-binding antibody fragment of the invention is one that comprises a light chain polypeptide variable region comprising the amino acid sequence depicted in SEQ ID NO:33 (16H9L) and a heavy chain variable region comprising the amino acid sequence depicted in SEQ ID NO:30 (368.1H), SEQ ID NO:32 (501.1H), SEQ ID NO:34 (776.1H), SEQ ID NO:53 (725.1H), or SEQ ID NO:55 (16H9H).

In one particular embodiment, an antibody or antigen-binding antibody fragment of the invention comprises a variable light chain region comprising any one, two or three VL CDRs depicted in Table 1, Table 2, Table 3, Table 4, Table 5 and Table 6. In another particular embodiment, an antibody or antigen-binding antibody fragment of the invention comprises a variable heavy chain region comprising any one, two or three VH CDRs depicted in Table 1, Table 2, Table 3, Table 4, Table 5 and Table 6. In yet another particular embodiment, an antibody or antigen-binding antibody fragment of the invention comprises a variable light chain region comprising any on; two or three VL CDRs depicted in Table 1, Table 2, Table 3, Table 4, Table 5 and Table 6 and a variable heavy chain region comprising any one, two or three VH CDRs depicted in Table 1, Table 2, Table 3, Table 4, Table 5 and Table 6.

In a preferred embodiment, an antibody or antigen-binding antibody fragment of the invention comprises a variable light chain region comprising any two or three VL CDRs depicted in Table 1; or any two or three VL CDRs depicted in Table 2; or any two or three VL CDRs depicted in Table 3; or any two or three VL CDRs depicted in Table 4; or any two or three VL CDRs depicted in Table 5; or any two or three VL CDRs depicted in Table 6. In another preferred embodiment, an antibody or antigen-binding antibody fragment of the invention comprises a variable heavy chain region comprising any two or three VH CDRs depicted in Table 1; or any two or three VH CDRs depicted in Table 2; or any two or three VH CDRs depicted in Table 3; or any two or three VH CDRs depicted in Table 4; or any two or three VH CDRs depicted in Table 5; or any two or three VH CDRs depicted in Table 6.

In yet another preferred embodiment, an antibody or antigen-binding antibody fragment of the invention comprises a variable light chain region and a variable heavy chain region, said variable light chain region comprising any two or three VL CDRs depicted in Table 1 and said variable heavy chain region comprising any two or three VH CDRs depicted in Table 1; or said variable light chain region comprising any two or three VL CDRs depicted in Table 2 and said variable heavy chain region comprising any two or three VH CDRs depicted in Table 2; or said variable light chain region comprising any two or three VL CDRs depicted in Table 3 and said variable heavy chain region comprising any two or three VH CDRs depicted in Table 3; or said variable light chain region comprising any two or three VL CDRs depicted in Table 4 and said variable heavy chain region comprising any two or three VH CDRs depicted in Table 4; or said variable light chain region comprising any two or three VL CDRs depicted in Table 5 and said variable heavy chain region comprising any two or three VH CDRs depicted in Table 5; or said variable light chain region comprising any two or three VL CDRs depicted in Table 6 and said variable heavy chain region comprising any two or three VH CDRs depicted in Table 6.

For example, an antibody or antigen-binding antibody fragment of the invention can comprise a VL1 domain comprising any of the VL1 CDRs depicted in Table 1, Table 2, Table 3, Table 4, Table 5 and Table 6; an antibody or antigen-binding antibody fragment of the invention can comprise a VL2 domain comprising any of the VL2 CDRs depicted in Table 1, Table 2, Table 3, Table 4, Table 5 and Table 6; or an antibody or antigen-binding antibody fragment of the invention can comprise a VL3 domain comprising any of the VL3 CDRs depicted in Table 1, Table 2, Table 3, Table 4, Table 5 and Table 6; an antibody or antigen-binding antibody fragment of the invention can comprise a VL1 domain and a VL2 domain comprising any of the VL1 CDRs and VL2 CDRs depicted in Table 1, Table 2, Table 3, Table 4, Table 5 and Table 6; an antibody or antigen-binding antibody fragment of the invention can comprise a VL1 domain and a VL3 domain comprising any of the VL1 CDRs and VL3 CDRs depicted in Table 1, Table 2, Table 3, Table 4, Table 5 and Table 6; an antibody or antigen-binding antibody fragment of the invention can comprise a VL2 domain and a VL3 domain comprising any of the VL2 CDRs and VL3 CDRs depicted in Table 1, Table 2, Table 3, Table 4, Table 5 and Table 6; and an antibody or antigen-binding antibody fragment of the invention can comprise a VL1 domain, a VL2 domain and a VL3 domain comprising any of the VL1 CDRs, VL2 CDRs and VL3 CDRs depicted in Table 1, Table 2, Table 3, Table 4, Table 5 and Table 6.

TABLE 1

CDR Sequences Of 117.1

| CDR | Sequence | SEQ ID NO: |
|---|---|---|
| VH1 | GFSLSTPGMGVG | 3 |
| VH2 | HIWWDDFKRDNPALKS | 4 |
| VH3 | VDGNFLSWYFDV | 5 |
| VL1 | RSSQSLVHSNGNTYLH | 6 |
| VL2 | KVSNRFS | 7 |
| VL3 | SQSRYVPET | 8 |

TABLE 2

CDR Sequences Of 368.1

| CDR | Sequence | SEQ ID NO: |
|---|---|---|
| VH1 | GYSFTGFYMH | 9 |
| VH2 | YVSCYTGATTYTQKFKG | 10 |
| VH3 | EGDYYSMDF | 11 |
| VL1 | RSSQSLERTNGNTYLH | 12 |
| VL2 | KVSSRFS | 13 |
| VL3 | SQTTHGPPT | 14 |

TABLE 3

CDR Sequences Of 501.1

| CDR | Sequence | SEQ ID NO: |
|---|---|---|
| VH1 | GYIFTDYGMN | 15 |
| VH2 | CINTYTGETTYSDDFRG | 16 |
| VH3 | GNYRDAIDY | 17 |
| VL1 | KASQDIKSYLS | 18 |
| VL2 | YATTLAD | 19 |
| VL3 | LHHDESPFT | 20 |

TABLE 4

CDR Sequences Of 776.1

| CDR | Sequence | SEQ ID NO: |
|---|---|---|
| VH1 | GYTFTDYNTH | 21 |
| VH2 | YIYPYNGVSDYNQNF | 22 |
| VH3 | RWDFGSGYYFDY | 23 |

TABLE 4-continued

CDR Sequences Of 776.1

| CDR | Sequence | SEQ ID NO: |
|---|---|---|
| VL1 | RASSSVIYMC | 24 |
| VL2 | GTSTLAS | 25 |
| VL3 | QQWSSNPFT | 26 |

TABLE 5

CDR Sequences Of 725.1

| CDR | Sequence | SEQ ID NO: |
|---|---|---|
| VH1 | GYSFTNYGMN | 60 |
| VH2 | WINAYIGEPTYADDFKG | 61 |
| VH3 | GGNSLDF | 62 |
| VL1 | RASSSVSSIH | 63 |
| VL2 | ATSNLAS | 64 |
| VL3 | QQWSIDPAT | 65 |

TABLE 6

CDR Sequences Of 16H9

| CDR | Sequence | SEQ ID NO: |
|---|---|---|
| VH1 | GFNIKDTYMH | 66 |
| VH2 | RIDPANGNTKYDPKFQG | 67 |
| VH3 | SDIYYGNPGGFAY | 68 |
| VL1 | TASSSVSSSYLH | 69 |
| VL2 | STSNLAS | 70 |
| VL3 | HQYHRSPFT | 71 |

The antibodies and antigen-binding antibody fragments of the invention are not, and generally do not compete with, OC125-like antibodies, M11-like antibodies or the OV 197 antibody, as defined in Nustad et al., Tumor Biol. 17:196:219 (1996). In one embodiment, the antibodies and antigen-binding fragments of the invention are not, and generally do not compete with, the OC 125-derived or VK-8-derived single chain antibodies described in WO 03/076465.

The antibodies of the invention can include, but are not limited to, polyclonal antibodies, monoclonal antibodies, chimeric antibodies, humanized antibodies, human antibodies, bi-specific antibodies, tri-specific antibodies, multi-specific antibodies, single-chain antibodies, disulfide-linked Fvs, single-chain Fvs, or anti-idiotypic antibodies. In a preferred embodiment, an antibody of the invention is a monoclonal antibody that preferentially binds cell-associated CA 125/O772P polypeptide relative to shed CA 125/O772P polypeptide. Multispecific antibodies may be specific for different epitopes of cell-associated CA 125/O772P or may be specific for both a cell-associated CA 125/O772P epitope as well as for a heterologous epitope, such as a heterologous polypeptide or solid support material. See, e.g., Tutt et al., J. Immunol. 147(1):60-69 (1991); Kostelny et al., J. Immunol. 148(5): 1547-1553 (1992); and U.S. Pat. Nos. 4,474,893, 4,714,681, 4,925,648, 5,573,920, 5,601,819, 5,798,229, 5,855,866, 5,869,620, 5,897,861, 5,959,084, 6,106,833, 6,248,332, 6,258,358, 6,303,755, and 6,420,140.

The antigen-binding antibody fragments of the invention can include, but are not limited to, Fab fragments, F(ab')$_2$ fragments, variable light chain polypeptide (VL)-containing fragments, variable heavy chain polypeptide (VH)-containing fragments, or complementarity determining region (CDR)-containing fragments.

Further, the antibodies and antigen-binding antibody fragments of the invention can be of any immunoglobulin class. For example, the antibodies of the invention can be IgG, IgM, IgE, IgD, IgA or IgY class antibodies. The antibodies of the invention can also be of any isotype. For example, an antibody of the invention can be of an IgG$_1$, IgG$_2$, IgG$_3$, IgG$_4$, IgA$_1$ or IgA$_2$ heavy chain isotype. Preferably an antibody of the invention is of an IgG$_1$ isotype.

Still further, the antibodies or antigen-binding antibody fragments of the invention, can comprise one or more CDRs, e.g., CDR sequences as described herein, inserted within naturally occurring or consensus framework regions, preferably human framework regions. Further, the antibodies or antigen-binding antibody fragments of the invention can comprise a variable light chain, for example, a κ or λ light chain variable region, and/or a variable heavy chain as described herein, inserted within naturally occurring or consensus framework regions, preferably human framework regions. Such framework regions are well known to those of skill in the art, e.g., can comprise a Cγ1 constant region or a Cγ4 constant region.

The antibodies or antigen-binding antibody fragments that preferentially bind to cell-associated CA 125/O772P may be from any animal origin including birds, e.g., chickens, and mammals, including non-primates (e.g., a cow, pig, horse, donkey, goat, camel, cat, dog, guinea pig, rat, mouse, sheep) and primates (e.g., a monkey, such as a cynomolgous monkey, gorilla, chimpanzee, and a human). Preferably, the antibodies and antigen-binding antibody fragments that preferentially bind to cell-associated CA 125/O772P are chimeric, human, or humanized antibodies, including monoclonal antibodies, or antigen-binding antibody fragments. As used herein, "human" antibodies or antigen-binding antibody fragments include antibodies or antigen-binding antibody fragments having the amino acid sequence of a human immunoglobulin, and include, for example, antibodies or antigen-binding antibody fragments isolated from human immunoglobulin libraries or from mice that express antibodies from human genes.

In another aspect, the present invention provides hybridoma cells that produce a monoclonal antibody of the invention. In one embodiment, a hybridoma of the present invention is hybridoma 4E7 (ATCC® Accession No. PTA-5109), hybridoma 7A11 (ATCC® Accession No. PTA-5110), hybridoma 7C6 (ATCC® Accession No. PTA-5111), hybridoma 7F10 (ATCC® Accession No. PTA-5112), hybridoma 7G10 (ATCC® Accession No. PTA-5245), hybridoma 7H1 (ATCC® Accession No. PTA-5114), hybridoma 8A1 (ATCC® Accession No. PTA-5115), hybridoma 8B5 (ATCC® Accession No. PTA-5116), hybridoma 8C3 (ATCC® Accession No. PTA-5246), hybridoma 8E3 (ATCC® Accession No. PTA-5118), hybridoma 8G9 (ATCC® Accession No. PTA-5119), hybridoma 1509 (ATCC® Accession No. PTA-5106), hybridoma 16C7 (ATCC® Accession No. PTA-5107), hybridoma 16H9

(ATCC® Accession No. PTA-5108), hybridoma 117.1 (ATCC® Accession No. PTA-4567), hybridoma 325.1 (ATCC® Accession No. PTA-5120), hybridoma 368.1 (ATCC® Accession No. PTA-4568), hybridoma 446.1 (ATCC® Accession No. PTA-5549), hybridoma 501.1 (ATCC® Accession No. PTA-4569), hybridoma 621.1 (ATCC® Accession No. PTA-5121), hybridoma 633.1 (ATCC® Accession No. PTA-5122), hybridoma 654.1 (ATCC® Accession No. PTA-5247), hybridoma 725.1 (ATCC® Accession No. PTA-5124), or hybridoma 776.1 (ATCC® Accession No. PTA-4570).

In another embodiment, a hybridoma of the present invention is a hybridoma that produces monoclonal antibodies that compete with the monoclonal antibody produced by hybridoma 4E7 (ATCC® Accession No. PTA-5109), hybridoma 7A11 (ATCC® Accession No. PTA-5110), hybridoma 7C6 (ATCC® Accession No. PTA-5111), hybridoma 7F10 (ATCC® Accession No. PTA-5112), hybridoma 7G10 (ATCC® Accession No. PTA-5245), hybridoma 7H1 (ATCC® Accession No. PTA-5114), hybridoma 8A1 (ATCC® Accession No. PTA-5115), hybridoma 8B5 (ATCC® Accession No. PTA-5116), hybridoma 8C3 (ATCC® Accession No. PTA-5246), hybridoma 8E3 (ATCC® Accession No. PTA-5118), hybridoma 8G9 (ATCC® Accession No. PTA-5119), hybridoma 15C9 (ATCC® Accession No. PTA-5106), hybridoma 16C7 (ATCC® Accession No. PTA-5107), hybridoma 16119 (ATCC® Accession No. PTA-5108), hybridoma 117.1 (ATCC® Accession No. PTA-4567), hybridoma 325.1 (ATCC® Accession No. PTA-5120), hybridoma 368.1 (ATCC® Accession No. PTA-4568), hybridoma 446.1 (ATCC® Accession No. PTA-5549), hybridoma 501.1 (ATCC® Accession No. PTA-4569), hybridoma 621.1 (ATCC® Accession No. PTA-5121), hybridoma 633.1 (ATCC® Accession No. PTA-5122), hybridoma 654.1 (ATCC® Accession No. PTA-5247), hybridoma 725.1 (ATCC® Accession No. PTA-5124), or hybridoma 776.1 (ATCC® Accession No. PTA-4570) for binding to cell-associated CA 125/O772P.

5.2 Fusion Polypeptides of the Invention

In another aspect, the present invention provides a fusion polypeptide comprising an antibody or an antigen-binding antibody fragment of the invention, that is, one that preferentially binds cell-associated CA 125/O772P polypeptide relative to shed CA 125/O772P polypeptide, operably linked to a heterologous agent. Fusion polypeptides of the invention also preferentially bind cell-associated CA 125/O772P. In one embodiment of a fusion polypeptide of the invention, the antibody, or antigen-binding antibody fragment, and the heterologous agent are operably linked via a covalent linkage, such as a peptide bond or disulfide linkage. In another embodiment of a fusion polypeptide of the invention, the antibody, or antigen-binding antibody fragment, and the heterologous agent are operably linked via non-covalent linkage. The heterologous agent can be linked to the amino terminus, carboxyl terminus, or at any point along the contiguous sequence of the antibodies or antigen-binding antibody fragments. The operable linkage need not be directly between the antibody or antigen-binding antibody fragment and the heterologous agent, but can, for example, occur through a linker or spacer agent or sequence.

In one embodiment of a fusion polypeptide of the invention, the heterologous agent comprises an amino acid sequence or a radioisotope. The heterologous agent of the fusion polypeptide of the invention can comprise a cytotoxic agent or a detectable agent.

Fusion polypeptides of the invention can, for example, be used in generating antibodies or antigen-binding antibody fragments of the invention. Alternatively, fusion polypeptides can be utilized as part of the methods of prevention or treatment described herein. Still further fusion polypeptides of the invention can be utilized as part of in vivo and in vitro immunoassays and purification methods using methods known in the art. See e.g., PCT publication Number WO 93/21232; U.S. Pat. Nos. 5,314,995, 5,474,981, 5,514,558, 6,362,317, and 6,403,769; Nakamura et al., Immunol. Lett. 39(1):91-99 (1993); Gillies et al., Proc. Natl. Acad. Sci. USA. 89(4):1428-1432 (1992); and Fell et al., J. Immunol. 146(7):2446-2452 (1991), which are incorporated herein by reference in their entireties.

In instances where the heterologous agent is a polypeptide, the heterologous polypeptide is generally at least about 5, at least about 10, at least about 20, at least about 30, at least about 40, at least about 50, at least about 60, at least about 70, at least about 80, at least about 90, or at least about 100 amino acids.

In one embodiment, the fusion polypeptides of the invention comprise antibodies or antigen-binding antibody fragments that preferentially bind cell-associated CA 125/O772P operably linked to a heterologous agent that provides a potential therapeutic benefit. For example, an antibody or an antigen-binding fragment thereof that preferentially binds cell-associated CA 125/O772P may be operably linked to a therapeutic moiety such as a cytotoxin, e.g., a cytostatic or cytocidal agent, an agent, or a radioactive ion, e.g., alpha-emitters. See, e.g., U.S. Pat. Nos. 5,624,827, 5,643,573, 5,789,554, 5,824,782, 5,994,151, 6,042,829, 6,074,644, 6,099,842, 6,132,722, 6,187,287, 6,197,299, and 6,207,805. A cytotoxin or cytotoxic agent includes any agent that is detrimental to cell growth or cell viability. Examples of a cytotoxin or cytotoxic agent include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Other agents which have a potential therapeutic benefit include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), maytansinoids and anti-mitotic agents (e.g., vincristine and vinblastine) and radioactive material, including, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium (177Lu), manganese (54Mn), molybdenum (99Mo), palladium (103Pd), phosphorous ($^{32}$P), praseodymium ($^{142}$Pr), promethium ($^{149}$Pm), rhenium ($^{186}$Re, $^{188}$Re), rhodium ($^{105}$Rh), ruthenium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), and zinc ($^{65}$Zn).

Further, the antibody or antigen-binding antibody fragment can be conjugated to a therapeutic agent or drug moiety. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin PE-40), or diphtheria toxin, ricin, gelonin, and pokeweed antiviral protein, a protein such as tumor necrocis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas Ligand (Takahashi et al., *J. Immunol.*, 6:1567-1574, 1994), and VEGI (PCT Publication No. WO 99/23105), a thrombotic agent or an anti-angiogenic agent (e.g., antistatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor (G-CSF")), macrophage colony stimulating factor ("M-CSF"), or a growth factor (e.g., growth hormone ("GH")); proteases, or ribonucleases.

Fusion polypeptides of the invention can, alternatively, be used diagnostically to, e.g., monitor the development or progression of cancer or tumor as part of a clinical testing procedure, for example to determine the efficacy of a given treatment regimen, such as where the antibody is coupled to a detectable agent. Examples of detectable agents include various enzymes, prosthetic groups, fluorescent materials, luminescent materials, bioluminescent materials, radioactive materials, positron emitting metals, and nonradioactive paramagnetic metal ions. The detectable agent may be coupled or conjugated either directly to the antibody or indirectly, through an intermediate (such as, for example, a linker known in the art) using techniques known in the art. See, e.g., U.S. Pat. Nos. 4,741,900, 5,693,764, 5,776,095, 6,008,002, 6,013,531, 6,110,750, 6,124,105, 6,197,523, and 6,225,050.

Non-limiting examples of suitable enzymes that can be conjugated to an antibody or antigen-binding antibody fragment of the invention include β-lactamases, β-galactosidases, phosphatases, peroxidases, reductases, esterases, hydrolases, isomerases and proteases, such as horseradish peroxidase, alkaline phosphatase, beta-galactosidase, or acetylcholinesterase; non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, green fluorescent protein, red fluorescent protein, dansyl chloride or phycoerythrin; a non-limiting example of a luminescent material includes luminol. Non-limiting examples of bioluminescent materials include luciferase, luciferin, and aequorin; and examples of suitable radioactive material include $^{125}$I, $^{131}$I, $^{111}$In, $^{99m}$Tc, or $^{90}$Y.

The present invention also encompasses antibodies or antigen-binding. fragments thereof that preferentially bind to cell-associated CA 125/O772P fused to marker sequences, such as a peptide to facilitate purification. For example, a marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA. 86(3):821-824 (1989), for instance, histidine, e.g., hexa-histidine, provides for convenient purification of the fusion protein. Other peptide tags useful for purification include, but are not limited to, the hemagglutinin "HA" tag, which corresponds to an epitope derived from the influenza hemagglutinin protein (Wilson et al., Cell. 37(3):767-778 (1984)) and the "flag" tag (Brizzard et al., Biotechniques. 16(4):730-735 (1994)). Preferably, such tags or marker sequences are cleaved from the fusion polypeptide prior to use, e.g., use as part of a therapeutic method.

An antibody or an antigen-binding fragment thereof that preferentially binds cell-associated CA 125/O772P can also, for example, be operably linked to a second antibody to form an antibody heteroconjugate as described in U.S. Pat. No. 4,676,980, which is incorporated herein by reference in its entirety.

Techniques for operably linking moieties to antibodies are well known, see, e.g., Amon et al: "Monoclonal Antibodies For Immunotargeting Of Drugs In Cancer Therapy", in *Monoclonal Antibodies And Cancer Therapy*, Reisfeld et al., eds., Alan R. Liss, Inc. (1985) at pages 243-256; Hellstrom et al., "Antibodies For Drug Delivery", in *Controlled Drug Delivery (2nd Ed.)*, Robinson et al., eds., Marcel Dekker, Inc. (1987) at pages 623-653; Thorpe, "Antibody Carriers Of Cytotoxic Agents In Cancer Therapy: A Review", in *Monoclonal Antibodies '84: Biological And Clinical Applications*, Pinchera et al., eds., Editrice Kurtis (1985) at pages 475-506; Order et al., "Analysis, Results, And Future Prospective Of The Therapeutic Use Of Radiolabeled Antibody In Cancer Therapy", in *Monoclonal Antibodies For Cancer Detection And Therapy*, Baldwin at al., eds., Academic Press (1985) at pages 303-316; Thorpe et al., Immunol. Rev. 62:119-158 (1982); and U.S. Pat. Nos. 5,639,879, 5,744,119, 5,773,001, and 6,441,163.

Methods for fusing or conjugating polypeptides to the constant regions of antibodies are known in the art. See, e.g., U.S. Pat. Nos. 5,336,603, 5,622,929, 5,359,046, 5,349,053, 5,447,851, 5,648,218, 5,723,125, 5,783,181, 5,908,626, 5,844,095, 5,112,946, 6,030,613, 6,086,875, 6,194,177, 6,238,667, 6,262,026, and 6,277,375; EP 307,434; EP 367,166; EP 394,827; PCT publication WO 91/06570; Ashkenazi et al., Proc. Natl. Acad. Sci. USA. 88(23):10535-10539 (1991); Traunecker et al., Nature. 331(6151):84-86 (1988); Zheng et al., J. Immunol. 154(10):5590-5600 (1995) and Vie et al., Proc. Natl. Acad. Sci. USA. 89(23):11337-11341 (1992), which are incorporated herein by reference in their entireties.

5.3. Analogs of the Invention

Also included among the antibodies, antigen-binding antibody fragments, and fusion polypeptides of the invention are antibody, antigen-binding antibody fragment, and fusion polypeptide analogs that preferentially bind cell-associated CA 125/O772P relative to shed CA 125/O772P. For example, among the analogs of the invention are analogs of the monoclonal antibody produced by hybridoma 4E7 (ATCC® Accession No. PTA-5109), hybridoma 7A11 (ATCC® Accession No. PTA-5110), hybridoma 7C6 (ATCC® Accession No. PTA-5111), hybridoma 7F10 (ATCC® Accession No. PTA-5112), hybridoma 7G10 (ATCC® Accession No. PTA-5245), hybridoma 7H1 (ATCC® Accession No. PTA-5114), hybridoma 8A1 (ATCC® Accession No. PTA-5115), hybridoma 8B5 (ATCC® Accession No. PTA-5116), hybridoma 8C3 (ATCC® Accession No. PTA-5246), hybridoma 8E3 (ATCC® Accession No. PTA-5118), hybridoma 8G9 (ATCC® Accession No. PTA-5119), hybridoma 15C9 (ATCC® Accession No. PTA-5106), hybridoma 16C7 (ATCC® Accession No. PTA-5107), hybridoma 16119 (ATCC® Accession No. PTA-5108), hybridoma 117.1 (ATCC® Accession No. PTA-4567), hybridoma 325.1

(ATCC®Accession No. PTA-5120), hybridoma 368.1 (ATCC® Accession No. PTA-4568), hybridoma 446.1 (ATCC® Accession No. PTA-5549), hybridoma 501.1 (ATCC® Accession No. PTA-4569), hybridoma 621.1 (ATCC® Accession No. PTA-5121), hybridoma 633.1 (ATCC® Accession No. PTA-5122), hybridoma 654.1 (ATCC® Accession No. PTA-5247), hybridoma 725.1 (ATCC® Accession No. PTA-5124), hybridoma 776.1 (ATCC® Accession No. PTA-4570), or analogs of antigen-binding antibody fragments thereof.

Such an analog possesses at least one of the following structural features: (a) an amino acid sequence that is preferably at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or at least about 99% identical to the amino acid sequence of the pre-modified antibody, antigen-binding antibody fragment, or fusion polypeptide; (b) is encoded by a nucleotide sequence that hybridizes under stringent conditions to the complement of a nucleotide sequence encoding at least 5 contiguous amino acid residues, at least about 10 contiguous amino acid residues, at least about 15 contiguous amino acid residues, at least about 20 contiguous amino acid residues, at least about 25 contiguous amino acid residues, at least about 40 contiguous amino acid residues, at least about 50 contiguous amino acid residues, at least about 60 contiguous amino residues, at least about 70 contiguous amino acid residues, at least about 80 contiguous amino acid residues, at least about 90 contiguous amino acid residues, at least about 100 contiguous amino acid residues, at least about 110 contiguous amino acid residues, or at least about 120 contiguous amino acid residues of the amino acid sequence of the pre-modified antibody, antigen-binding antibody fragment, or fusion polypeptide; or (c) is encoded by a nucleotide sequence that is at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or at least about 99% identical to the nucleotide sequence encoding the pre-modified antibody, antigen-binding antibody fragment, or fusion polypeptide.

In a specific embodiment, an analog of an antibody, antigen-binding antibody fragment, or fusion polypeptide that preferentially binds cell-associated CA 125/O772P comprises an amino acid sequence that is preferably at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% identical to the amino acid sequence of the monoclonal antibody produced by hybridoma 4E7 (ATCC® Accession No. PTA-5109), hybridoma 7A11 (ATCC® Accession No. PTA-5110), hybridoma 7C6 (ATCC® Accession No. PTA-5111), hybridoma 7F10 (ATCC® Accession No. PTA-5112), hybridoma 7G10 (ATCC® Accession No. PTA-5245), hybridoma 7I11 (ATCC® Accession No. PTA-5114), hybridoma 8A1 (ATCC® Accession No. PTA-5115), hybridoma 8135 (ATCC® Accession No. PTA-5116), hybridoma 8C3 (ATCC® Accession No. PTA-5246), hybridoma 8E3 (ATCC® Accession No. PTA-5118), hybridoma 8G9 (ATCC® Accession No. PTA-5119), hybridoma 15C9 (ATCC® Accession No. PTA-5106), hybridoma 16C7 (ATCC® Accession No. PTA-5107), hybridoma 16119 (ATCC® Accession No. PTA-5108), hybridoma 117.1 (ATCC® Accession No. PTA-4567), hybridoma 325.1 (ATCC® Accession No. PTA-5120), hybridoma 368.1 (ATCC® Accession No. PTA-4568), hybridoma 446.1 (ATCC® Accession No. PTA-5549), hybridoma 501.1 (ATCC® Accession No. PTA-4569), hybridoma 621.1 (ATCC® Accession No. PTA-5121), hybridoma 633.1 (ATCC® Accession No. PTA-5122), hybridoma 654.1 (ATCC® Accession No. PTA-5247), hybridoma 725.1 (ATCC® Accession No. PTA-5124), or hybridoma 776.1 (ATCC® Accession No. PTA-4570).

Preferably, the analogs include less than about 25, less than about 20, less than about 15, less than about 10, less than about 5, less than about 4, less than about 3, or less than about 2 amino acid substitutions, additions or deletions, or combinations thereof, relative to the original molecule. In a preferred embodiment, the analogs have conservative amino acid substitutions made at one or more amino acid residues predicted to be non-essential (i.e., amino acid residues which are not critical for the antibody to specifically and preferentially bind to cell-associated CA 125/O772P). A "conservative amino acid substitution" is one in which the amino acid residue is replaced with an amino acid residue, mimic or analog having a side chain with a similar charge or polarity. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Moreover, the analogs of the invention can include additions and/or be, at least in part, generated from deletions relative to the original molecule. Additions and/or deletions can be of any identity or combination so long as the structural criteria for analogs of the invention set forth above are satisfied.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin et al., Proc. Natl. Acad. Sci. USA. 87(6):2264-2268 (1990), as modified in Karlin et al., Proc. Natl. Acad. Sci. USA. 90(12):5873-5877 (1993). Such an algorithm is incorporated into the BLASTN and BLASTX programs of Altschul et al., J. Mol. Biol. 215(3):403-410 (1990). BLAST nucleotide searches can be performed with the BLASTN nucleotide program parameters set, e.g., for score=100, wordlength=12 to obtain nucleotide sequences homologous to nucleic acid molecules of the present invention. BLAST protein searches can be performed with the BLASTX program parameters set, e.g., to score=50, wordlength=3 to obtain amino acid sequences homologous to a protein molecule of the present invention. To obtain gapped alignments for comparison purposes, Gapped BLAST can be utilized as described in Altschul et al., Nucleic Acids Res. 25(17):3389-3402 (1997). Alternatively, PSI-BLAST can be used to perform an iterated search which detects distant relationships between molecules (Id.). When utilizing BLAST, Gapped BLAST, and PSI-Blast programs, the default parameters of the respective programs (e.g., of BLASTX and BLASTN) can be used. Another preferred, non-limiting example of a mathematical algorithm utilized for the comparison of sequences is the algorithm of Myers and Miller (Myers et al., Comput. Appl. Biosci. 4(1):11-17 (1988)). Such an algorithm is incorporated in the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

An analog can also refer to an antibody, antigen-binding antibody fragment or fusion polypeptide of the invention that has been modified by the attachment, e.g., covalent attachment, of any type of molecule to a corresponding pre-modified antibody or antigen-binding antibody fragment, and which still preferentially binds cell-associated CA 125/O772P. For example, and not by way of limitation, an antibody, antigen-binding antibody fragment or fusion polypeptide can be modified by glycosylation, acetylation, alkylation, esterification, lipidation, formylation, pegylation, phosphorylation, amidation, derivatization by protecting/blocking groups, proteolytic cleavage, linkage to a cellular ligand or other protein, etc. Further, an analog can contain one or more non-classical amino acids. Non-classical amino acids include but are not limited to the D-isomers of the common amino acids, α-amino isobutyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In one embodiment, an analog of the invention exhibits increased affinity for cell-associated CA 125/O772P relative to that of a corresponding pre-modified antibody, antigen-binding antibody fragment or fusion polypeptide. In another specific embodiment, an antibody, antigen-binding antibody fragment or fusion polypeptide that preferentially binds cell-associated CA 125/O772P has an increased serum half-life relative to a corresponding pre-modified antibody, antigen-binding antibody fragment or fusion polypeptide. For example, an analog can exhibit a half-life in an animal, preferably a mammal and most preferably a human, of greater than about 1 day, greater than about 2 days, greater than about 3 days, greater than about 7 days, greater than about 10 days, preferably greater than about 15 days, greater than about 25 days, greater than about 30 days, greater than about 35 days, greater than about 40 days, or greater than about 45 days.

To prolong the serum circulation of antibodies, antigen-binding antibody fragments or fusion polypeptides in vivo, for example, inert polymer molecules such as high molecular weight polyethylene glycol (PEG) can be attached to the antibodies, antigen-binding antibody fragments or fusion polypeptides with or without a multifunctional linker either through site-specific conjugation of the PEG to the amino- or carboxyl-terminus of the antibodies, antigen-binding antibody fragments or fusion polypeptides or via epsilon-amino groups present on lysine residues. Linear or branched polymer derivatization that results in minimal loss of biological activity is preferred. The degree of conjugation can be closely monitored by SDS-PAGE and mass spectrometry to ensure proper conjugation of PEG molecules to the antibodies. Unreacted PEG can be separated from antibody-, antigen-binding antibody fragment- or fusion polypeptide-PEG conjugates by size-exclusion or by ion-exchange chromatography. PEG-derivatized antibodies, antigen-binding antibody fragments and fusion polypeptides can be tested for binding activity as well as for in vivo efficacy using methods known to those of skill in the art, for example, by immunoassays described herein.

Antibodies or antigen-binding antibody fragments having an increased half-life in vivo can also be generated by introducing one or more amino acid modifications (i.e., substitutions, insertions or deletions) into an IgG constant domain, or FcRn binding fragment thereof (preferably a Fc or hinge-Fc domain fragment). See, e.g., PCT Publication No. WO 98/23289 and U.S. Pat. No. 6,277,375, each of which is incorporated herein by reference in its entirety.

5.4. Nucleic Acid Molecules of the Invention

In yet another aspect, the present invention provides an isolated nucleic acid molecule that comprises a nucleotide sequence that encodes an antibody or antigen-binding antibody fragment, fusion polypeptide, or analog thereof, of the invention.

In one embodiment, a nucleic acid molecule of the invention encodes an antibody, antigen-binding antibody fragment, fusion polypeptide, or analog thereof, that comprises at least one, preferably two or three, of the light chain CDRs listed in Table 1, Table 2, Table 3, Table 4, Table 5 or Table 6. For example, a nucleic acid molecule of the invention can comprise a nucleotide sequence of SEQ ID NO:35, SEQ ID NO:37, SEQ ID NO:39, SEQ ID NO:41, SEQ ID NO:52, or SEQ ID NO:59 that encodes at least one, preferentially two or three, of said light chain CDRs.

In another embodiment, a nucleic acid molecule of the invention encodes an antibody, antigen-binding antibody fragment, fusion polypeptide, or analog thereof, that comprises at least one, preferably two or three, of the heavy chain CDRs listed in Table 1, Table 2, Table 3, Table 4, Table 5 and Table 6. For example, a nucleic acid molecule of the invention can comprise a nucleotide sequence of SEQ ID NO:36, SEQ ID NO:38, SEQ ID NO:40, SEQ ID NO:42, SEQ ID NO:57 or SEQ ID NO:58 that encodes at least one, preferentially two or three of said heavy chain CDRs.

In another embodiment, a nucleic acid molecule of the invention comprises a nucleotide sequence that encodes an antibody, antigen-binding antibody fragment, fusion polypeptide or analog thereof that comprises a variable light chain polypeptide sequence shown in FIG. 5C, FIG. 6C, FIG. 7C, FIG. 8C, FIG. 9C or FIG. 10C. For example, a nucleic acid molecule of the invention can comprise the nucleotide sequence of SEQ ID NO:35 (117.1), SEQ ID NO:37 (368.1), SEQ ED NO:39 (501.1), SEQ ID NO:41 (776.1), SEQ ID NO:52 (725.1) or SEQ ID NO:59 (16H9).

In yet another embodiment, a nucleic acid molecule of the invention comprises a nucleotide sequence that encodes an antibody, antigen-binding antibody fragment, fusion polypeptide or analog thereof that comprises a variable heavy chain polypeptide sequence shown in FIG. 5D, FIG. 6D, FIG. 7D, FIG. 8D, FIG. 9D or FIG. 10D. For example, a nucleic acid molecule of the invention can comprise the nucleotide sequence of SEQ ID NO:36 (117.1), SEQ ID NO:38 (368.1), SEQ ID NO:40 (501.1), SEQ ID NO:42 (776.1), SEQ ID NO:57 (725.1) or SEQ ID NO:58 (16H9).

Among the nucleic acid molecules of the invention are nucleic acid molecules that are degenerate variants, or that hybridize under stringent conditions to the complement of a nucleic acid molecule having a nucleotide sequence encoding an antibody or antigen-binding antibody fragment of the invention. For example, in one embodiment, a nucleic acid molecule of the invention is one that hybridizes under stringent conditions to the complement of SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:52, SEQ ID NO:57, SEQ ID NO:58, or SEQ ID NO:59. Preferably, such hybridizing nucleic acid molecules of the invention encode an antibody or antigen-binding antibody fragment of the invention.

5.5. Pharmaceutical Compositions of the Invention

In another aspect, the present invention provides a pharmaceutical composition comprising an antibody or an antigen-binding antibody fragment, fusion polypeptide, analog or nucleic acid molecule of the invention, and a pharmaceutically acceptable carrier.

Preferably, a pharmaceutical composition of the invention comprises an antibody, antigen-binding antibody fragment, fusion polypeptide, or analog of the invention that exhibits a $K_d$ of less than about 100 nM, less than about 10 nM, less than about 1 nM, less than about 100 pM, or less than about 10 pM for the peptide of FIG. 1 (SEQ ID NO: 1) as measured by the BIAcore Affinity Assay, as described in Section 6.4. Alternatively, a pharmaceutical composition of the invention can comprise an antibody, antigen-binding antibody fragment, fusion polypeptide, or analog or nucleic acid molecule of the invention that mediates lysis of a CA 125/O772P-positive tumor cell. Most preferably, a pharmaceutical composition of the invention comprises an antibody, antigen-binding antibody fragment, fusion polypeptide, analog or a nucleic acid molecule of the invention that encodes a polypeptide that inhibits CA 125/O772P-positive tumor growth, either by itself or when conjugated to a cytotoxic agent.

In one embodiment, the antibody or antigen-binding antibody fragment of the invention, or a fusion polypeptide or analog thereof, is conjugated to a cytotoxic agent useful in treating the cell-proliferative disease such as those cytotoxic agents recited in Section 5.2, hereinabove. In a particular embodiment, the cytotoxic agent is a radioisotope. In a further particular embodiment, the radioisotope is selected from the group consisting of $^{125}I$, $^{131}I$, $^{111}In$, $^{99m}Tc$ and $^{90}Y$.

The term "carrier" refers to a diluent, adjuvant (e.g., Freund's adjuvant (complete or incomplete)), excipient, stabilizing agent, preservatives, binder, or vehicle for administration of an antibody, antigen-binding antibody fragment, fusion polypeptide, or analog of the invention. Pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington: The Science & Practice of Pharmacy*, 20$^{th}$ edition, Gennaro, ed., Lippincott (2000).

In a preferred embodiment, the pharmaceutical compositions are sterile and in suitable form for administration to a subject, preferably an animal subject, more preferably a mammalian subject, and most preferably a human subject.

In a specific embodiment, it may be desirable to administer the pharmaceutical compositions of the invention locally to the area in need of treatment. This may be achieved by, for example, and not by way of limitation, local infusion; by injection, or by means of an implant, said implant being of a porous, non-porous, or gelatinous material, including membranes, such as sialastic membranes, or fibers. Preferably, when administering pharmaceutical compositions, care must be taken to use materials to which the antibodies, antigen-binding antibody fragments, fusion polypeptides or analogs in the pharmaceutical composition or compositions do not adsorb.

In another embodiment, the pharmaceutical composition can be present and delivered in a vesicle, in particular a liposome (see, e.g., Langer, Science 249(4976):1527-1533 (1990); Treat et al., in *Liposomes in the Therapy of Infectious Disease and Cancer*, Lopez-Berestein et al., eds., Liss (1989) at pages 353-365; Lopez-Berestein et at, ibid., at pages 317-327; Lopez-Berestein et al., ibid., generally; and U.S. Pat. Nos. RE35,338, 5,662,931, 5,759,519, 5,879,713, 6,027,726, 6,099,857, 6,132,764, 6,245,427, 6,284,375, 6,350,466, and 6,417,326).

In yet another embodiment, the composition can be present and delivered in a controlled release or sustained release system. In one embodiment, a pump may be used to achieve controlled or sustained release (see, e.g., Langer, Science 249(4976):1527-1533 (1990); Sefton, Crit. Rev. Biomed. Eng. 14(3):201-40 (1987); Buchwald et al., Surgery. 88(4):507-516 (1980); Saudek et al., N. Engl. J. Med. 321(9):574-579 (1989); and U.S. Pat. Nos. 5,720,720 and 6,352,683). In another embodiment, polymeric materials can be used to achieve controlled or sustained release of the antibodies, antigen-binding antibody fragments, fusion polypeptides or analogs of the invention or fragments thereof (see, e.g., Medical Applications of Controlled Release, Langer and Wise (eds.), CRC Pres., Boca Raton, Fla. (1974) *Medical Applications of Controlled Release*, Langer et al., eds., CRC Press (1974); *Controlled Drug Bioavailability, Drug Product Design and Performance*, Smolen et al., eds., Wiley (1984); Ranger et al., J. Macromol. Sci. Rev. Macromol. Chem. 23:61 (1983); Levy et al., Science. 228(4696):190-192 (1985); During et al.,Ann. Neurol. 25(4):351-356 (1989); Howard et al., J. Neurosurg. 71(1):105-112 (1989); U.S. Pat. Nos. 5,128,326, 5,679,377, 5,863,985, 5,912,015, 5,916,597, 5,989,463, 5,994,492, 6,011,011, 6,020,004, 6,066,325, 6,180,608, 6,190,702, 6,214,966, 6,221,958, 6,221,977, 6,267,981, 6,362,276, 6,365,173, 6,375,985, 6,394,997, and 6,399,103; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters.

A pharmaceutical composition of the invention is formulated to be compatible with its intended route of administration. Examples of routes of administration include, but are not limited to, e.g., parenteral (e.g., intravenous, intradermal, intramuscular, subcutaneous), oral, intranasal, inhalation, transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic to ease pain at the site of the injection.

If the pharmaceutical compositions of the invention are to be administered topically, the compositions can be formulated in the form of, e.g., an ointment, cream, transdermal patch, lotion, gel, shampoo, spray, aerosol, solution, emulsion, or other form well-known to one of skill in the art. See, e.g., *Remington: The Science & Practice of Pharmacy, 20th* edition, Gennaro, ed., Lippincott (2000). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which can be, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well-known in the art.

If the pharmaceutical compositions of the invention are to be administered intranasally, the compositions can be formulated in an aerosol form, spray, mist or in the form of drops. In particular, agents for use according to the present invention can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

If the pharmaceutical compositions of the invention are to be administered orally, the pharmaceutical compositions can be formulated orally in the form of, e.g., tablets, capsules, cachets, gelcaps, solutions, suspensions and the like. Tablets or capsules can be prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated for slow release, controlled release or sustained release of a prophylactic or therapeutic agent(s).

The pharmaceutical compositions of the invention may be formulated for parenteral administration by injection, e.g., by bolus injection or continuous infusion. Formulations for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical compositions of the invention may also be formulated in rectal compositions such as suppositories or retention enemas, e.g., containing conventional suppository bases such as cocoa butter or other glycerides.

In addition to the formulations described previously, the compositions of the invention may also be formulated as a depot preparation. Such long acting formulations may be administered by implantation (for example, subcutaneously or intramuscularly) or by intramuscular injection. Thus, for example, the pharmaceutical compositions may be formulated with suitable polymeric or hydrophobic materials (for example as an emulsion in an acceptable oil) or ion exchange resins, or as sparingly soluble derivatives, for example, as a sparingly soluble salt.

Generally, the ingredients of pharmaceutical compositions of the invention are supplied either separately or mixed together in unit dosage form, for example, as a dry lyophilized powder or water free concentrate in a hermetically sealed container such as an ampoule or sachette indicating the quantity of active agent. Where the pharmaceutical composition is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients may be mixed prior to administration.

For antibodies, antigen-binding antibody fragments, fusion polypeptides, and analogs of the invention, the dosage administered to a subject is generally from about 5 µg/kg to about 10 mg/kg, more preferably from about 20 µg/kg to about 5 mg/kg of the subject's body weight, most preferably from about 100 μg/kg to about 5 mg/kg. The dosage can be administered up to about 6 treatments over a period of weeks to months, as determined by the administering physician. Generally, human antibodies have a longer half-life within the human body than antibodies from other species due to the immune response to the foreign polypeptides. Thus, lower dosages and less frequent administration of human antibodies are often possible. Further, the dosage and frequency of administration of antibodies of the invention or fragments thereof may be reduced by enhancing uptake and tissue penetration of the antibodies by modifications such as, for example, lipidation.

The precise dose to be employed in the formulation will also depend on the route of administration, and the seriousness of the condition, and should be decided according to the judgment of the practitioner and each patient's circumstances in view of published clinical studies. Effective doses may be extrapolated from dose-response curves derived from in vitro or animal model test systems.

In one embodiment, a pharmaceutical composition of the invention is packaged in a hermetically sealed container such as an ampoule or sachette indicating the quantity of the antibody, antigen-binding antibody fragment, fusion polypeptide or analog. In another embodiment, a pharmaceutical composition of the invention is supplied as a dry sterilized lyophilized powder or water free concentrate in a hermetically sealed container and can be reconstituted, e.g., with water or saline to the appropriate concentration for administration to a subject. In yet another embodiment, a pharmaceutical composition is suspended in liquid form in a hermetically sealed container indicating the quantity and concentration of the antibody, antigen-binding antibody fragment, fusion polypeptide or analog.

In yet another embodiment, a pharmaceutical composition of the invention is supplied in a hermetically sealed container at a unit dosage of at least about 5 mg, more preferably at least about 1 mg, more preferably at least about 2 mg, 5 mg, 10 mg, 15 mg, 25 mg, 35 mg, 45 mg, 50 mg, 75 mg, 100 mg, 200 mg, 300 mg, 400 mg, or 500 mg. When supplied in liquid form, the pharmaceutical composition may be supplied in such a sealed container in a concentration of at least 1 mg/ml.

The present invention also provides a method of preparing a pharmaceutical composition of the invention, comprising admixing an antibody, antigen-binding antibody fragment, fusion polypeptide or analog of the invention with a pharmaceutically acceptable carrier.

5.6. Articles of Manufacture of the Invention

In still another aspect, the present invention provides an article of manufacture comprising packaging material and a pharmaceutical composition of the invention contained within the packaging material, said pharmaceutical composition in a form suitable for administration to a subject, preferably a human, or in a format that can be diluted or reconstituted for administration to the subject. In one embodiment, the article of manufacture further comprises printed instructions and/or a label directing the use or administration of the pharmaceutical composition. The instructions and/or label can, for example, suggest a dosing regimen for the prevention or treatment of one or more symptoms of a CA 125/O772P-related disorder, such as a cell proliferative disorder, for example cancer, e.g., ovarian, uterine, breast, or lung cancer. Thus, instructions and/or label can provide informational material that advises the physician, technician or subject on how to appropriately prevent, manage, treat or ameliorate a CA 125/O772P-related disorder or one or more symptoms of said disorder, for example, a cell proliferative disorder, such as cancer, e.g., ovarian cancer.

As with any pharmaceutical product, the packaging material and container of the articles of manufacture of the invention are designed to protect the stability of the product during storage and shipment. More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical composition of the invention contained within said packaging material.

5.7. Methods of Identifying Antibodies and Antigen-Binding Antibody Fragments that Preferentially Bind Cell-Associated CA 125/O772P The present invention provides a method to assist in identifying an antibody or antigen-binding antibody fragment that preferentially binds cell-associated CA 125/O772P relative to shed CA 125/O772P. In one embodiment, a method for identifying an antibody or antigen-binding antibody fragment that preferentially binds cell-associated CA 125/O772P comprises contacting an antibody or antigen-binding antibody fragment with a peptide comprising cell-associated CA 125/O772P in the presence of shed CA 125/O772P under conditions that allow binding of the antibody or antigen-binding antibody fragment to either said peptide comprising cell-associated CA 125/O772P or shed CA 125/O772P. After incubating, the shed CA 125/O772P (with or without antibody or antigen-binding antibody fragment bound) and unbound antibody or antigen-binding antibody fragment are removed, and the amount of antibody or antigen-binding antibody fragment bound to the peptide comprising cell-associated CA 125/O772P is measured. If the antibody or antigen-binding antibody fragment of the method satisfies any one of the three embodiments set forth above for "preferential binding," then said antibody or antigen-binding antibody fragment is one that preferentially binds cell-associated CA 125/O772P polypeptide relative to shed CA 125/O772P polypeptide. In a preferred embodiment, the ratio of shed CA 125/O772P to cell-associated CA 125/O772P to cell-associated CA 125/O772P in the reaction mixture is about 25:1 (wt/wt.). As part of this method, cell-associated CA 125/O772P can be immobilized on a solid surface. For example, the method can be performed in an ELISA format.

In another embodiment, the invention provides a method to assist in identifying an antibody, or antigen-binding antibody fragment, that preferentially binds cell-associated CA 125/O772P comprises contacting an antibody, or antigen-binding fragment, with a peptide comprising cell-associated CA 125/O772P and shed CA 125/O772P (e.g., about a 25-fold (weight/Weight) excess amount), under conditions that allow binding of the peptide comprising cell-associated CA 125/O772P to the antibody or antigen-binding antibody fragment, removing unbound peptide comprising cell-associated CA 125/O772P, measuring the amount of peptide comprising cell-associated CA 125/O772P bound by the antibody, or antigen-binding fragment, and comparing the amount measured to the amount of peptide comprising cell-associated CA 125/O772P the antibody or antigen-binding antibody fragment can bind in the absence of such amount of shed CA 125/O772P. If the antibody or antigen-binding antibody fragment of the method satisfies any one of the three embodiments set forth above for "preferentially binds," then said antibody or antigen-binding antibody fragment is one that preferentially binds cell-associated CA 125/O772P polypeptide relative to shed CA 125/O772P polypeptide. As part of this method the antibody, or antigen-binding antibody fragment can be immobilized on a solid surface, for example, the method can be performed in an ELISA format. The teaching provided herein, coupled with standard techniques well-known to those of skill in the art, can be utilized in practicing such methods for identification of antibodies, or antigen-binding antibody fragments, of the invention. For example, among the assays that can be utilized in identifying such antibodies or antigen-binding antibody fragments is the ELISA Competition Assay described in Section 6 and its subsections, below.

In yet another embodiment, the invention provides a method to assist in identifying an antibody, or antigen-binding antibody fragment, that preferentially binds cell-associated CA 125/O772P comprises contacting an antibody, or antigen-binding fragment, with a cell that expresses CA 125/O772P and with an amount, e.g., at least about 0.05 mg/ml, of shed CA 125/O772P under conditions that allow binding of the CA 125/O772P to the antibody or antigen-binding antibody fragment, removing unbound cells, measuring the amount of cells expressing CA 125/O772P bound by the antibody, or antigen-binding fragment, and comparing the amount measured to the amount of cells expressing CA 125/O772P that binds the antibody or antigen-binding antibody fragment in the absence of such an amount of shed CA 125/O772P. If the antibody or antigen-binding antibody fragment of the method satisfies any one of the three embodiments set forth above for "preferentially binds," then said antibody or antigen-binding antibody fragment is one that preferentially binds cell-associated CA 125/O772P polypeptide relative to shed CA 125/O772P polypeptide. Such a method can, for example, be performed wherein the measuring is performed by flow cytometry techniques, including, e.g., fluorescence activated cell sorting. The teaching provided herein, coupled with standard techniques well known to those of skill in the art, can be utilized in practicing such methods for identification of antibodies, or antigen-binding antibody fragments, of the invention. For example, among the assays that can be utilized in identifying such antibodies or antigen-binding antibody fragments are the Flow Cytometry Competition Assay in Section 6 and its subsections, below.

Among the embodiments of the present invention are antibodies and antigen-binding antibody fragments that preferentially bind cell-associated CA 125/O772P and that are specific for CA 125/O772P. Antibodies that are specific for CA 125/O772P can routinely be identified by, for example, utilizing the ELISA Specificity Assay and the Flow Cytometry Specificity Assay described, below, in Section 6 and its subsections. As such, the present invention also provides methods for identifying antibodies and antigen-binding antibody fragments that are specific for CA 125/O772P and which also preferentially bind cell-associated CA 125/O772P. In one such embodiment, first, an antibody or antigen-binding antibody fragment that is specific for CA 125/O772P is identified, e.g., by utilizing a ELISA Specificity Assay and/or a Flow Cytometry Specificity Assay. The antibody or antigen-binding antibody fragment is then tested for an ability to preferentially bind cell-associated CA 125/O772P utilizing, e.g., one of the methods described herein.

Also among the embodiments of the present invention are antibodies and antigen-binding antibody fragments that preferentially bind cell-associated CA 125/O772P and that bind the peptide of FIG. 1 (SEQ ID NO: 1) with a of less than about 100 nM, less than about 10 nM, less than about 1 nM, less than about 100 pM, or less than about 10 pM as measured by the BIAcore Affinity Assay, which is described in Section 6.4. Such antibodies can routinely be identified by, for example, adopting the ELISA Affinity Assay described below in Section 6 and its subsections. As such, the present invention also provides methods for identifying antibodies and antigen-binding antibody fragments that preferentially bind cell-associated CA 125/O772P and also bind cell-associated CA 125/O772P with at least a certain minimum level of affinity. In one such embodiment, first, an antibody or antigen-binding antibody fragment is identified that preferentially binds cell-associated CA 125/O772P utilizing, e.g., one of the methods described herein. The antibody or antigen-binding antibody fragment is then tested for an ability to bind cell-associated CA 125/O772P (or a peptide comprising the same) with a $K_d$ of less than about 100 nM, less than about 10 nM, less than about 1 nM, less than about 100 pM, or less than about 10 pM, utilizing, for example, one of the techniques described herein.

Embodiments of the present invention also include antibodies and antigen-binding antibody fragments that preferentially bind cell-associated CA 125/O772P and that exhibit an ability to mediate lysis of CA 125/O772P-positive cells, e.g., tumor cells. Such antibodies and antigen-binding antibody fragments can routinely be identified by, for example, performing the ADCC and/or CDC assays described below in Section 6 and its subsections. As such, the present invention provides methods for identifying antibodies or antigen-binding antibody fragments that preferentially bind cell-associated CA 125/O772P and which also exhibit an ability to mediate lysis of CA 125/O772P-positive cells. In one such embodiment, an antibody or antigen-binding antibody fragment is identified that preferentially binds cell-associated CA 125/O772P utilizing, e.g., one of the methods presented herein. The antibody or antigen-binding antibody fragment is then tested for an ability to mediate lysis of CA 125/O772P-positive cells via, for example, an ADCC and/or CDC assay as described herein.

Embodiments of the present invention also include antibodies and antigen-binding antibody fragments that preferentially bind CA 125/O772P and that exhibit an ability to inhibit or slow growth of CA 125/O772P-positive tumors. Such antibodies can routinely be identified by, for example, performing in vivo assays previously described, such as those found in Treskes et al., Eur. J. Cancer. 30A(2):183-187 (1994); Ahmad et al., Oncol. Res. 11(6):273-280 (1999); and Kievit et al., Int. J. Radiat. One. Biol. Phys. 38(2):419-428 (1997), each of which is incorporated herein by reference in its entirety. As such, the present invention also provides methods for identifying antibodies or antigen-binding antibody fragments that preferentially bind CA 125/O772P and which also exhibit an ability to inhibit growth of CA 125/O772P-positive tumor cells. In one such embodiment, an antibody or antigen-binding antibody fragment is identified that preferentially binds cell-associated CA 125/O772P utilizing, e.g., one of the methods presented herein. The antibody or antigen-binding antibody fragment is then tested for an ability to inhibit growth of CA 125/O772P-positive tumor cells via, for example, testing the antibody or antigen-binding antibody fragment in a system such as one of the in vivo systems described herein.

5.8. Methods of Preventing, Treating, Managing, or Ameliorating a Symptom of a CA 125/O772P-Related Disorder The present invention provides methods for prevention, treatment, or management of a CA 125/O772P-related disorder, or amelioration of a symptom of a CA 125/O772P-related disorder. For example, the present invention provides methods for the prevention, treatment, management, or amelioration of a symptom of a cell proliferative disorder, by administering to a subject in need of such prevention, treatment, management, or amelioration an amount of an antibody, antigen-binding antibody fragment, or analog effective to effectuate the desired outcome in the subject.

As discussed throughout, the antibodies and antigen-binding antibody fragments of the invention are those that preferentially bind cell-associated CA 125/O772P. Likewise the fusion polypeptides and analogs of the invention also preferentially bind cell-associated CA 125/O772P. As also noted herein, due to the fact that cell-associated CA 125/O772P, prior to CA 125/O772P shedding, is present or part of CA 125/O772P, it is noted that antibodies, antigen-binding antibody fragments, fusion polypeptides, and analogs of the invention can also bind CA 125/O772P. Thus, while not wishing to be bound by any particular mechanism or theory thereof, it is noted that the methods described in this section can be effectuated, at least in part, by binding of the administered antibody, antigen-binding antibody fragments, fusion polypeptides, or analogs for the invention to pre-shed CA 125/O772P in addition to, or instead of, their binding to post-shed cell-associated CA 125/O772P.

In one embodiment, the methods of the invention relate to prevention, treatment, management, or amelioration of a symptom of a cancer. For example, these methods of the invention relate to prevention, treatment, management, or amelioration of a symptom of cancers or cancer-associated disorders, said cancers including but not limited to such cancers as carcinomas, sarcomas, myelomas, leukemias, lymphomas and mixed type cancers. In a particular embodiment, such methods of the invention relate to prevention, treatment, management, or amelioration of ovarian cancer, cervical cancer, uterine cancer, breast cancer or lung cancer, or a symptom thereof. In a preferred embodiment of such methods of the invention, such methods relate to prevention, treatment, management, or amelioration of a symptom of ovarian cancer.

In another embodiment, the present invention provides a method for treating a CA 125/O772P-related disorder, or ameliorating a symptom thereof, comprising administering to a subject in need of such treatment or amelioration, an antibody, antigen-binding fragment of an antibody, fusion polypeptide or analog of the invention in an amount sufficient to treat the cell proliferative disorder or ameliorate a symptom thereof. The CA 125/O772P-related disorder can, for example, be a cell proliferative disorder such as cancer and can include, e.g., ovarian, cervical cancer, uterine cancer, breast cancer or lung cancer. Such an embodiment is preferably practiced where the antibody, antigen-binding antibody fragment, fusion polypeptide or analog of the invention is conjugated to a cytotoxic agent useful in treating the cell-proliferative disease such as those agents recited in Section 5.2. In a particular embodiment, the cytotoxic agent is a radioisotope. In a further particular embodiment, the radioisotope is selected from the group consisting of $^{125}I$, $^{131}I$, $^{111}In$, $^{99m}Tc$ and $^{90}Y$. Such an embodiment can be practiced as part of a combination cancer therapy, by, for example, further administering a chemotherapeutic agent, such as paclitaxel or cisplatin, or radiation treatment to the subject.

In yet another embodiment, the present invention provides a method for preventing a CA 125/O772P-related disorder or a symptom of a CA 125/O772P-related disorder, comprising administering to a subject in need of such prevention, an antibody, antigen-binding fragment of an antibody, fusion polypeptide or analog of the invention in an amount sufficient to prevent the CA 125/O772P-related disorder, or a symptom thereof. The CA 125/O772P-related disorder can, for example, be a cell proliferative disorder such as cancer and can include, e.g., ovarian, cervical cancer, uterine cancer, breast cancer or lung cancer.

In additional embodiments, the CA 125/O772P-related disorder is a bone cancer, for example, Ewing's sarcoma, osteosarcoma, rhabdomyosarcoma, or another soft-tissue sarcoma. In another embodiment, the CA 125/O772P-related disorder is a brain tumor, for example, oligodendroglioma; ependymoma, menengioma, lymphoma, schwannoma, or medulloblastoma. In another embodiment, the CA 125/O772P-related disorder is a breast cancer, for example, ductal carcinoma in situ of the breast. In another embodiment, the CA 125/O772P-related disorder is an endocrine system cancer, for example, adrenal, pancreatic, parathyroid, pituitary, or thyroid cancers. In another embodiment, the CA 125/O772P-related disorder is a gastrointestinal cancer, for example, anal, colorectal, esophogeal, gallbladder, gastric, liver, pancreatic, or small intestine cancer. In another embodiment, the CA 125/O772P-related disorder is a gynecological cancer, for example, cervical, endometrial, uterine, fallopian tube, gestational trophoblastic disease, choriocarcinoma, ovarian, vaginal, or vulvar cancer. In another embodiment, the CA 125/O772P-related disorder is a head and neck cancer, for example, laryngeal, oropharyngeal, parathyroid or thyroid cancer. In another embodiment, the CA 125/O772P-related disorder is a leukemic cancer, for example, acute lymphocytic leukemia, acute myelogenous leukemia, chronic lymphocytic leukemia, chronic myelogenous leukemia, hairy cell leukemia, or a myeloproliferative disorder. In another embodiment, the CA 125/O772P-related disorder is a lung cancer, for example, a mesothelioma, a non-small cell lung cancer, or a small cell lung cancer. In another embodiment, the CA 125/O772P-related disorder is a lymphoma, for example, AIDS-related lymphoma, cutaneous T cell lymphoma, Hodgkin's disease, or non-Hodgkin's disease. In another embodiment, the CA 125/O772P-related disorder is metastatic cancer. In another embodiment, the CA 125/O772P-related disorder is a myeloma, for example, a multiple myeloma. In another embodiment, the CA 125/O772P-related disorder is a pediatric cancer, for example, a brain tumor, Ewing's sarcoma, leukemia (e.g., acute lymphocytic leukemia or acute myelogenous leukemia), liver cancer, a lymphoma (e.g., Hodgkin's lymphoma or non-Hodgkin's lymphoma), neuroblastoma, retinoblastoma, a sarcoma (e.g., osteosarcoma, rhabdomyosarcoma or other soft-tissue sarcomas), or Wilms' Tumor. In another embodiment, the CA 125/O772P-related disorder is penile cancer. In another embodiment, the CA 125/O772P-related disorder is prostate cancer. In another embodiment, the CA 125/O772P-related disorder is a skin cancer, for example, cutaneous T cell lymphoma, mycosis fungoides, Kaposi's sarcoma, or melanoma. In another embodiment, the CA 125/O772P-related disorder is testicular cancer. In another embodiment, the CA 125/O772P-related disorder is a thyroid cancer, for example, papillary, follicular, medullary, anaplastic, or undifferentiated thyroid carcinoma. In another embodiment, the CA 125/O772P-related disorder is a urinary tract cancer, for example, bladder, kidney, or urethral cancer. In another embodiment, the CA 125/O772P-related disorder or cancer-related condition is ataxia-telangiectasia, carcinoma of unknown primary origin, Li-Fraumeni syndrome, or thymoma.

In one embodiment of such methods of the invention, an antibody or antigen-binding fragment of the invention is administered. In another embodiment, a monoclonal antibody or antigen-binding monoclonal antibody fragment is administered. Typically, the antibody or antigen-binding antibody fragment is administered at a dosage concentration of about 5 µg/kg to about 10 mg/kg, more preferably from about 20 µg/kg to about 5 mg/kg, and most preferably from about 100 µg/kg to about 5 mg/kg of the subject's body weight.

In general, the methods described herein can be utilized via administration of a pharmaceutical composition of the invention. The toxicity and/or efficacy of the compositions administered according to the particular protocols practiced as part of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred. While compositions that exhibit toxic side effects may be used, it is preferable that a delivery system be utilized that targets such compositions to the site of affected tissue, e.g., ovarian tissue, thereby reducing side effects.

Data obtained from the cell culture assays and animal studies can be used in formulating a range of dosage of compositions for use in humans. The dosage of such compositions lies preferably within a range that results in circulating concentrations that include the $ED_{50}$ with little or no toxicity. The dosage may vary within this range depending upon the dosage form employed and the route of administration utilized. For any agent used in the methods of the invention, the therapeutically effective dose can be estimated initially from cell culture assays. A dose may be formulated in animal models to achieve a circulating plasma concentration range that includes the $IC_{50}$ the concentration of the compound that achieves a half-maximal inhibition of one or more symptoms) as determined in cell culture assays, e.g., proliferation assays. Such information can be used to more accurately determine useful doses in humans. Levels in plasma may be measured, for example, by high performance liquid chromatography.

Various delivery systems are known and can be used to administer an antibody, antigen-binding antibody fragment, fusion polypeptide or analog of the invention, e.g., encapsulation in liposomes (see, e.g., Langer, Science 249(4976): 1527-1533 (1990); Treat et al., in *Liposomes in the Therapy of Infectious Disease and Cancer*, Lopez-Berestein et al., eds., Liss (1989) at pages 353-365), microparticles, microcapsules, or recombinant cells capable of expressing the antibody, antigen-binding antibody fragment, fusion polypeptide or analog of the invention.

Methods of administering an antibody, antigen-binding antibody fragment, fusion polypeptide or analog of the invention, or pharmaceutical composition comprising same include, but are not limited to, parenteral (e.g., intradermal, intramuscular, intraperitoneal, intravenous and subcutaneous administration), epidural, or mucosal (e.g., intranasal and oral) routes of administration. See, e.g., U.S. Pat. Nos. 5,679,377, 5,702,727, 5,783,193, 5,817,624, 6,074,689, 6,156,731, 6,174,529, 6,187,803, 6,331,175, and 6,387,406. In a specific embodiment, an antibody, antigen-binding antibody fragment, fusion polypeptide or analog of the invention, or a pharmaceutical composition thereof is administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may also be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. RE37,525, 5,290,540, 5,855,913, 5,874,064, 5,934,272, 5,985,309, 5,985,320, 6,019,968, 6,165,463, 6,358,530, and 6,402,733 and PCT Publication No. WO 99/66903, each of which is incorporated herein by reference in its entirety. In one embodiment, an antibody, a fusion protein, a conjugated molecule, or a pharmaceutical composition can be administered using Alkermes AIR™ pulmonary drug delivery technology (Alkermes, Inc., Cambridge, Mass.).

In one preferred embodiment, the pharmaceutical composition is formulated in accordance with routine procedures so that it is adapted for intravenous administration to human beings. Typically, pharmaceutical compositions for intravenous administration are solutions in sterile isotonic aqueous buffer. Where necessary, the composition may also include a solubilizing agent and a local anesthetic to ease pain at the site of the injection.

In another specific embodiment, it may be desirable to administer the pharmaceutical compositions of the invention locally to the area in need of treatment. This may be achieved by local infusion, injection, or by means of an implant, said implant being of a porous, non-porous, or gelatinous material.

In yet another embodiment, the methods are practiced as part of a combination therapy, for example, a combination cancer therapy. Such combination cancer therapy can include, for example, administration of a chemotherapeutic agent, e.g., cisplatin, ifosfamide, paclitaxel, taxanes, a topoisomerase I inhibitor (e.g., CPT-11, topotecan, 9-AC, or GG-211), gemcitabine, mitomycin, emetine, etopside, tenopside, vincristine, vinblastine, colchicin, doxordubicin, daunorubicin, dihydroxy anthracin dione, mitoxantrone, mithramycin, vinorelbine, oxaliplatin, 5-fluorouracil (5-FU), leucovorin, vinorelbine, temodal, or taxol. Such combination cancer therapy can alternatively or additionally include, but is not limited to, radiation therapy.

The use of the term "combination therapy" or "combination cancer therapy" does not limit the order in which agents or treatments are administered to a subject with a CA 125/O772P-related disorder. For example, the agents of the combination therapy can be administered concurrently, sequentially in any order or cyclically to a subject. In a preferred embodiment, the two or more components of the combination therapy are administered to a subject concurrently. The term "concurrently" is not limited to the administration of two or more agents at exactly the same time, but rather it is meant that the agents are administered to a subject in a sequence and within a time interval such that the agents can act together to provide an increased benefit than if they were administered otherwise.

The agents to be administered as part of combination therapy methods can, for example, be administered to a subject in the same pharmaceutical composition. Alternatively, the agents of the combination therapies can be administered to a subject in separate pharmaceutical compositions, by the same or different mutes of administration.

5.9. Methods of Diagnosing a CA 125/O772P-Related Disorder

In another aspect, the present invention also provides methods for diagnosing a CA 125/O772P-related disorder or predisposition to a CA 125/O772P-related disorder. In one embodiment, labeled antibodies, antigen-binding antibody fragments, fusion polypeptides, and analogs of the invention can be used for diagnostic purposes to detect, diagnose, or monitor a CA 125/O772P-related disorder such as cancer.

For example, antibodies, antigen-binding antibody fragments, fusion polypeptides, and analogs of the invention can be used to assay cell-associated CA 125/O772P levels in a biological sample using classical immunohistological methods as described herein or as known to those of skill in the art (see, e.g., Jalkanen et al., J. Cell. Biol. 101(3):976-984 (1985); Jalkanen et al., J. Cell. Biol. 105(6 Pt 2):3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include, for example, enzyme labels, such as, alkaline phosphatase, glucose oxidase; radioisotopes, such as iodine ($^{125}$I, $^{131}$I), carbon ($^{14}$C), sulfur ($^{35}$S), tritium ($^{3}$H), indium ($^{111}$In), and technetium ($^{99m}$Tc); luminescent labels, such as luminol; and fluorescent labels, such as fluorescein and rhodamine.

One aspect of the invention is the detection and diagnosis of a predisposition to cancer, in particular, ovarian cancer, in a human. In one embodiment, diagnosis comprises: a) administering (for example, parenterally, subcutaneously, or intraperitoneally) to a subject an amount of a labeled antibody, antigen-binding antibody fragment, fusion polypeptide, or analog that preferentially binds cell-associated CA 125/O772P effective for diagnosis, and b) detecting the labeled antibody, antigen-binding antibody fragment, fusion polypeptide, or analog in the subject in order to make said diagnosis. In accordance with this embodiment, the antibody, antigen-binding fragment, fusion polypeptide, or analog is preferably labeled with an imaging moiety which is detectable using an imaging system known to one of skill in the art. Background level can be determined by various methods including, comparing the amount of labeled molecule detected to a standard value previously determined for a particular system.

Presence of the labeled molecule can be detected in the subject using methods known in the art for in vivo scanning. These methods depend upon the type of label used. Skilled artisans will be able to determine the appropriate method for detecting a particular label. Methods that may be used in the diagnostic methods of the invention include, but are not limited to, computed tomography (CT), whole body scan such as positron emission tomography (PET), magnetic resonance imaging (MRI), and sonography.

In a specific embodiment, the molecule is labeled with a radioisotope and is detected in the subject using a radiation responsive surgical instrument (see, e.g., U.S. Pat. No. 5,441,050). In another embodiment, the molecule is labeled with a fluorescent compound and is detected in the subject using a fluorescence responsive scanning instrument. In another embodiment, the molecule is labeled with a positron emitting metal and is detected in the subject using PET. In yet another embodiment, the molecule is labeled with a paramagnetic label and is detected in the subject using MRI.

It will be understood in the art that the size and weight of the subject, as well as the type of the imaging system used, will determine the type and quantity of imaging moiety needed to produce useful diagnostic images. In the case of a $^{99m}$Tc-containing radioisotope moiety, for a human subject, the quantity of radioactivity injected will normally range from about 5 to 20 millicuries. The labeled antibody, antigen-binding antibody fragment, fusion polypeptide, or analog will then preferentially accumulate at the location of cells which exhibit a cell-associated CA 125/O772P polypeptide. In vivo tumor imaging is described in Burchiel et al., "Immunopharmacokinetics of Radiolabeled Antibodies and Their Fragments", in *Tumor Imaging: The Radiochemical Detection of Cancer*, Burchiel et al., eds., Masson Publishing Inc. (1982) at Chapter 13.

Depending on several variables, including the type of label used and the mode of administration, the time interval following the administration for permitting the labeled molecule to preferentially concentrate at sites in the subject and for unbound labeled molecule to be cleared to background level may be about 6 to 48 hours or about 6 to 24 hours or about 6 to 12 hours. In another embodiment the time interval following administration is about 5 to 20 days or about 5 to 10 days.

In one embodiment, monitoring of a CA 125/O772P-related disorder, e.g., cancer, can be carried out by repeating the imaging method at several time points, for example, at one month after initial diagnosis, at six months after initial diagnosis, and/or at one year after initial diagnosis, and so forth.

Included within the invention are methods of diagnosing or monitoring cancer comprising administering to a subject in need of such diagnosis or monitoring an amount of the labeled antibody, antigen-binding antibody fragment, fusion polypeptide, or analog that preferentially binds cell-associated CA 125/O772P sufficient for detection, and detecting the labeled antibody, antigen-binding antibody fragment, fusion polypeptide, or analog bound to an organ or tissue of the subject. Furthermore, the present invention provides methods of detecting cell-associated CA 125/O772P in a biological sample comprising contacting a labeled antibody, antigen-binding antibody fragment, fusion polypeptide, or analog that preferentially binds cell-associated CA 125/O772P, and detecting antibody, antigen-binding antibody fragment, fusion polypeptide, or analog bound to the sample.

In these embodiments, the amount of labeled molecule bound to cell-associated CA 125/O772P can then be compared to a standard amount or to a control, or to the amount previously detected in the subject at an earlier time point.

5.10. Methods of Producing Antibodies

Antibodies of the invention can be produced by any method known in the art for the synthesis of antibodies, for example, by hybridoma technology, chemical synthesis or preferably, by recombinant expression techniques.

Polyclonal antibodies can be produced by various procedures well-known in the art. For example, a human CA 125/O772P comprising a cell-associated CA 125/O772P polypeptide can be administered to various host animals including, but not limited to, rabbits, mice, rats, and horses, to induce the production of sera containing polyclonal antibodies specific for the human antigen. Various adjuvants may be used to increase the immunological response, depending on the host species, and include but are not limited to, Freund's (complete or incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught in Harlow et al., *Antibodies: A Laboratory Manual*, 2$^{nd}$ ed., Cold Spring Harbor Laboratory Press (1988); or Hammerling et al., *Monoclonal Antibodies and T-Cell Hybridomas*, Elsevier (1981) at pages 563-681), which are hereby incorporated by reference in their entireties.

Methods for producing and screening for specific antibodies using hybridoma technology are routine and well known in the art. Briefly, in one example, mice can be immunized with a CA 125/O772P polypeptide, e.g., a cell-associated CA 125/O772P polypeptide and once an immune response is detected, e.g., antibodies specific for the antigen are detected in the mouse serum, the mouse spleen is harvested and splenocytes isolated. The splenocytes are then fused by well known techniques to any suitable myeloma cells, for example, cells from cell line SP2/0-Ag14 available from the ATCC (Accession No. CRL-1581). Hybridomas are selected and cloned by limiting dilution. The hybridoma clones are then assayed by methods known in the art for cells that secrete antibodies capable of binding a cell-associated CA 125/O772P. Ascites fluid, which generally contains high levels of antibodies, can be generated by injecting mice with positive hybridoma clones.

Accordingly, the present invention provides methods of generating monoclonal antibodies as well as antibodies produced by such methods comprising culturing a hybridoma cell secreting an antibody of the invention wherein, preferably, the hybridoma is generated by fusing splenocytes isolated from a mouse immunized with a CA 125/O772P polypeptide, e.g., a cell-associated CA 125/O772P polypeptide, with myeloma cells, and then screening the hybridomas resulting from the fusion for hybridoma clones that secrete an antibody able to bind to the CA 125/O772P polypeptide, e.g., a cell-associated CA 125/O772P polypeptide.

Antibody fragments which recognize specific epitopes may be generated by any technique known to those of skill in the art. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. Phage expressing an antigen binding domain that binds to a CA 125/O772P polypeptide antigen can be selected or identified with antigen, e.g., using labeled antigen or antigen bound or captured to a solid surface or bead. Examples of phage display methods that can be adapted so they can be used to make or identify the antibodies of the present invention include those disclosed in Brinkmann et al., J. Immunol. Methods. 182(1):41-50 (1995); Ames et al., J. Immunol. Methods. 184(2):177-186 (1995); Kettleborough et al., Eur. J. Immunol. 24(4):952-958 (1994); Persic et al., Gene. 187(1):9-18 (1997); Burton et al., Adv. Immunol. 57:191-280 (1994); PCT publication Nos. WO 91/10737 and WO 95/15982; EP 853,661; and U.S. Pat. Nos. 5,223,409, 5,403,484, 5,427,908, 5,516,637, 5,571,698, 5,580,717, 5,658,727, 5,667,988, 5,698,426, 5,712,089, 5,733,743, 5,780,225, 5,789,208, 5,821,047, 5,885,793, 5,969,108, 6,096,551, 6,140,470, 6,376,170, 6,265,150 and 6,335,163; each of which is incorporated herein by reference in its entirety.

As described in the above references, after phage selection, the antibody coding regions from the phage can be isolated and used to generate whole antibodies, including human antibodies, or a desired antigen binding fragment, and expressed in a host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in U.S. Pat. Nos. 5,595,898, 5,698,417, and 6,204,023; Mullinax et al., BioTechniques. 12(6):864-869 (1992); Sawai et al., Am. J. Reprod. Immunol. 34(1):26-34 (1995); and Better et al., Science. 240(4855):1041-1043 (1988); each of which is incorporated herein by reference in their entireties.

To generate whole antibodies, PCR primers including VH or VL nucleotide sequences, a restriction site, and a flanking sequence to protect the restriction site can be used to amplify the VH or VL sequences in scF$_v$ clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. Preferably, the vectors for expressing the VH or VL domains can comprise an EF-1α promoter, a secretion signal, a cloning site for the variable domain, constant domains, and a selection marker such as neomycin. The VH and VL domains may also be cloned into one vector expressing the necessary constant regions. The heavy chain expression vectors and light chain expression vectors are then co-transfected into cell lines to generate stable or transient cell lines that express full-length antibodies, e.g., IgG, using techniques known to those of skill in the art.

For some uses, particularly in vivo use of antibodies in humans and in vivo detection assays, it may be preferable to use chimeric, humanized, or completely human antibodies. A chimeric antibody is a molecule in which different portions of the antibody are derived from immunoglobulin molecules from different species. For example, and not by way of limitation, a chimeric antibody may have light and/or heavy chain variable regions derived from a murine antibody and light and/or heavy chain constant regions derived from a human immunoglobulin. Methods for producing chimeric antibodies are known in the art. See, e.g., Morrison, Science. 229(4719): 1202-1207 (1985); Oi et al., BioTechniques. 4(3):214-221 (1986); Gillies et al., J. Immunol. Methods. 125(1-2):191-202 (1989); and U.S. Pat. Nos. 4,816,397, 4,816,567, and 5,807,715, each of which is incorporated herein by reference in their entirety.

A humanized antibody is an antibody that comprises a human framework, including a human constant region, and one or more CDRs from an antibody of a non-human species, e.g., a murine species. Such humanized antibodies can routinely be generated utilizing a variety of techniques known in the art including, for example, CDR-grafting (EP 239,400; PCT publication No. WO 91/09967; and U.S. Pat. Nos. 5,225,539, 5,530,101, 5,585,089, 5,766,886, 5,859,205, 6,180,370, and 6,407,213), veneering or resurfacing (U.S. Pat. No. 5,639,641; EP 519,596; Padlan, Mol. Immunol. 28(4/5):489-498 (1991); Studnicka et al., Protein Eng. 7(6):805-814 (1994); and Roguska et al., Proc. Natl. Acad. Sci. USA. 91(3):969-973 (1994)), and chain shuffling (U.S. Pat. Nos. 5,565,332 and 6,455,253). In a preferred embodiment, humanized antibodies comprise a CDR having an amino acid sequence of any one of the CDRs listed in Table 1, Table 2, Table 3, Table 4, Table 5 or Table 6 and human framework regions. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., U.S. Pat. Nos. 5,585,089, 5,770,196, and 5,869,619; and Riechmann at al., Nature. 332(6162):323-327 (1988), each of which is incorporated herein by reference in their entireties.

Completely or fully human antibodies are desirable for therapeutic treatment of human subjects. Human antibodies can be made by a variety of methods known in the art, including the phage display methods described above using antibody libraries derived from human immunoglobulin sequences. See also U.S. Pat. Nos. 4,444,887, 4,716,111, 5,916,771, 5,939,598, 6,075,181, 6,114,598, 6,150,584, 6,162,963, 6,235,883; PCT publication WO 98/46645; and EP 463,151; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a CA 125/O772P polypeptide, such as a cell-associated CA 125/O772P polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al., Int. Rev. Immunol. 13(1):65-93 (1995). For a detailed discussion of this technology for producing human antibodies and human monoclonal antibodies and protocols for producing such antibodies, see, e.g., U.S. Pat. Nos. 5,413,923, 5,625,126, 5,633,425, 5,569,825, 5,661,016, 5,545,806, 5,814,318, 5,939,598, 6,075,181, 6,091,001, 6,114,598, 6,150,584, and 6,162,963, which are incorporated by reference herein their entirety. In addition, companies such as Abgenix, Inc. (Fremont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. See, e.g., Jespers et al., Bio/Technology. 12(4): 899-903 (1994).

Further, the antibodies that specifically bind to an antigen can, in turn, be utilized to generate anti-idiotype antibodies that "mimic" an antigen using techniques well known to those skilled in the art, and anti-anti-idiotype antibodies that bind to the antigen can be prepared therefrom. See, e.g., Greenspan et al., FASEB J. 7(5):437-444 (1993); and Nisonoff, J. Immunol. 147(8):2429-2438 (1991).

5.11. Recombinant Expression of Antibodies and Polypeptides

Recombinant expression of an antibody, antigen-binding antibody fragment, fusion polypeptide or analog that preferentially binds cell-associated CA 125/O772P can be accomplished using an expression vector comprising a polynucleotide that encodes the antibody, antigen-binding antibody fragment, fusion polypeptide or analog of the invention. Once a polynucleotide encoding an antibody, antigen-binding antibody fragment, fusion polypeptide or analog of the invention has been obtained, the vector for the production of the antibody, antigen-binding antibody fragment, fusion polypeptide or analog may be produced by recombinant DNA technology using techniques well-known in the art. See, e.g., U.S. Pat. Nos. 4,816,567, 5,545,405, and 6,331,415, each of which is incorporated herein by reference in its entirety.

Methods which are well known to those skilled in the art can be used to construct expression vectors containing antibody, antigen-binding antibody fragment, fusion polypeptide or analog coding sequences and appropriate transcriptional and translational control signals. These methods include, for example, in vitro recombinant DNA techniques, synthetic techniques, and in vivo genetic recombination. The invention, therefore, provides replicable vectors comprising a nucleotide sequence encoding an antibody of the invention, antigen-binding antibody fragment of the invention, fusion polypeptide or analog of the invention, a heavy or light chain of an antibody, a heavy or light chain variable domain of an antibody or a portion thereof, or a heavy or light chain CDR, operably linked to a promoter. Such vectors may also include the nucleotide sequence encoding the constant region of the antibody molecule (see, e.g., EP 216,846, EP 323,997, and U.S. Pat. No. 5,122,464), and the variable domain of the antibody may be cloned into such a vector for expression of the entire heavy chain, the entire light chain, or both the entire heavy and light chains.

The expression vector is transferred to a host cell by conventional techniques and the transformed or transfected cells are then cultured by conventional techniques, under conditions that are conducive to, or permit, the production of an antibody, antigen-binding antibody fragment, fusion polypeptide or analog of the invention. Thus, the invention includes host cells containing a vector or polynucleotide encoding an antibody, antigen-binding antibody fragment, fusion polypeptide or analog of the invention or fragment thereof, or a heavy or light chain thereof, or portion thereof, or a single chain antibody of the invention, which polynucleotide molecule is operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibodies, antigen-binding, antibody fragments, fusion polypeptides or analogs of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express antibodies antigen-binding, antibody fragments, fusion polypeptides or analogs of the invention in situ. These include, but are not limited to, microorganisms such as bacteria (e.g., *E. coli* or *B. subtillis*) transformed with recombinant bacteriophage DNA, plasmid DNA or cosmid DNA expression vectors containing antibody, antigen-binding antibody fragment, fusion polypeptide or analog coding sequences; yeast (e.g., *Saccharomyces cervisiae, Pichia pastoris,* or *Pichia maetlanolica*) transformed with recombinant yeast expression vectors containing antibody, antigen-binding antibody fragment, fusion polypeptide or analog coding sequences; insect cell systems transfected with recombinant virus expression vectors (e.g., baculovirus) containing antibody, antigen-binding antibody fragment, fusion polypeptide or analog coding sequences; plant cell systems transfected with recombinant virus expression vectors (e.g., cauliflower mosaic virus, CaMV; tobacco mosaic virus, or TMV) or transformed with recombinant plasmid expression vectors (e.g., Ti plasmid) containing antibody, antigen-binding antibody fragment, fusion polypeptide or analog coding sequences; or mammalian cell systems (e.g., COS, CHO, BHK, 293, NS0, or 3T3 cells) harboring recombinant expression constructs containing promoters derived from the genome of mammalian cells (e.g., metallothionein promoter) or from mammalian viruses (e.g., the adenovirus late promoter or the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus are an effective expression system for antibodies (Foecking et al., Gene. 45(1):101-105 (1986) and Cockett et al., Bio/Technology. 8(7):662-667 (1990)). In a specific embodiment, the expression of nucleotide sequences encoding antibodies, antigen-binding antibody fragments, fusion polypeptides or analogs of the invention are regulated by a constitutive promoter, inducible promoter, cell type or tissue specific promoter.

In bacterial systems, a number of expression vectors may be advantageously selected depending upon the use intended for the antibody, antigen-binding antibody fragment, fusion polypeptide or analog being expressed. For example, when a large quantity of such a protein is to be produced, e.g., for the generation of pharmaceutical compositions of an antibody molecule, vectors which direct the expression of high levels of protein products that are readily purified may be desirable. Such vectors include, but are not limited to, the *E. coli* expression vector pUR278 (Ruther et al., EMBO J. 2(10):1791-1794 (1983)), in which the antibody coding sequence may be ligated individually into the vector in frame with the lacZ coding region so that a fusion protein is produced; pIN vectors (Inouye et al., Nucleic Acids Res. 13(9):3101-3110 (1985); Van Heeke et al., J. Biol. Chem. 264(10):5503-5509 (1989)); and the like. pGEX vectors may also be used to express foreign polypeptides as fusion proteins with glutathione 5-transferase (GST) (Hakes et al., Anal. Biochem. 202(2):293-298 (1992)). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example, the polyhedrin gene) of the virus and placed under control of an AcNPV promoter (for example, the polyhedrin promoter). See, e.g., Kumar et al., Biosci. Rep. 19(3):227-234 (1999).

In mammalian host cells, a number of viral-based expression systems may be utilized. In cases where an adenovirus is used as an expression vector, the antibody, antigen-binding antibody fragment, fusion polypeptide or analog coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule infected hosts (see, e.g., Logan et al., Proc. Natl. Acad. Sci. USA. 81(12):3655-3659 (1984)). Specific initiation signals may also be required for efficient translation of inserted coding sequences. These signals include the ATG initiation codon and adjacent sequences. Furthermore, the initiation codon must be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bitter et al., Methods Enzymol. 153:516-544 (1987)).

In addition, a host cell strain which modulates the expression of the inserted sequences, or modifies and processes the gene product in a specific desired fashion may be utilized. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression of the protein is preferred. For example, cell lines which stably express the antibody molecule may be engineered. Rather than using expression vectors which contain viral origins of replication, host cells can be transformed with DNA controlled by appropriate expression control elements (e.g., promoter sequences, enhancer sequences, transcription terminators, polyadenylation sites, etc.), and a selectable marker. Following the introduction of the foreign DNA, engineered cells may be allowed to grow for 1-2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to, the herpes simplex virus thymidine kinase (Wigler et al., Cell. 11(1):223-232 (1977)), hypoxanthineguanine phosphoribosyltransferase (Spring et al., Biochim. Biophys. Acta. 2118(2):158-162 (1994)), and adenine phosphoribosyltransferase (Lowy et al., Cell. 22(3):817-823 (1980)) genes can be employed in tk-, hgprt- or aprt-cells, respectively. Also, antimetabolite resistance can be used as the basis of selection for the following genes: dhfr, which confers resistance to methotrexate (Wigler et al., Proc. Natl. Acad. Sci. USA. 77(6):3567-3570 (1980); O'Hare et al., Proc. Natl. Acad. Sci. USA. 78(3):1527-1531 (1981)); gpt, which confers resistance to mycophenolic acid (Mulligan et al, Proc. Natl. Acad. Sci. USA. 78(4):2072-2076 (1981));

neo, which confers resistance to the aminoglycoside G-418 (Wu et al., Biotherapy. 3(1):87-95 (1991); Tolstoshev, Ann. Rev. Pharmacol. Toxicol. 33:573-596 (1993); Mulligan, Science. 260(5110):926-932 (1993); and Morgan et al., Ann. Rev. Biochem. 62:191-217 (1993)); and hygro, which confers resistance to hygromycin (Santerre et al., Gene 30(1-3):147-156 (1984)). Methods commonly known in the art of recombinant DNA technology may be routinely applied to select the desired recombinant clone, and such methods are described, for example, in *Current Protocols in Molecular Biology*, Ausubel et al., eds., John Wiley & Sons (1989-2002); Kriegler, *Gene Transfer and Expression, A Laboratory Manual*, Stockton Press (1990); Chapters 12 and 13 of *Current Protocols in Human Genetics*, Dracopoli et al., eds., John Wiley & Sons (1994); and Colbere-Garapin et al., J. Mol. Biol. 150(1):1-14 (1981), each of which is incorporated by reference herein their entireties.

The expression levels of an antibody, antigen-binding antibody fragment or fusion polypeptide molecule can be increased by vector amplification (for a review, see Bebbington et al., *The Use of Vectors Based on Gene Amplification for the Expression of Cloned Genes in Mammalian Cells in DNA Cloning*, Vol. 3, Academic Press (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3(2):257-266 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should preferably be placed before the heavy chain to avoid an excess of toxic free heavy chain (Proudfoot, Nature. 322(6079):562-565 (1986); and Kohler, Proc. Natl. Acad. Sci. USA. 77(4):2197-2199 (1980)). The coding sequences for the heavy and light chains may comprise cDNA or genomic DNA, or a combination thereof.

Once an antibody, antigen-binding antibody fragment, fusion polypeptide or analog of the invention has been produced by recombinant expression, it may be purified by any method known in the art for purification of an immunoglobulin molecule, for example, by chromatography (e.g., ion exchange, affinity, particularly by affinity for the specific CA 125/O772P antigen after initial Protein A purification, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

The following examples are presented by way of illustration and not by way of limitation of the scope of the invention.

6. EXAMPLES

The results provided herein demonstrate that an extracellular portion of CA 125/O772P remains in cell-associated form after a portion of the CA 125/O772P polypeptide is released as shed CA 125/O772P. In particular, the presence of cell-associated CA 125/O772P is demonstrated via the successful generation and characterization of several antibodies that preferentially bind the cell-associated CA 125/O772P species relative to the shed CA 125/O772P species. In addition to preferential binding, the results presented herein describe antibodies that exhibit a high degree of specificity for CA 125/O772P and affinity for the cell-associated CA 125/O772P antigen. Still further, the results presented herein demonstrate that such antibodies can function to mediate lysis of CA 125/O772P-positive tumor cells.

6.1. Antibody Generation

The experiments provided herein describe the generation of monoclonal antibodies against an extracellular portion of CA 125/O772P. As demonstrated in subsequent subsections, antibodies generated via such techniques include ones that are specific for CA 125/O772P, preferentially bind cell-associated CA 125/O772P, exhibit a high degree of affinity for cell-associated CA 125/O772P, and can function to mediate lysis of CA 125/O772P-positive tumor cells.

Antigen and Antigen-Expressing Constructs:

Expression constructs were generated for expressing CA 125/O772P antigen for use in antibody production. The first antigen, designated O772P 3-repeat (FIG. 1; SEQ ID NO:1), to be expressed included the carboxyl-most three tandem repeats of the extracellular domain of CA 125/O772P, up to, but not including, the CA 125/O772P transmembrane sequence. The second antigen, designated O772P 3-repeat TM (FIG. 2; SEQ ID NO:2), to be expressed included the carboxyl-most three tandem repeats of the extracellular domain of CA 125/O772P as well as the transmembrane and cytoplasmic sequence depicted in FIG. 2. In particular, sequences encoding each of the antigens were subcloned into pSecTag2B vectors (Invitrogen). The vector encodes an Ig kappa signal sequence for secretion and myc and 6×his tags for detection and purification of expressed protein.

Antigen Expression:

Recombinant antigen was produced by transiently transfecting suspension CHO-K1 cells with the constructs described above. Media used for the transfection was ProCHO CDM (BioWhittaker Inc. Walkersville, Md.) with GS supplements (JRH Biosciences Lenexa, Kans.). To produce a liter of material, 2 mg of the transfection reagent Clonfection™ (Clontech, Palo Alto, Calif.) was rehydrated, diluted into 24 ml of transfection media and incubated 15 minutes with 125 µg of DNA in the same media. The transfection mixture was added to 450 ml of transfection media containing $1.25 \times 10^9$ suspension CHO-K1 cells and incubated 4 hours at 37° C. on an orbital shaker. Following the incubation, 500 ml of ProCHO 4-CDM with GS supplements, penicillin-streptomycin and 10% ultra low IgG FBS (Life Technologies Rockville, Md.) was added to the transfected cells and the culture was transferred into roller bottles. Samples were collected on day 3 and cultures were harvested on day 7.

Antigen Purification:

Transfection supernatant was concentrated to 250 ml using a Millipore Pellicon system with a 50K cut-off membrane. 2 ml Talon resin (Clontech, Palo Alto, Calif.), obtained from the TALON Purification kit (cat #K1253-1), was transferred to a 2 ml column and was washed with 20 ml 1× wash/extraction buffer (supplied with the kit, pH 7.0). Concentrated sample was then loaded onto the column at a flow rate of 1 mL/min. The column was then washed with 15 ml extraction/wash buffer. Bound protein was then eluted with 4×1 ml elution buffer (50 mM Na Phosphate, 300 mM NaCl, 150 mM imidizole, pH 7.0). One-half ml fractions were collected and analyzed by SDS-PAGE and visualized using Coomassie Brilliant Blue G-250. Fractions containing O772P 3-repeat recombinant protein were further purified by Con-A Sepharose chromatography. One ml Con A Sepharose (Vector Laboratories, Inc., cat # AC-1003, lot # K0425) was transferred to a 15 ml conical centrifuge tube and washed with 10 ml 1× phosphate-buffered saline (PBS), pH 7.2. Wash buffer was removed by centrifugation. Fractions from TALON purification containing O772P 3-repeat protein were diluted 1:1 with 1×PBS, pH 7.2 and added to the washed ConA Sepharose and rotated overnight at 4° C. The resin slurry was then transferred to a 5 ml gravity-flow column and washed with 10 ml 1×PBS, pH 7.2. Samples were eluted with 0.6M methyl a-D-mannopyranoside in 1×PBS, pH 7.2 in 0.5 ml fractions in a total volume of 6 ml. Fractions were analyzed by SDS-PAGE and visualized using Coomassie Brilliant Blue G-250. Fractions containing pure O772P 3-repeat protein were combined and dialyzed against 2 L 1×PBS, pH 7.2 and stored at 4° C.

Immunization:

BALB/c mice were immunized intraperitoneally (i.p.) on Days 0, 21, 42, and 63. The first injection was with NIH:OVCAR-3 (ATCC HTB-161) cells and subsequent injections were with O772P 3-repeat protein without a transmembrane domain. Complete Freund's adjuvant was used for the first protein injection and incomplete Freund's adjuvant was used for the remaining injections. Serum was collected on days 35, 56, and 77 and analyzed by ELISA and flow cytometry as described below. Mice with the best serum titers were selected for cell fusion. On day one and two prior to fusion, the selected mice were boosted with mammalian expressed O772P 3-repeat protein i.p. and intravenously (i.v.). The day before the fusion the mice were boosted i.v.

Hybridoma Production:

The mouse spleen was removed and spleen cells were harvested by mincing with forceps and straining the cells through a sieve. Cells were washed twice in IMDM medium and cell counts were performed. P3X63Ag8.653 mouse myeloma cells (ATCC CRL-1580) in log phase growth were harvested, washed twice in IMDM medium and cells were counted. Spleen cells and myeloma cells were mixed together in a ratio of 5:1 and centrifuged at 200×g for 5 minutes. After aspiration, the pellet was loosened by tapping the bottom of the tube. One ml of a 50% solution of PEG (m.w. 1450) was added drop by drop over a period of 30 seconds and then the pellet was mixed gently for 30 seconds using a pipette. The resulting suspension was allowed to stand undisturbed for another 30 seconds. Five ml of IMDM were added over a period of 90 seconds followed by another 5 ml immediately. The resulting cell suspension was left undisturbed for 5 minutes. Following centrifugation, the cells were resuspended in HAT medium (IMDM containing 10% FBS, 2 mM L-glutamine, 0.6% 2-mercaptoethanol (0.04% solution), hypoxanthine, aminopterin, thymidine, and 10% ORIGENO Hybridoma Cloning Factor (IGEN International, Gaithersburg, Md.)) to a concentration of $5 \times 10^5$ cells per ml and plated at 0.2 ml or $1 \times 10^5$ cells per well into 96 well plates. Plates were incubated at 37° C. in a 7% $CO_2$ atmosphere with 100% humidity. Seven days after fusion, the media was removed and replaced with IMDM containing 10% FBS, 2 mM L-glutamine, 0.6% 2-mercaptoethanol stock (0.04%), hypoxanthine and thymidine. Ten to fourteen days after fusion, the supernatant was taken from wells with growing hybridoma colonies and tested for binding to CA 125/O772P as discussed herein.

Purification of Antibodies from Hybridoma Supernatants:

One-half ml protein G resin (Sigma, St. Louis, Mo.) was packed into a 5 ml disposable column (Bio-Rad, Hercules, Calif.). The column was pre-equilibrated with 20 ml binding buffer (20 mM PBS, pH 7.0). The hybridoma supernatant was loaded onto the column at a flow rate less than 0.5 ml/min. The column was then washed with 20 ml binding buffer at a flow rate of 1 ml/min. Alternatively, prepacked Protein G columns were used (Amersham Pharmacia Biotech). The antibody was then eluted with 3 ml elution buffer (0.1 M glycine, pH 2.7). 0.5 ml fractions were collected into 1 ml tubes containing 50 µl 1 M Tris, pH 9.0. Samples were dialyzed against PBS (0.5 L) and concentrated to approximately 1 mg/ml protein.

Antibody Concentrations in Hybridoma Supernatants:

Concentrations of antibody were determined using EasyTiter Mouse IgG Assay Kit. (Pierce Biotechnology, Rockford, Ill.). Briefly, Mouse IgG whole molecule standard (Pierce Biotechnology, Rockford, Ill.) was diluted to 500 ng/ml in dilution buffer (supplied with the kit). This standard was serially diluted 1:2 six times in dilution buffer to generate a standard curve. Twenty µl of each standard was added to corresponding wells in a 96-well plate. Dilutions of hybridoma supernatant (20 µl) were also added to the plate. Duplicate wells were done for each standard and sample. Twenty µl of polystyrene beads (supplied with the kit) were added to each well, the samples were mixed, the plate was sealed, and was incubated on a plate shaker for 5 minutes at room temperature. 100 µl of Blocking reagent from the kit was then added to each well. The plate was again shaken for 5 minutes at room temperature. The absorbance was then read at 405 nm on a Vmax plate reader (Molecular Devices Corp., Sunnyvale, Calif.) and a 4 parameter fit was used to generate the standard curve.

6.2. CA 125/O772P Specificity

The results presented herein demonstrate that antibody production via the techniques described above resulted in generation of antibodies specific for CA 125/O772P.

ELISA Specificity Assay

Methods:

Ninety-six well plates were incubated and coated with 100 µl (per well) of 1 µg/ml O772P 3-repeat protein (SEQ ID NO:1) (affinity-purified) in bicarbonate buffer (0.2 M $Na_2CO_3/NaHCO_3$, pH 9.6, Sigma) overnight at 4° C. On the next day, the plates were washed with 200 µl 1×PBST (1× phosphate-buffered saline (PBS), 0.05% Tween 20) three times and blocked with 100 µl of 1×PBST containing 1% bovine serum albumin (BSA) for 2 hours at 37° C. After washing the plates with 1×PBST three times, murine anti-CA 125/O772P selected hybridoma-produced antibodies (0.04 mg/µl) were added to the plates (individual wells). After 1 hour incubation at 37° C., the plates were then washed with 1×PBST three times. For signal detection, 100 µl of HRP (horseradish peroxidase)-conjugated sheep anti-mouse IgG (1:2000 dilution into 1×PBST+1% BSA; Amersham Biosciences) was added to each well and incubated for 1 hour at 37° C. The plates were again washed three times with 1×PBST. Finally, 100 µl of a mixture of TMB (3,3',5,5'-tetramethylbenzidine) substrate and $H_2O_2$ (1:1 ratio, KPL Kirkguard Perry Laboratories) was added into each well and after a 5 minute incubation, the absorbance was measured at 405 nm with a plate reader (Molecular Devices Corp., Sunnyvale, Calif.). The assay was done in triplicate for each selected O772P hybridoma-produced antibody and data was collected and analyzed as a kinetic assay, measured over a 5 minute time period. Average values were calculated and presented. Controls for blank and individual reagents were also included in each experiment.

Results:

Table 7, below, presents the ELISA Specificity Assay results for four selected anti-CA 125/O772P hybridoma-produced antibodies (117.1, 368.1, 501.1, 776.1). The table also shows the ELISA Specificity Assay results for two commercially available CA 125/O772P antibodies (OC125 and M11, Dako Corp., Carpinteria, Calif.). An antibody (or antigen-binding antibody fragment) is considered positive in this assay (i.e., is specific for CA 125/O772P) if it exhibits an absorbance of at least 5 to greater than 30 OD/microgram antibody. These results demonstrate that each of the tested antibodies is specific for CA 125/O772P. It is noted, as demonstrated, below, that, although OC125 and M11 are considered specific for CA 125/O772P, neither antibody preferentially binds cell-associated CA 125/O772P relative to shed CA 125/O772P. SD=standard deviation.

TABLE 7

| Ab name | absorbance (OD) | SD | absorbance (OD)/µg Ab |
|---|---|---|---|
| OC 125 | 0.73 | 0.003 | 18 |
| M11 | 0.974 | 0.008 | 24 |
| 117.1 | 0.619 | 0.033 | 15 |
| 368.1 | 1.293 | 0.004 | 32 |
| 501.1 | 0.856 | 0.005 | 21 |
| 776.1 | 1.178 | 0.043 | 29 |

The results in Table 8, below, show absorbance data for twenty additional antibodies generated using the techniques described above. As shown by the absorbance data, each of these antibodies is also specific for CA 125/O772P.

TABLE 8

| Ab name | absorbance (OD)/µg Ab |
|---|---|
| 325.1 | 24 |
| 446.1 | 27 |
| 621.1 | 27 |
| 633.1 | 18 |
| 654.1 | 22 |
| 725.1 | 25 |
| 8G9 | 22 |
| 7F10 | 19 |
| 8A1 | 18 |
| 8C3 | 23 |
| 15C9 | 28 |
| 8E3 | 18 |
| 8B5 | 18 |
| 7G10 | 20 |
| 16C7 | 22 |
| 7C6 | 23 |
| 7H1 | 26 |
| 16H9 | 22 |
| 7A11 | 22 |
| 4E7 | 19 |

Flow Cytometry Specificity Assay:
Method:

Cells (OVCAR-3 (ATCC Accession No. HTB-161), SK-OV3 (ATCC Accession No. HTB-77), NIH/3T3 (ATCC Accession No. CRL-1658), and NIH/3T3 cells transfected with a sequence that expresses O772P 3-repeat protein (SEQ ID NO:2)) were removed from culture plates by digestion with trypsin (0.25%). The cells were counted and viability was assessed by trypan blue (0.2%) exclusion. Cells were then centrifuged (500×g, 5 min) and resuspended in FACS buffer (1×DPBS containing 1% BSA and 0.1% sodium azide) to a concentration between 5-10×10$^7$ cells/ml. Cells were then distributed at a volume of 100 µl/well into 96-well round bottom plates and centrifuged at 500×g for 3 minutes. Antibody supernatant was removed by aspiration, and 50 µl hybridoma supernatants diluted to 1 µg/ml and 0.5 µg/µl in FACS buffer and was added to each well containing cells. Murine IgG1 kappa (Sigma, St. Louis, Mo.) (either 2.0, 1.0, 0.5, 0.1 µg/µl) was included as a negative control and OC125 and M11 (DAKO Corp, Carpinteria, Calif.) were included as positive controls. Plates were incubated for 30 minutes at 4° C. with rocking. Cells were subsequently washed 2 times with FACS buffer (200 µl/well), with centrifugation and buffer aspiration following each wash. Goat anti-mouse IgG (Fc)-biotin (Sigma, St. Louis, Mo.) was diluted 1:1000 in FACS buffer and 50 µl was added to each well containing cells. Plates were incubated 30 minutes at 4° C. with rocking. Cells were then washed with FACS buffer as above. Streptavidin-Alexa-Four 488 (Molecular Probes, Eugene, Oreg.) was diluted 1:1000 into FACS buffer and 50 µl was added to each well containing cells. Plates were then incubated 30 minutes at 4° C. with washing. Cells were then washed with FACS buffer, as above. Cells were then resuspended in 1 ml of FACS buffer and transferred to Falcon 2052 tubes and analyzed on a Becton-Dickinson Immunocytometry Systems FACSCalibur flow cytometer (San Jose, Calif.).

Results:

Table 9, below, presents the Flow Cytometry Specificity Assay results from four selected anti-CA 125/O772P hybridoma-produced antibodies (117.1, 368.1, 501.1, 776.1). The table also shows the Flow Cytometry Specificity Assay results for the commercially available OC125 and M11. The NIH/3T3 cells and the SK-OV3 cells (an ovarian cancer cell line) were considered negative controls because neither produces CA 125/O772P.

Antibodies (or antigen-binding antibody fragments) are considered positive (that is, are specific for CA 125/O772P) if they exhibit a Flow Cytometry Specificity Assay result within the following positive cell ranges: less than about 5% positive NIH/3T3 cells, and at least about 60% positive NIH/3T3 cells producing a SEQ ID NO:2 polypeptide; or less than about 25% positive SK-OV3 cells and at least about 80% positive OVCAR-3 cells. (nd—not determined)

These results demonstrate that each of the tested antibodies is specific for CA 125/O772P. It is noted, as demonstrated, below, that, although OC125 and M11 are considered specific for CA 125/O772P, neither of these two antibodies preferentially binds cell-associated CA 125/O772P relative to shed CA 125/O772P.

TABLE 9

| Antibody | % positive - NIH/3T3 O772P 3-repeat | % positive - NIH/3T3 | % positive - OVCAR-3 | % positive - SK-OV3 |
|---|---|---|---|---|
| OC 125 (1 µg/ml) | nd | nd | 98 | 16 |
| OC 125 (0.1 µg/ml) | nd | nd | 85 | 10 |
| M11 (1 µg/ml) | 84 | 0.1 | 98 | 17 |
| M11 (0.1 µg/ml) | nd | nd | 91 | 11 |
| 117.1 (2 µg/ml) | 83 | 0.1 | 93 | 6 |
| 117.1 (0.5 µg/ml) | 63 | 0 | nd | nd |
| 368.1 (2 µg/ml) | 86 | 0.2 | 89 | 5 |
| 368.1 (0.5 µg/ml) | 75 | 0.2 | nd | nd |
| 501.1 (2 µg/ml) | 89 | 0 | 95 | 5 |
| 501.1 (0.5 µg/ml) | 85 | 0.2 | nd | nd |
| 776.1 (2 µg/ml) | 86 | 0 | 94 | 9 |
| 776.1 (0.5 mg/ml) | 84 | 0 | nd | nd |

The results provided in Table 10, below, present OVCAR-3/SK-OV3 data for twenty additional antibodies generated as described above demonstrating that these antibodies, too, are specific for CA 125/O772P.

TABLE 10

| Ab name | % positive OVCAR-3 (0.5 µg/ml) | % positive SK-OV3 (2.0 µg.ml) |
|---|---|---|
| 325.1 | 98 | 6 |
| 446.1 | 94 | 5 |
| 621.1 | 97 | 9 |
| 633.1 | 89 | 9 |
| 654.1 | 86 | 8 |
| 725.1 | 96 | 10 |
| 8G9 | 97 | 4 |
| 7F10 | 96 | 3 |
| 8A1 | 97 | 3 |
| 8C3 | 97 | 3 |
| 15C9 | 95 | 3 |
| 8E3 | 95 | 1 |
| 8B5 | 94 | 1 |
| 7G10 | 96 | 2 |
| 16C7 | 96 | 3 |
| 7C6 | 96 | 3 |
| 7H1 | 96 | 0 |
| 16H9 | 96 | 3 |
| 7A11 | 94 | 1 |
| 4E7 | 97 | 2 |

6.3. Competition Assays Demonstrate the Successful Production of Antibodies that Preferentially Bind CA 125/O772P The results presented herein demonstrate that antibodies produced via the techniques described above can generate antibodies that preferentially bind cell-associated CA 125/O772P relative to shed CA 125/O772P. The fact that such antibodies can be generated also demonstrates, for the first time, that cell-associated CA 125/O772P polypeptides exist, i.e., that an extracellular portion of CA 125/O772P remains in cell-associated form, however transiently, after a portion of the CA 125/O772P polypeptide is released as shed CA 125/O772P.

ELISA Competition Assay:
Method:
Ninety-six well plates were coated with 100 µl (per well) of 1 µg/ml O772P 3-repeat (SEQ ID NO:1) polypeptide (affinity-purified) in bicarbonate buffer (0.2 M $Na_2CO_3$/$NaHCO_3$, pH 9.6, Sigma) overnight at 4° C. On the next day, the plates were washed with 200 µl 1xPBST (1x phosphate-buffered saline (PBS), 0.05% Tween 20) three times and blocked with 100 µl of 1xPBST containing 1% bovine serum albumin (BSA) for 2 hours at 37° C. After washing with 1xPBST three times, selected anti-CA 125/O772P hybridoma-produced antibodies at indicated concentrations (e.g., 0.04 µg/ml) were added to wells that had been pre-incubated for 20-30 minutes with excess amounts (e.g., 10-50 fold w/w) of shed CA 125/O772P (Fitzgerald Industries International, Concord, Mass.; Scripps Laboratories, La Jolla, Calif.; and/or United States Biological Corp.). After 1 hour incubation at 37° C., the plates were then washed with 1xPBST three times. For signal detection, 100 µl of HRP-conjugated sheep anti-mouse IgG (1:2000 dilution into 1xPBST+1% BSA, Amersham Biosciences) was added to each well and incubated for 1 hour at 37° C. The plates were washed again with 1xPBST three times. Finally, 100 µl of a mixture of TMB substrate and $H_2O_2$ (1:1 ratio, KPL) was added into each well and the absorbance was measured at 405 nm with a plate reader (Molecular Devices Corp., Sunnyvale, Calif.). The assay was done in triplicate for each selected antibody and average values were calculated and presented. The percent inhibition compared to no competition was calculated for individual antibodies based on average values. Controls for blank and individual reagents were also included in each experiment.

Results:
Table 11, below, presents the ELISA Competition Assay results for four selected anti-CA 125/O772P hybridoma-produced antibodies (117.1, 368.1, 501.1, 776.1). The table also shows the ELISA Competition Assay results for the commercially available CA 125/O772P antibody (OC125; DAKO Corp., Carpenteria, Calif.). An antibody (or antigen-binding antibody fragment) is considered positive in this assay (that is, preferentially binds cell-associated CA 125/O772P) if it exhibits less than about 25% inhibition of binding at 25-fold (w/w) excess shed CA 125/O772P. These results demonstrate that each of antibodies 117.1, 368.1, 501.1 and 776.1 preferentially binds cell-associated CA 125/O772P. These results also demonstrate that OC125 antibody fails to preferentially bind cell-associated CA 125/O772P. (SD-standard deviation)

TABLE 11

| antibody | absorbance | SD | absorbance w/ shed CA 125/O772P competitor (25-fold w/w excess) | SD | percent inhibition of binding | absorbance w/ O772P 3-repeat competitor (10x w/w excess) | SD | percent inhibition of binding |
|---|---|---|---|---|---|---|---|---|
| OC 125 | 0.73 | 0.003 | 0.074 | 0.001 | 95 | 0.047 | 0.002 | 99 |
| 117.1 | 0.619 | 0.033 | 0.554 | 0.007 | 11 | 0.071 | 0.001 | 94 |
| 368.1 | 1.293 | 0.004 | 1.333 | 0.009 | 0 | 0.915 | 0.016 | 30 |
| 501.1 | 0.856 | 0.005 | 0.735 | 0.008 | 15 | 0.065 | 0.002 | 96 |
| 776.1 | 1.178 | 0.043 | 0.977 | 0.01 | 17 | 0.077 | 0.001 | 96 |

The results presented in Table 12, below, present CA 125/O772P competitor data for twenty additional antibodies generated via the techniques described above demonstrating that these antibodies, too, represent antibodies that preferentially bind cell-associated CA 125/O772P.

TABLE 12

| Ab name | % inh. binding w/shed CA 125/O772 competitor (25-fold excess)) |
|---|---|
| 325.1 | 2 |
| 446.1 | 7 |
| 621.1 | 2 |
| 633.1 | 7 |
| 654.1 | 9 |
| 725.1 | 7 |
| 8G9 | 7 |
| 7F10 | 6 |
| 8A1 | 8 |
| 8C3 | 5 |
| 15C9 | 5 |
| 8E3 | 4 |
| 8B5 | 6 |
| 7G10 | 3 |
| 16C7 | 3 |
| 7C6 | 2 |
| 7H1 | 4 |
| 16H9 | 0 |
| 7A11 | 5 |
| 4E7 | 7 |

Flow Cytometry Competition Assay:
Method:

NIH:OVCAR-3 (ATCC Accession No. HTB-161) cells were removed from culture plates by digestion with trypsin (0.25%). Cells were then counted and viability was assessed by trypan blue (0.2%) exclusion. Cells were then centrifuged (500×g, 5 min) and resuspended in FACS buffer (1×DPBS containing 1% BSA and 0.1% sodium azide) to a concentration between 5-10×10$^7$ cells/ml. Cells were then distributed (100 µl/well) into 96-well round bottom plates and centrifuged 500×g for 3 minutes. Supernatants were removed by aspiration. Hybridoma supernatants were diluted to 0.2 µg/ml of antibody in FACS buffer. CA 125 (Fizgerald Industries International, Concord, Mass.) was diluted to 1000 µg/ml, 500 µg/ml, 200 µg/ml, 60 µg/ml, 20 µg/ml, 6 µg/ml, or 2 µg/ml in FACS buffer. Thirty antibody solution was incubated with 30 µl diluted CA 125 or buffer alone for 30 minutes at 4° C. 50 µl of the mixture was added to each well containing cells. Murine IgG1 kappa (Sigma, St. Louis Mo.) and M11 (DAKO Corp, Carpinteria, Calif.) were included as negative and positive controls, respectively. Plates were incubated for 30 minutes at 4° C. with rocking. Cells were subsequently washed 2 times with FACS buffer (200 µl/well), with centrifugation and aspiration of buffer following each wash. Goat anti-mouse IgG (Fc)-biotin (Sigma, St. Louis, Mo.) was diluted 1:1000 in FACS buffer and 50 µl was added to each well containing cells. Plates were incubated 30 min at 4° C. with rocking. Cells were then washed with FACS buffer as above. Streptavidin-Alexa-Four 488 (Molecular Probes, Eugene, Oreg.) was diluted 1:1000 into FACS buffer and 50 µl was added to each well containing cells. Plates were then incubated 30 minutes at 4° C. with washing. Cells were then washed with FACS buffer, as above. Cells were then resuspended in 1 ml of FACS buffer and transferred to Falcon 2052 tubes and analyzed on a Becton-Dickinson Immunocytometry Systems FACSCalibur flow cytometer (San Jose, Calif.). Percent positive cells was plotted as a function of CA 125/O772P concentration using GraphPad plotting software. IC$_{50}$ determinations, expressed as the concentration of shed CA 125/O772P at which 50% inhibition of binding is seen, were made using a linear regression analysis.

Results:

FIG. 3 shows a representative plot of shed CA 125/O772P concentration versus percent positive cells for, in this instance, 117.1 antibody and M11 antibody control (squares).

Table 13, below, presents a summary of Flow Cytometry Competition Assay results. An antibody (or antigen-binding antibody fragment) is considered positive (that is, is considered to preferentially bind cell-associated CA 125/O772P) if it exhibits an IC$_{50}$, as measured by percent-positive cells, of at least about 0.05 mg/ml shed CA 125/O772P.

The results shown in Table 13, below, demonstrate that each of 117.1, 501.1, 776.1, 8C3, 16H9, 325.1, 633.1 and 725.1 antibodies preferentially binds cell-associated CA 125/O772P. It is noted that the results in Table 13 also demonstrate that the OC125 and M11 antibodies do not preferentially bind cell-associated CA 125/O772P.

TABLE 13

| antibody | IC$_{50}$ (mg/ml CA 125) function of % positive cells |
|---|---|
| OC 125 | 0.005 |
| M11 | 0.01 |
| 117.1 | >1.0 |
| 368.1 | nd |

TABLE 13-continued

| antibody | IC$_{50}$ (mg/ml CA 125) function of % positive cells |
|---|---|
| 501.1 | 0.13 |
| 776.1 | 0.19 |
| 8C3 | >0.5 |
| 16H9 | >0.5 |
| 325.1 | 0.36 |
| 621.1 | >0.5 |
| 633.1 | 0.18 |
| 725.1 | 0.42 |
| 446.1 | nd |
| 654.1 | nd |
| 8G9 | nd |
| 7F10 | nd |
| 8A1 | nd |
| 15C9 | nd |
| 8E3 | nd |
| 8B5 | nd |
| 7G10 | nd |
| 16C7 | nd |
| 7C6 | nd |
| 7H1 | nd |
| 7A11 | nd |

6.4. Affinity Assay

The results presented herein demonstrate that among the antibodies generated that preferentially bind CA 125/O772P, are antibodies that exhibit a high degree of affinity for cell-associated CA 125/O772P.

BIAcore Affinity Assay: Methods:

A GM5 BIAcore biosensor chip was docked into the BIAcore X instrument and activated with 55 µl of 1:1 NHS/EDC at room temperature. O772P 3-repeat region protein and BSA at 10 µg/ml in 0.05 M acetate buffer, pH 4.5, were immobilized onto the flow cell (FC) 1 and FC2 of the activated chip, respectively, at a flow rate of 5 µl/min to achieve a resonance response of 1000-2000 RU. The chip was then blocked by injection of 55 µl of ethanolamine-HCl, pH 8.5, and followed with washing 5 times with 50 mM NaOH-1M NaCl. To measure the binding of anti-O722P mAbs to the O772P 3-repeat region immobilized to the chip, 30 µl of anti-O722P mAbs at varying concentrations in BIAcore running buffer (HBS-EP, Cat. #1001-080, BIAcore, Piscataway, N.J.) were injected over the sensor surface at a flow rate of 5 µl/min. Following completion of the injection phase, dissociation was monitored in BIAcore running buffer at the same flow rate for 360 seconds. The surface was regenerated between injections using 30 µl of 50 mM NaOH-1M NaCl. Individual sensorgrams were analyzed using BIAevaluation.

BIAcore Affinity Assay: Results:

Table 14, below, presents a summary of BIAcore Affinity Assay results for 117.1, 368.1, 501.1 and 776.1 antibodies, as well as for M11 and OC125 antibodies. As shown in the table, each of antibodies 117.1, 368.1, 501.1, 776.1, 4E7, 7C6, 7F10, 7G10, 7H1, 8A1, 8B5, 8C3, 8E3, 15C9, 16C7, 16H9, 325.1, 621.1, 633.1 and 725.1 bind with high affinity to CA 125/O772P polypeptide.

TABLE 14

| antibody | K$_d$(nM) |
|---|---|
| M11 | 1.6 |
| OC125 | 4 |
| 117.1 | 12 |
| 368.1 | 0.7 |
| 501.1 | 70 |
| 776.1 | 0.4 |
| 4E7 | 30 |

TABLE 14-continued

| antibody | $K_d$(nM) |
|---|---|
| 7A11 | nd |
| 7C6 | 73 |
| 7F10 | 3.7 |
| 7G10 | 47 |
| 7H1 | 69 |
| 8A1 | 2.8 |
| 8B5 | 32 |
| 8C3 | 5.0 |
| 8E3 | 33 |
| 8G9 | 14 |
| 15C9 | 14 |
| 16C7 | 44 |
| 16H9 | 3.9 |
| 325.1 | 15 |
| 446.1 | nd |
| 621.1 | 40 |
| 633.1 | 26 |
| 654.1 | 190 |
| 725.1 | 2.6 |

6.5. Functional Assays:

The results presented herein demonstrate that among the antibodies generated that preferentially bind cell-associated CA 125/O772P are antibodies that can function to mediate lysis of CA 125/O772P-positive tumor cells.

ADCC Assay;
Method:

Human leukocytes were isolated from peripheral blood of normal donors by a Histopaque-1077 gradient centrifugation procedure (Sigma Co., St. Louis, Mo.) and used as effector cells. In U-bottom, 96-well plates, OVCAR-3 target cells ($5\times10^3$/well) were mixed with Histopaque-purified human leukocytes at effector-to-target (I:T) ratios of 12.5:1 to 50:1 in the absence or presence of varying concentrations of monoclonal antibodies in a total volume of 120 μl of RPMI 1640 supplemented with 10% FBS. The plates were incubated at 37° C. in a humidified 5% $CO_2$ atmosphere. Target cells and effector cells without the testing antibody were used as negative controls. Following 16-18 hr. incubation, 50 μl aliquots of culture supernatant were collected and assayed for lactate dehydrogenase activity in flat-bottom, 96-well plates using the Cytotox 96 Non-radioactive Cytotoxicity Assay Kit (Promega Co., Madison, Wis.) according to manufacturer's instructions. Percent lysis of tumor cells was calculated as follows: % Cytotoxicity=(experimental release−effector spontaneous release−target spontaneous release)/(target maximum release−target spontaneous release)×100. The results were expressed as mean percentage lysis ±S.D. of replicate samples.

Results:

FIG. 4 shows a representative plot of percent lysis versus antibody concentration for 117.1 antibody (average of 4 separate donors). As shown in the figure, 117.1 antibody mediates lysis of OVCAR-3 ovarian cancer cells in a dose-dependant manner CDC Assay:

In U-bottom, 96-well plates, OVCAR-3 target cells ($2\times10^4$/well) are mixed with human or guinea pig complement diluted 15:1, 20:1, 25:1 in the absence or presence of varying concentrations of antibody in a total volume of 120 μl of RPMI 1640 supplemented with 10% FBS. The plates are incubated at 37° C. in a humidified 5% $CO_2$ atmosphere. Target cells without antibody are used as negative controls. Following 4 hr. incubation, 50 μl aliquots of culture supernatant are collected and assayed for lactate deyhdrogenase activity in flat-bottom, 96-well plates using the Cytotox 96 Non-radioactive Cytotoxicity Assay Kit (Promega Co., Madison, Wis.) according to the manufacturer's instructions. Percentage lysis of tumor cells is calculated as follows: % Cytotoxicity=(experimental release−effector spontaneous release−target spontaneous release)/(target maximum release−target spontaneous release)×100. Results are expressed as mean percentage lysis ±S.D. of replicate samples.

6.6. Sequences of Antibodies that Preferentially Bind Cell-Associated CA 125/O772P The results presented herein provide the amino acid and nucleotide sequences for the variable regions of six of the monoclonal antibodies described herein: 117.1, 368.1, 501.1, 776.1, 725.1 and 16H9, including CDR sequences.

Methods:

Hybridoma cells were harvested and pelleted at 1800 rpm for 10 minutes at 4° C. One ml of TRIzol (Invitrogen) was added per $10^7$ cells and total RNA was processed. Two hundred μl of chloroform per 1 ml of TRIzol Reagent was added, shaken vigorously by hand for 15 sec. and centrifuged at 12,000×g for 15 minutes at 4° C. The aqueous phase containing the RNA was transferred to a fresh tube and precipitated by adding 500 μl of isopropyl alcohol per 1 ml of TRIzol Reagent used for the initial homogenization. The RNA pellet was washed once with 70% EtOH and briefly air-dried before being resuspended in DEPC water. Three μg of total RNA were treated with 10 units of calf intestinal phosphatase (CIP) for 1 hour at 50° C. to remove the 5' phosphates. This step eliminated truncated mRNA and non-mRNA from subsequent steps. Dephosphorylated RNA was treated with 0.5 units of tobacco acid pyrophosphatase (TAP) for 1 hour at 37° C. to remove the 5' cap structure from intact, full length mRNA. The GeneRacer RNA Oligo (5'-CGACUGGAG-CACGAGGACACUGACAUGGACUGAAG-GAGUAGAAA-3'; SEQ ID NO:43) was ligated to the 5' end of the mRNA using 5 units of T4 RNA Ligase for 1 hour at 37° C. The ligated mRNA was reverse-transcribed using 5 units of AMV-Reverse Transcriptase and the GeneRacer Oligo dT Primer (5'-GCTGTCAACGATACGCTACGTAACG-GCATGACAGTG(T)$_{18}$-3'; SEQ ID NO:44) for 1 hour at 42° C. to create cDNA with known priming sites at the 5' and 3' ends. The 5' ends were amplified using a gene-specific 3' primer located in the constant region of the desired gene (heavy chain 5'-AYCTCCACACACAGGRRCCAGTG-GATAGAC (SEQ ID NO:45), light chain 5'-GGATACAGT-TGGTGCAGCATC-3' (SEQ ID NO:46)) and the GeneRacer 5' Primer homologous to the GeneRacer RNA Oligo (5'-CGACTGGAGCACGAGGACACTGA-3'; SEQ NO:47). The PCR reaction was carried out using 2 μl of cDNA by denaturing the template at 94° C. for 5 min. and then denaturing at 94° C. for 30 sec., annealing at 55° C. for 30 sec., elongating at 72° C. for 1 minute for 30 cycles and elongating for a final cycle at 72° C. for 7 min. on a GeneAmp 9700 PCR System. Bands of interest were gel purified using the Qiagen Gel Purification Kit and cloned using the TOPO-4 Cloning Kit (Invitrogen). Resultant isolated colonies were screened by PCR for insert of the correct size in a GeneAmp 9700 machine. PCR was performed by lysing the bacteria at 94° C. for 8 min, then denaturing at 94° C. for 30 sec., annealing at 55° C. for 30 sec., elongating at 72° C. for 1-4 minutes for 25 cycles and elongating for a final cycle at 72° C. for 7 min. Primers used for screening were: sense, 5'-ATTAACCCT-CACTAAAGGGA-3' (SEQ ID NO:48) or 5'-TAATAC-GACTCACTATAGGG-3' (SEQ ID NO:49), antisense heavy or light chain constant region primers (see above). Positive clones were grown in a 4 ml overnight culture to amplify the clone and a SNAP Miniprep (Invitrogen) was performed.

Clones were then sequenced using the BigDye (Perkin Elmer) chemistry in a GeneAmp 9700 PCR System for 25 cycles by denaturing the DNA for 10 sec, at 94° C., annealing the primer (5'-ATTAACCCTCACTAAAGGGA-3' (SEQ ID NO:50) or 5% TAATACGACTCACTATAGGG-3' (SEQ ID NO:51)) at 50° C. for 5 sec. and elongating the primer for 4 min. at 72° C. The reactions were then passed over a DyeEx Column (Qiagen) and sequenced on an Applied Biosystems 310 automated DNA sequencer.

Results:

Nucleic acid sequences that encode the variable regions of six monoclonal antibodies that preferentially bind cell-associated CA 125/O772P were obtained and are depicted in FIGS. 5-10. In particular, FIGS. 5A, 6A, 7A, 8A, 9A and 10A depict the nucleotide sequences that encode the variable light chain regions of monoclonal antibodies 117.1, 368.1, 501.1, 776.1, 725.1 and 16H9, respectively, while FIGS. 5B, 6B, 7B, 8B, 9B and 10B depict the nucleotide sequences that encode the variable heavy chain regions of monoclonal antibodies 117.1, 368.1, 501.1, 776.1, 725.1 and 16H9, respectively. The nucleotide sequences that encode leader sequences are double underlined, and the nucleotide sequences that encode CDR sequences are underlined.

Amino acid sequences of the variable regions of six monoclonal antibodies that preferentially bind cell-associated CA 125/O772P were obtained and are depicted in FIGS. 5-10. In particular, FIGS. 5C, 6C, 7C, 8C, 9C and 10C depict the amino acid sequences of the variable light chain regions of monoclonal antibodies 117.1, 368.1, 501.1, 776.1, 725.1 and 16H9, respectively, while FIGS. 5D, 6D, 7D, 8D, 9D and 10D depict the amino acid sequences of variable heavy chain regions of monoclonal antibodies 117.1, 368.1, 501.1, 776.1, 725.1 and 16H9, respectively. Leader sequences are double underlined, and CDR sequences are underlined. It is noted that the leader sequences do not become part of the mature antibodies, and, as such, are not considered a part of the variable regions of the antibodies.

6.7. Western Blot Analysis of OVCAR-3 Supernatents

The working example presented herein provides a western blot analysis designed to test directly the ability of antibodies 368.1 or 776.1 to bind shed CA 125/O772P. The data presented herein directly demonstrates that neither the 368.1 nor the 776.1 antibody recognize the high molecular weight species corresponding to shed CA 125/O772P. In contrast, antibodies OC 125 and M11 did recognize this high molecular weight species, while all of the antibodies tested bind strongly to the control 3-repeat-containing recombinant O772P polypeptide. Thus, these data provide additional confirmation that the 368.1 and the 776.1 antibodies preferentially bind cell-associated CA 125/O772P polypeptide.

Methods:

Media (RPMI supplemented with 10% fetal bovine serum) from cultured OVCAR-3 cells was removed and replaced with fresh supplemented media. Aliquots of conditioned media were removed at 1 hour, 6 hours, 24 hours, 48 hours and 72 hours. Supplemented media was used as the time 0 point A 4-12% Bis-Tris (Invitrogen) gel was loaded with 10 µl of conditioned media from each time point and separated by electrophoresis for 45 minutes at 200 volts. Purified O772P 3-repeat polypeptide was loaded as a positive control at 100 ng, 10 ng and 1.0 ng.

Proteins were transferred to a nitrocellulose membrane for one hour at 30 volts and then blocked overnight in non-fat milk at 4° C. Primary antibodies were brought to 400 µg/ml in PBS and then diluted 1:1000 in non-fat milk (OC125 Dako #M3519, M11 Dako #M3520). The blots were washed in PBS/Tween three times for 10 min. The secondary antibody (anti-mouse IgG Fc-specific, Sigma #B-7410) was diluted 1:1000 in non-fat milk and incubated for 1 hour at room temperature. Washes were performed as above. NeutraAvidin-HRP (Molecular Probes #A-2664) was diluted 1:1000 in PBS/Tween and incubated at room temperature for 15 minutes. The blots were washed in a large volume of PBS-Tween and visualized by chemiluminescence (30 sec. exposure).

Results:

To determine if 368.1 or 776.1 antibody binds to shed CA 125/O772P polypeptide, a western blot analysis was performed on the supernatant of cultured OVCAR-3 cells, which are known to shed CA 125/O772P from their surface. Such an analysis tests the antibodies' ability to bind shed CA 125/O772P directly.

As shown in FIG. 11, the results of the western analysis demonstrate that neither the 368.1 nor the 776.1 antibody recognize the high molecular weight species that corresponds to shed CA 125/O772P. In contrast, antibodies M11 and OC 125, that is, antibodies that do not preferentially bind cell-associated CA 125/O772P, did recognize this high molecular weight species. All four of the antibodies tested bind strongly to the control 3-repeat-containing recombinant O772P polypeptide, O772P 3-repeat, which contains extracellular domain sequences that are immediately adjacent to the CA 125/O772P transmembrane domain. Thus, these data provide additional confirmation that the 368.1 and the 776.1 antibodies preferentially bind cell-associated CA 125/O772P polypeptide.

6.8. Radiolabeled 776.1 Antibody Slows Tumor Growth

The results presented herein demonstrate that radiolabeled 776.1 antibody successfully slows tumor growth in an animal model for human ovarian cancer.

Methods:

Animals

Female NCr nu/nu ("nude") mice (Taconic Farms, Germantown, N.Y.) 6-7 weeks old were used for all studies. All animals were given food and water ad libitum.

Tumor Cell Implantation

For efficacy studies, the OVCAR-3 human ovarian carcinoma cell line was used for the model of human ovarian cancer. The OVCAR-3 cell line (Hamilton, et al., Cancer Res. 43:5379-5389 (1983)); was derived from an ovarian adenocarcinoma of human origin and was purchased from ATCC (Catalog #HTB-161). OVCAR-3 cells were maintained in RPMI-1640 supplemented with 10% FBS at 37° C. in 5% $CO_2$. OVCAR-3 expresses the tumor-associated CA 125/O772P on the cell surface. OVCAR-3 xenografts were subcutaneously implanted and grown as ectopic tumors in immune-deficient NCr nude mice. The major criterion for subcutaneous OVCAR-3 tumor growth was to achieve 150-250 mm³ tumors by two weeks post implantation, at which time experimental therapy would begin.

In order to facilitate subcutaneous tumor formation, the OVCAR-3 line was serially propagated in vivo within the peritoneal cavities of NCr nu/nu mice (Burbridge et al., Int. J. Oncol. 15: 1155-1162 (1999); Guichard et al., Clin. Cancer Res. 7: 3222-3228 (2001)). Prior to subcutaneous implantation, $10 \times 10^6$ in vitro cultured OVCAR-3 cells (passage 32) in 0.9% saline were injected i.p. into NCr nu/nu mice (passage 1). Seven weeks later tumor cells were harvested by peritoneal lavage and $5 \times 10^6$ cells were injected into a new set of recipients (passage 2). Four weeks later the cells were harvested by peritoneal lavage and passaged once more and $5 \times 10^6$ cells were injected into a new set of recipients (passage 3). After three weeks passage 3 cells were harvested and assayed for CA 125/O772P expression and viability.

For the radioimmunotherapeutic studies, passage 3 cells were implanted for subcutaneous tumor growth. Passage 3 cells were routinely >95% viable and retained high-levels of CA 125/O772P expression as confirmed by flow cytometry. For ectopic, solid tumor growth, cells were resuspended to a final concentration of $15 \times 10^6$ cells/ml in a mixture of Matrigel (Matrigel, BD Biosciences: Lot #005002, 14.6 mg/mL) and 0.9% saline with the final Matrigel concentration being 7.3 mg/mL. Mice were injected with 0.2 ml volume of the cell suspension for a final dose of $3 \times 10^6$ cells. The cell suspensions were injected subcutaneously on the ventral side of the abdominal area using a 23-gauge needle. The injection site was rendered aseptic by swabbing with sterile gauze in 70% ethanol. Approximately 10 days post-implantation palpable tumors were measured with electronic calipers (Fowler Instruments) across two perpendicular dimensions. Mice were sorted into groups of 10 based on tumor volume. For all groups within a study, there were no significant differences between mean tumor volumes. Tumor measurements and observation were recorded twice a week. Tumor volume was calculated using the standard formula (Length×Width)×0.5.

Coupling of 776.1 to $^{131}$Iodine

Murine IgG1 776.1 was iodinated at Perkin-Elmer by the modified IODO-GEN method (Visser et al., J. Nucl. Med. 42: 509-519 (2001)) which is an efficient means of coupling high doses of $^{131}$I to a monoclonal antibody while minimizing both chemical and radiation induced damage. Ten microliters of a 1.41 mg/ml solution of ascorbic acid pH 5.0 was added to 10 mCi of $^{131}$I and the mixture was incubated for one minute. This was followed by the addition of 100 µl of 0.5M phosphate pH 7.4. 0.5 mg of 776.1 mAb was then added (calculated using the antibody concentration to establish the volume required). This was followed by the addition of 35 µl of a 1 mg/ml solution of IODO-GEN in acetonitrile. After a 3 minute incubation, 100 µl of a solution of ascorbic acid (25 mg/ml, pH 5.0) was added. After another 5 minutes, 100 µl of 0.1% murine serum albumen (MSA) in 50 mM PBS was added. After another 4 minute incubation, $^{131}$I incorporation was analyzed by instant thin layer chromatography (ITLC) in normal saline. Unincorporated iodine was removed by separation using Sephadex G-25 chromatography with prepacked NAP-10 columns (Amersham-Pharmacia) with PBS containing 0.1% MSA as buffer. All procedures were performed at room temperature. Purified mAb was analyzed for free iodine content again by ITLC, and was considered suitable if free iodine was <5% of the total iodine present.

Immunoreactivity of Radiolabeled 776.1 by ELISA

The immunoreactivity of radiolabeled 776.1 was determined by ELISA assay. Immunlon 4 (Dynatech) 96 well plates were coated with 100 µl per well of O772P 3-repeat with a hemagglutinin (HA) tag (affinity-purified) at 1 µg/ml in DPBS overnight at 4° C. The next day, the plates were blocked with 200 µl per well of blocking buffer (1×PBS with 1% BSA) for 1 hour at room temperature. Unlabeled and radiolabeled 776.1 were diluted to 3 µg/ml in blocking buffer and added to the first row of the blocked plate in triplicate at 150 µl per well; 100 µl of blocking buffer was added to the remaining wells. Antibodies were then serially diluted threefold for a total of 7 dilutions. The plate was incubated for 1 hour at room temperature followed by three washes with DPBS containing 0.05% Tween-20 (PBST; 200 µl per well). For signal detection, 100 µl of HRP-conjugated goat anti-mouse IgG (Amersham Biosciences Piscataway, N.J.), diluted 1:2000, was added to each well and incubated for 1 hour at room temperature. The plates were washed three times with PEST and the HRP conjugate was detected by adding a mixture of TMB (KPL) substrate and $H_2O_2$ (1:1 ratio; 100 µl/well). Plates were incubated for 10 minutes and the absorbance was measured at 650 nm using a plate reader (Molecular Devices). Immunoreactivity was determined by comparing the concentrations of radiolabeled and unlabeled antibody where 50% saturation was achieved.

Single-Dose Radioimmunotherapy (RIT) with [$^{131}$I]776.1

Mice bearing established OVCAR-3 tumors (ideally ranging in volume from 150 mm$^3$ to 250 mm$^3$) were administered a single i.v. injection of [$^{131}$I]776.1 (mouse IgG$_1$) in 0.2 ml 0.9% sodium chloride. For all studies, groups of 10 mice received either 100 or 300 µCi of [$^{131}$I]776.1 in 0.9% sodium chloride. Control groups consisted of mice injected with 0.9% sodium chloride alone or unlabeled 776.1 at a dose equivalent to the protein dose given in the high-dose radiolabeled 776.1 group. Tumors were measured two times per week. Mice were sacrificed when the tumor volume was greater than 10% of their body weight.

Results:

[$^{131}$I]776.1 IgG1 antibody, administered as a single, intravenous dose in an OVCAR-3 xenograft tumor model of human ovarian cancer, was effective in slowing tumor growth compared with IgG1 control in three studies at the 300 µCi dose, and in two of three studies at the 100 µCi dose. See FIG. 12 for a summary of one of the studies. Compared with saline control, [$^{131}$I]776.1 IgG1 was effective in slowing tumor growth in two of three studies at both the 100 µCi and 300 µCi doses. In two of three studies, [$^{131}$I]776.1 IgG1 at the 300 µCi dose demonstrated tumor regression, defined as achieving a mean tumor volume less than the starting tumor volume at the beginning of the study. In one study, no statistical slowing of tumor growth was observed for either [$^{131}$I]776.1 IgG1 treatment group compared with saline control and no regression was observed for the 300 µCi [$^{131}$I]776.1 IgG1 dose group. Starting mean tumor volumes at the beginning of this particular study were, however, significantly larger than in the remaining two studies.

Similar results were obtained using a [$^{90}$Y]776.1 radiolabeled antibody. In particular, a significant reduction in tumor growth (p<0.05) was observed. In three of four studies, significant reduction in growth was observed at both 50 µCi and 150 µCi doses of the antibody. In these same three studies, regression of tumor growth was observed at the highest dose of [$^{90}$Y]776.1, and the effect on tumor growth was equal to, or better than 3 doses of 6 mg/kg cisplatin.

7.0. ANTIBODY/ANTIGEN-BINDING ANTIBODY FRAGMENT COMPETITION ASSAYS

ELISA Cross-Competition Assay

Antibodies to be tested are biotinylated using the EZ-Link Sulfo-NHS-LC-Biotinylation Kit (Pierce Biotechnology, Rockford, Ill.), according to the manufacturer's instructions, followed by removal of unreacted biotinylation reagent by dialysis against 1 L phosphate-buffered saline with 2 buffer changes at 4° C. for 48 hours. Ninety-six well plates are coated with 100 µl (per well) of 1 µg/ml 3 rpt-O772P in bicarbonate buffer (0.2 M $Na_2CO_3$/$NaHCO_3$, pH 9.6, Sigma) overnight at 4° C.

The next day, the plates are washed three times with 200 µl 1×PBST (1× phosphate-buffered saline (PBS), 0.05% Tween 20) and blocked with 100 µl of 1×PBST containing 1% bovine serum albumin (BSA) for 1 hour at room temperature. After three washes with 1×PBST, a titration curve from 0- to 1000-fold excess competitor antibody (relative to the labeled antibody added at a later step) in 95 µl 1×PBST+1% BSA which is added to the plate in separate wells and incubated for 1 hour at 37° C. Biotinylated antibody is then added in 5 µl 1×PBST+1% BSA, and incubated for an additional 1 hour at morn temperature. The concentration of biotinylated antibody added is that concentration at which 70% maximal binding of O772P 3-rpt protein is achieved in the absence of competitor using the detection conditions described below. The amount of antibody added is dependant upon the binding characteristics and is routinely determined empirically in pilot studies.

The plates are then washed three times with 1×PBST. For signal detection, 100 µl of Streptavidin-HRP (1:4000-1:8000 dilution into 1×PBST+1% BSA, Southern Biotechnology Associates, Inc. (Birmingham, Ala.)), is added into each well and incubated for 1 hour at room temperature. The plates are then washed three times with 1×PBST. Finally, 100 µl mixture of TMB substrate and $H_2O_2$ (1:1 ratio, KPL) is added into each well and the absorbance is measured at 405 nm with a plate reader (Molecular Devices Corp., Sunnyvale, Calif.). The assay is done in triplicate for each antibody and average values are calculated.

Non-specific competition is determined using normal mouse IgG1 in place of specific competitor. Controls for blank and individual reagents, as well as self-competition, are also included in each experiment. Percent inhibition (minus non-specific competition) is plotted as a function of competitor competition, and the $IC_{50}$, or the concentration of competitor at which 50% competition is observed is determined.

FACS Cross-Competition Assay

Antibodies to be tested are biotinylated using the EZ-Link Sulfo-NHS-LC-Biotinylation Kit (Pierce Biotechnology, Rockford, Ill.), according to the manufacturer's instructions, followed by removal of unreacted biotinylation reagent by dialysis against 1 L phosphate-buffered saline with 2 buffer changes at 4° C. for 48 hours. Cultured OVCAR-3 cells are harvested and washed in FACS buffer (1× Dulbecco's phosphate-buffered saline (DPBS), 0.05% $NaN_3$, 2% BSA). Competition assays are prepared in 96 well plates in a 50 µl total volume.

A titration from 0- to 1000-fold excess of unlabeled competitor antibody (relative to the biotinylated antibody added at a later step) in 20 µl is added to 25 µl of OVCAR-3 cells ($4\times10^5$) suspended in FACS buffer (in separate wells), thoroughly mixed, dispensed into a 96 well plate, and incubated at room temperature for 30 minutes. Five microliters of biotinylated antibody in FACS buffer are then added to each well containing cells, thoroughly mixed, and incubated at room temperature for an additional 30 minutes. The amount of antibody used is the minimal concentration at which maximal binding of OVCAR-3 cells, expressed as percent positive cells, is achieved. The amount of antibody added is dependant upon the binding characteristics and is routinely determined empirically in pilot studies.

Cells are then collected and washed twice with 200 µl of FACS buffer. For signal detection, cells are incubated with 50 µl of 1 µg/ml for FITC-conjugated streptavidin (prepared with FACS buffer, Molecular Probes, Eugene, Oreg.) for 30 minutes at room temperature. After washing twice with 200 µl of FACS buffer, cells from individual wells are then resuspended in 400 µl of FACS buffer and subjected to FACS analysis. FACS analysis was performed according to manufacturer's recommendation using FACScan instrumentation and CellQuest software (Becton Dickinson). The data obtained at each experimental condition represent 10,000 events. Controls for blank and individual reagents, and self-competition are also performed for each experiment. Percent inhibition (minus non-specific competition), or the reduction in the percent-positive staining OVCAR-3 cells, is plotted as a function of competitor competition, and the $IC_{50}$, or the concentration of competitor at which 50% competition is observed, is determined.

An antibody is considered to compete if the $IC_{50}$ for the competitor is at a concentration no more than about 100-fold above the labeled antibody. More preferably, an antibody is considered to compete if the $IC_{50}$ for the competitor is at a concentration no more than about 10-fold above the labeled antibody. More preferably, an antibody is considered to compete if the $IC_{50}$ for the competitor is at a concentration no more than about equimolar to the labeled antibody.

8.0. HYBRIDOMA DEPOSITS

Hybridoma 117.1, secreting monoclonal antibody 117.1 was deposited on Aug. 2, 2002, with the American Type Culture Collection (ATCC®), 10801 University Boulevard, Manassass, Va. 20110-2209, under the provisions of the Budapest Treaty on the International Recognition of the Deposit of Microorganisms for the Purpose of Patent Procedures, and assigned accession number PTA-4567.

Hybridoma 368.1 secreting monoclonal antibody 368.1 was deposited on Aug. 2, 2002, with the ATCC®, under the provisions of the Budapest Treaty on the International Recognition of the Deposit of Microorganisms for the Purpose of Patent Procedures, and assigned accession number PTA-4568.

Hybridoma 501.1, secreting monoclonal antibody 501.1 was deposited on Aug. 2, 2002, with the ATCC® under the provisions of the Budapest Treaty on the International Recognition of the Deposit of Microorganisms for the Purpose of Patent Procedures, and assigned accession number PTA-4569.

Hybridoma 776.1, secreting monoclonal antibody 776.1 was deposited on Aug. 2, 2002, with the ATCC®, under the provisions of the Budapest Treaty on the International Recognition of the Deposit of Microorganisms for the Purpose of Patent Procedures, and assigned accession number PTA-4570.

Hybridoma 15C9 secreting monoclonal antibody 15C9 was deposited on Apr. 3, 2003, with the ATCC®, under the provisions of the Budapest Treaty on the International Recognition of the Deposit of Microorganisms for the Purpose of Patent Procedures, and assigned accession number PTA-5106.

Hybridoma 16C7 secreting monoclonal antibody 16C7 was deposited on Apr. 3, 2003, with the ATCC®, under the provisions of the Budapest Treaty on the International Recognition of the Deposit of Microorganisms for the Purpose of Patent Procedures, and assigned accession number PTA-5107.

Hybridoma 16H9 secreting monoclonal antibody 16H9 was deposited on Apr. 3, 2003, with the ATCC®, under the provisions of the Budapest Treaty on the International Recognition of the Deposit of Microorganisms for the Purpose of Patent Procedures, and assigned accession number PTA-5108.

Hybridoma 4E7 secreting monoclonal antibody 4E7 was deposited on Apr. 3, 2003, with the ATCC®, under the provisions of the Budapest Treaty on the International Recognition of the Deposit of Microorganisms for the Purpose of Patent Procedures, and assigned accession number 5109.

Hybridoma 7A11 secreting monoclonal antibody 7A11 was deposited on Apr. 3, 2003, with the ATCC®, under the provisions of the Budapest Treaty on the International Recognition of the Deposit of Microorganisms for the Purpose of Patent Procedures, and assigned accession number PTA-5110.

Hybridoma 7C6 secreting monoclonal antibody 7C6 was deposited on Apr. 3, 2003, with the ATCC®, under the provisions of the Budapest Treaty on the International Recognition of the Deposit of Microorganisms for the Purpose of Patent Procedures, and assigned accession number PTA-5111.

Hybridoma 7F10 secreting monoclonal antibody 7F10 was deposited on Apr. 3, 2003, with the ATCC®, under the provisions of the Budapest Treaty on the International Recognition of the Deposit of Microorganisms for the Purpose of Patent Procedures, and assigned accession number PTA-5112.

Hybridoma 7G10 secreting monoclonal antibody 7G10 was deposited on Jun. 4, 2003, with the ATCC®, under the provisions of the Budapest Treaty on the International Recognition of the Deposit of Microorganisms for the Purpose of Patent Procedures, and assigned accession number 5245.

Hybridoma 7H1 secreting monoclonal antibody 7H1 was deposited on Apr. 3, 2003, with the ATCC®, under the provisions of the Budapest Treaty on the International Recognition of the Deposit of Microorganisms for the Purpose of Patent Procedures, and assigned accession number PTA-5114.

Hybridoma 8A1 secreting monoclonal antibody 8A1 was deposited on Apr. 3, 2003, with the ATCC®, under the provisions of the Budapest Treaty on the International Recognition of the Deposit of Microorganisms for the Purpose of Patent Procedures, and assigned accession number PTA-5115.

Hybridoma 8B5 secreting monoclonal antibody 8B5 was deposited on Apr. 3, 2003, with the ATCC®, under the provisions of the Budapest Treaty on the International Recognition of the Deposit of Microorganisms for the Purpose of Patent Procedures, and assigned accession number PTA-5116.

Hybridoma 8C3 secreting monoclonal antibody 8C3 was deposited Jun. 4, 2003, with the ATCC®, under the provisions of the Budapest Treaty on the International Recognition of the Deposit of Microorganisms for the Purpose of Patent Procedures, and assigned accession number 5246.

Hybridoma 8E3 secreting monoclonal antibody 8E3 was deposited on Apr. 3, 2003, with the ATCC®, under the provisions of the Budapest Treaty on the International Recognition of the Deposit of Microorganisms for the Purpose of Patent Procedures, and assigned accession number PTA-5118.

Hybridoma 8G9 secreting monoclonal antibody 8G9 was deposited on Apr. 3, 2003, with the ATCC®, under the provisions of the Budapest Treaty on the International Recognition of the Deposit of Microorganisms for the Purpose of Patent Procedures, and assigned accession number PTA-5119.

Hybridoma 325.1 secreting monoclonal antibody 325.1 was deposited on Apr. 3, 2003, with the ATCC®, under the provisions of the Budapest Treaty on the International Recognition of the Deposit of Microorganisms for the Purpose of Patent Procedures, and assigned accession number PTA-5120. Hybridoma 325.1 secreting monoclonal antibody 325.1 was deposited on Apr. 3, 2003, with the ATCC®, under the provisions of the Budapest Treaty on the International Recognition of the Deposit of Microorganisms for the Purpose of Patent Procedures, and assigned accession number PTA-5120.

Hybridoma 621.1 secreting monoclonal antibody 621.1 was deposited on Apr. 3, 2003, with the ATCC®, under the provisions of the Budapest Treaty on the International Recognition of the Deposit of Microorganisms for the Purpose of Patent Procedures, and assigned accession number PTA-5121.

Hybridoma 633.1 secreting monoclonal antibody 633.1 was deposited on Apr. 3, 2003, with the ATCC®, under the provisions of the Budapest Treaty on the International Recognition of the Deposit of Microorganisms for the Purpose of Patent Procedures, and assigned accession number PTA-5122.

Hybridoma 654.1 secreting monoclonal antibody 654.1 was deposited Jun. 4, 2003, with the ATCC®, under the provisions of the Budapest Treaty on the International Recognition of the Deposit of Microorganisms for the Purpose of Patent Procedures, and assigned accession number 5247.

Hybridoma 725.1 secreting monoclonal antibody 725.1 was deposited on Apr. 3, 2003, with the ATCC®, under the provisions of the Budapest Treaty on the International Recognition of the Deposit of Microorganisms for the Purpose of Patent Procedures, and assigned accession number PTA-5124.

Hybridoma 446.1 secreting monoclonal antibody 446.1 was deposited on Sep. 25, 2003, with the ATCC®, under the provisions of the Budapest Treaty on the International Recognition of the Deposit of Microorganisms for the Purpose of Patent Procedures, and assigned accession number PTA-5549.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference. Citation or discussion of a reference herein shall not be construed as an admission that such is prior art to the present invention.

The invention claimed is:

1. An isolated nucleic acid molecule comprising a nucleotide sequence that encodes a variable chain region selected from the group consisting of SEQ ID NOs:27, 28, 31, 32, 33, 34, 53, 54 55, and 56.

2. The nucleic acid molecule of claim 1, wherein the nucleic acid molecule comprises the nucleotide sequence selected from the group consisting of SEQ ID NOs:35, 36, 39, 40, 41, 42, 52, 57, 58 and 59.

* * * * *